US007764763B2

(12) United States Patent
Mori

(10) Patent No.: US 7,764,763 B2
(45) Date of Patent: Jul. 27, 2010

(54) X-RAY CT SYSTEM, IMAGE RECONSTRUCTION METHOD FOR THE SAME, AND IMAGE RECONSTRUCTION PROGRAM

(75) Inventor: Issei Mori, Miyagi (JP)

(73) Assignee: Tohoku University, Sendai-shi (JP)

( * ) Notice: Subject to any disclaimer, the term of this patent is extended or adjusted under 35 U.S.C. 154(b) by 0 days.

(21) Appl. No.: 12/339,592

(22) Filed: Dec. 19, 2008

(65) Prior Publication Data
US 2009/0168952 A1 Jul. 2, 2009

Related U.S. Application Data

(63) Continuation of application No. PCT/JP2007/062428, filed on Jun. 20, 2007.

(30) Foreign Application Priority Data
Jun. 22, 2006 (JP) ............................. 2006-173123

(51) Int. Cl.
*A61B 6/03* (2006.01)
(52) U.S. Cl. ................................. 378/19; 378/4; 378/11
(58) Field of Classification Search ...................... 378/4, 378/15, 19, 205, 901, 11
See application file for complete search history.

(56) References Cited

U.S. PATENT DOCUMENTS 5,825,842 A 10/1998 Taguchi
6,272,200 B1 * 8/2001 Pan et al. ...................... 378/15
6,332,013 B1 * 12/2001 Hsieh ........................... 378/15
6,529,575 B1 * 3/2003 Hsieh ............................. 378/4
2005/0058239 A1 3/2005 Mori
2005/0226365 A1 10/2005 Taguchi
2006/0029285 A1 2/2006 Hein et al.

(Continued)

FOREIGN PATENT DOCUMENTS

JP 2005-40236 A 2/2005

(Continued)

OTHER PUBLICATIONS

Silver et al., Windmill artifact in multi-slice helical CT, 2003, SPIE, vol. 5032, pp. 1918-1927.*

(Continued)

*Primary Examiner*—Edward J Glick
*Assistant Examiner*—John M Corbett
(74) *Attorney, Agent, or Firm*—Westerman, Hattori, Daniels & Adrian, LLP

(57) ABSTRACT

It is an object of the present invention to eliminate windmill artifacts that inevitably occurs when a helical scan is performed with an X-ray CT system. To this end, the present invention is equipped with an X-ray source, and an X-ray detector having a plurality of detector elements arranged two-dimensionally, and disposed opposite to the X-ray source with a predetermined rotation center axis therebetween. The invention further includes reconstruction means for performing an arithmetic operation, in which two-dimensional projection data obtained based on X-ray detection data detected by the detector elements while rotating the X-ray source around the rotation center axis are back projected along a path different in a Z-axis direction extending along the rotation center axis from the X-ray path of the projection data, to reconstruct an image.

12 Claims, 27 Drawing Sheets

U.S. PATENT DOCUMENTS

2006/0126779 A1* 6/2006 Basu et al. .............. 378/4
2008/0247507 A1* 10/2008 Shechter ............... 378/19

FOREIGN PATENT DOCUMENTS

JP      2005-279282 A    10/2005
JP      2006-43431 A     2/2006

OTHER PUBLICATIONS

Kalender, Willi A.; "Computed Tomography"; Publicis Corporate Publishing, Erlangen, pp. 76-97, 2005.

Nobuta, Yasuo; "Advanced Multislice X-Ray CT Scanner"; online, Toshiba Review, vol. 57, No. 2, pp. 9-12, Jun. 7, 2006.

Tsujioka, K.; "Equipment Engineering of X-Ray CT Scanner (4) - Development of Multiscile CT Scanners- ,"online, Japanese Radiation Technical Society Journal, vol. 58, No. 5, pp. 651-657, Jun. 7, 2006.

Silver, Michael D. et al.; "Field-of-view dependent helical pitch in multi-slice CT"; Proceedings of SPIE 4320, pp. 839-850, 2001.

Flohr, T. G. et al.; "Image reconstruction and image quality evaluation for a 64-slice CT scanner with z-flying focal spot"; Medical Physics, vol. 32, No. 8, pp. 2536-2547, Aug. 2005.

Mori, I. et al.; "Alleviation of Aliasing Artifact in CT"; Medical Imaging Technology, vol. 21, No. 4, Sep. 2003.

* cited by examiner

16-Row Multislice CT, Scan Slice Thickness 1 mm, Helical Pitch 13 (Beam Pitch 0.8125), Visual Field 500 mm $\phi$, 900 Views/Rotation FIG. 7(a)
FIG. 7(b)
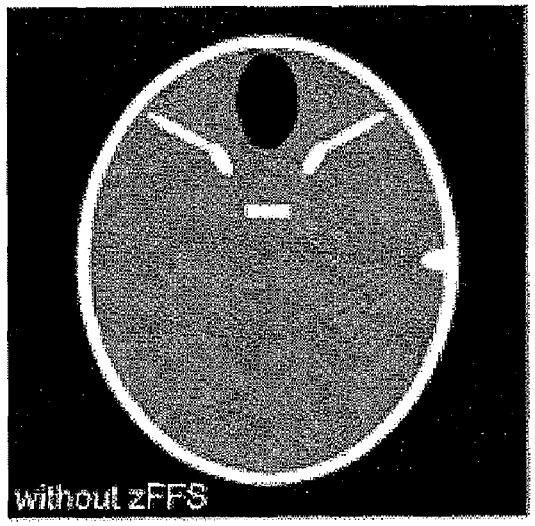
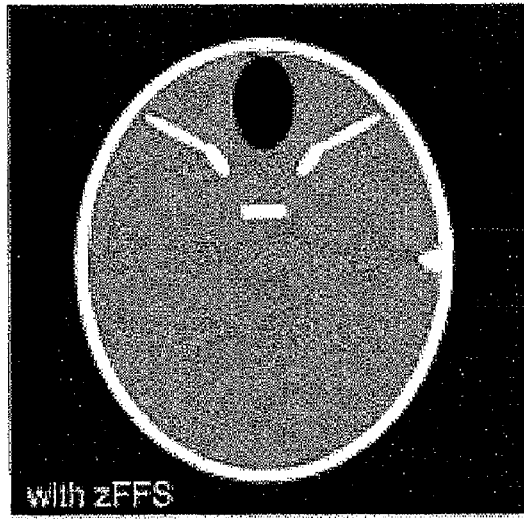
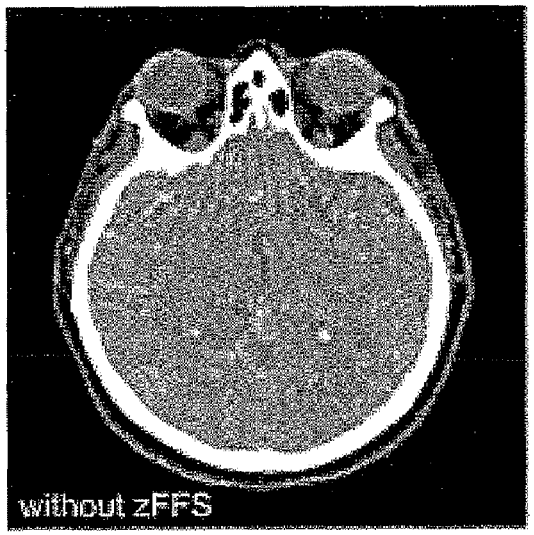
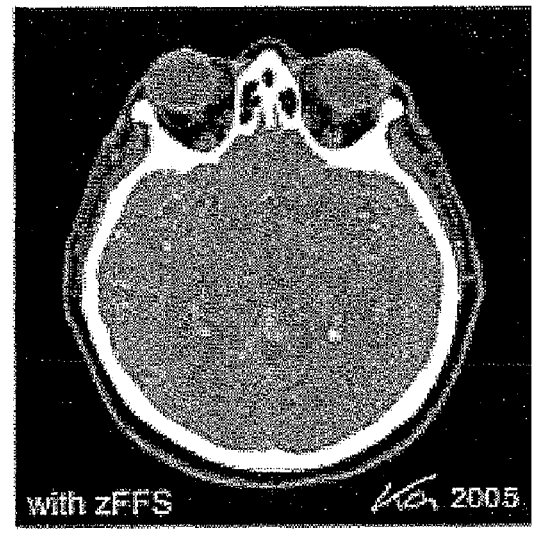
FIG. 7(c)
FIG. 7(d)

X-RAY CT SYSTEM, IMAGE RECONSTRUCTION METHOD FOR THE SAME, AND IMAGE RECONSTRUCTION PROGRAM

TECHNICAL FIELD

The present invention relates to an X-ray computed tomography (CT) system (also sometimes simply called CT) that illuminates a test subject with X-rays, acquires the X-ray transmitted data, and obtains an image about the internal structure of the test subject from the acquired X-ray data, an image reconstruction method for the same, and an image reconstruction program, and more particularly to techniques well-suited for improving image quality in performing a helical scan with a multislice CT.

BACKGROUND ART

At present, one representative radiation diagnosis system is an X-ray CT system. With the advent of helical scanning, the clinical significance of high-speed scanning has been made clear. Nowadays, for further speedup, a helical scan is usually performed with a multislice CT (also called a multiple-row CT or multi detector row CT (MDCT)). For details on multislice CTs and helical scanning, see, for example, non-patent documents 1, 2, and 3.

The X-ray measuring system (also referred to simply as "measuring system") of the scanner of a multislice CT is illustrated in FIG. 1 by way of example. A plurality of X-ray detector elements (also referred to simply as "detector elements") 101 are arranged in a fan-angle ($\phi$) direction in FIG. 1 and form one row, and furthermore, a plurality of rows of detector elements are arranged in a Z-axis direction crossing the fan-angle direction, thereby forming a multiple-row detector 100. Therefore, it is also sometimes called a multiple-row CT. In FIG. 1 the X-ray detector elements in the Z-axis direction are 12 rows, but in actuality, they are more than tens of rows.

Although not illustrated in FIG. 1, there is a data acquisition system (DAS) for measuring an analog signal from the detector element 101 and converting the analog signal into a digital signal. A number of DASs are provided according to the number of rows of detector elements 101, but the number of DASs is normally smaller than the number of rows of detector elements 101 (e.g. in the example of FIG. 1, 4 DASs, compared with 12 rows). In the case of multislice CTs, the number of rows is called in the number of DASs, not the number of rows of detector elements 101. That is, if there are four DASs, the corresponding CT is called a 4-row multislice CT.

In FIG. 1, an X-ray source 200 radiates X-rays with a cone angle (X-ray beam thickness) which covers 8 rows of detector elements 101, through a slit (collimator) 300. DAS, for example, can bundle two rows of detector elements 101 together, process it as one row, and handle 4 rows of X-ray measurement data in total. That is, in this case, practically two rows of detector elements 101 function as one row of detector elements having double length in the Z-axis direction. For such bundling, there are cases where no bundling is performed depending upon inspection purposes, or 4 rows or 8 rows of detector elements 101 can be freely bundled.

One row made by bundling rows forms one row of detector elements, so the "detector element row" used in the following description, unless otherwise specified, does not mean rows each of which is formed of detector elements 101, but does mean a detector element row made by bundling rows of detector elements. Therefore, for instance, "the arrangement pitch in the Z-axis direction of detector element rows" means the arrangement pitch in the Z-axis direction of data that are handled by DAS. If two rows are bundled, the arrangement pitch in the Z-axis direction of detector element rows is twice the pitch between the detector element rows actually arranged in the detector 100.

Note that the X-ray detector element 101 outputs an electrical signal proportional to the intensity of X-rays transmitted through a radiography subject. The electrical signal is measured by DAS. In the following description, the data thus obtained is sometimes referred to as X-ray detection data or X-ray data.

In addition, projection data are data obtained by integrating the X-ray attenuation coefficients of a test subject along a path of X-rays connecting the X-ray source 200 and each detection element 101. The projection data are obtained by suitably converting the X-ray measurement data output of DAS. If, in a certain projection angle direction (rotational angle of the measuring system of FIG. 1), projection data are acquired over the range in which the detector elements 101 are arranged in the fan angle ($\phi$) direction, and the data acquisition is performed through one rotation, then enough projection data to reconstruct an image are obtained (Note that one rotation is not always needed. It is sufficient if the data acquisition is performed in a rotational angle range sufficiently greater than half a rotation). This is the principle of CT. Multislice CTs are designed to simultaneously perform this acquisition of projection data at a plurality of Z-axis direction positions.

Helical scanning is a scanning method in which, while this measuring system is continuously rotating around a test subject (or a photography subject), the test subject moves at a fixed speed in the Z-axis (test subject axis or rotation center axis) direction. That is, as schematically illustrated in FIG. 2, helical scanning is high-speed scanning such that the measuring system describes a spiral orbit with respect to a test subject 400.

It is well known that if a helical scan is performed with a multislice CT, artifacts (abnormal patterns) occur in an image. Because of its shape, the artifact is called a windmill artifact. This artifact occurs primarily at a place where the structure of a photography subject changes sharply. The name of the windmill derives from an image illustrated in FIG. 3.

The image illustrated in FIG. 3 was obtained by scanning 17 spheres (radius 15 mm) with a high X-ray attenuation coefficient (CT value 2000) disposed one at the center of rotation and respectively four at each of positions of radii 100 mm, 140 mm, 180 mm, and 220 mm, and performing image reconstruction with the outer peripheral portion (position of Z=14 mm with the center of a sphere at the center of rotation as zero (Z=0 mm)) of each sphere as an image reconstructing plane (imaging position). Although 17 white small circular regions should be obtained as a correct artifact-free image, black and white streaks in the shape of a windmill have occurred around the spheres. These are windmill artifacts.

As the same photography subjects and helical scanning conditions as those of FIGS. 3 and 4 will be employed later to show advantages of the present invention, a brief description will be given below.

The helical scanning conditions, as illustrated in FIG. 3, are "16-row multislice CT, scan slice thickness 1 mm, helical pitch 13 (beam pitch 0.8125), field of view 500 mm$\phi$, and 900 views/rotation."

Since, in FIG. 1, it is assumed that there are 4 DASs, the X-ray beam is partitioned into four sheets. Therefore, in the case of a 16-row multislice CT, there are 16 DASs, so the X-ray beam is partitioned into 16 sheets.

The "scan slice thickness 1 mm" means that the thickness of each of the four X-ray beam sheets partitioned is 1 mm at the center of rotation. In the case where detector element rows are arranged in the Z-axis direction with a finer pitch than that of DAS, each of the partitioned X-ray beams is formed by bundling of a number of detector element rows.

The "helical pitch 13" means that the photography subject moves in the Z-axis direction by 13 times the scan slice thickness, i.e. 13 mm while the scanning system makes one rotation. Likewise, the "beam pitch 0.8125" means that the photography subject moves in the Z-axis direction by 0.8125 times the overall thickness of the X-ray beam at the center of rotation during one rotation.

The image reconstruction method used herein is a method called TCOT (True Cone beam Tomography reconstruction algorithm), a detailed description of the theory being disclosed, for example, in patent document 2 and non-patent document 4 described later. The image reconstruction method of the present invention is explained by changes in existing reconstruction methods and resultant images. The present invention can select any of a wide variety of image reconstruction methods that can be employed in the helical scanning of multislice CTs, but the reason that TCOT is employed in this specification is as follows.

First, TCOT is a simple method in which projection data with a cone angle (see FIG. 1) are back projected accurately in accordance with the cone angle without approximation, so the explanation of the image reconstruction method of the present invention becomes easy. In addition, performing back projection in accordance with a cone angle is to perform three-dimensional back projection, so the image reconstruction method of the present invention can be very directly applied.

Second, if other image reconstruction methods that have been put to practical use are employed, different kinds of artifacts not handled by the present invention will contaminate an image, but this image reconstruction method reduces the problem and therefore it becomes easy to clearly show advantages of the present invention with an image.

Although the expression "projection data are back projected" is employed, in the image reconstruction by CT, projection data are not back projected as they are. Data obtained by performing a convolution operation or a filtering process on projection data is called convolution corrected projection data or filter corrected projection data, and these corrected projection data are back projected when performing image reconstruction of CT. In performing back projection, it is also necessary to perform an interpolation process on corrected projection data. These will be apparent to those skilled in the art, so in this specification, back projection including these processes is simply expressed as "projection data are back projected."

It is well-known to those skilled in the art that windmill artifacts occur when a sampling pitch in the Z-axis direction is not sufficiently fine. The sampling pitch in the Z-axis direction, as illustrated in FIG. 5, is determined by the arrangement pitch in the Z-axis direction of the detector element rows (each of which is bundled by one of the DASs). Note that FIG. 5 is equivalent to a figure viewed from a side direction crossing the Z-axis direction of the measuring system illustrated in FIG. 1. Directing attention to some of the detector element rows illuminated with X-rays from the X-ray source 200, they are enlarged in the Z-axis direction.

As illustrated in FIG. 5, a line connecting the X-ray source 200 (focus of the X-ray tube) and the detector-element aperture center represents the position of projection data of each row. That is to say, data sampling is performed along this line. At this time, s(r) represents a sampling pitch in the Z-axis direction and depends upon a distance from the Z-axis (a plus sign is taken on the side of the X-ray source 200). A value at the rotation center (iso center) axis (Z-axis) is represented by $s_{iso}$.

This $s_{iso}$ is the same value as the scan slice thickness because it is normally discussed on the assumption that the detector-element aperture width in the Z-axis direction is the same as the Z-axis direction arrangement pitch. In the following description, the scan slice thickness is assumed to be equal to $s_{iso}$. In CT, projection data are only discretely obtained in other directions as well as the Z-axis direction, but since in the following description a discussion is concentrated about the Z-axis direction, unless other specified, the expression "sampling pitch" means a sampling pitch in the Z-axis direction.

The values of projection data at a position between spots where data are being sampled must be obtained by interpolating the projection data obtained by neighboring rows of detector elements. If s(r) (also sometimes referred to simply as s) is sufficiently small, the interpolation result is able to correctly reflect changes in the Z-axis direction of a photography subject, i.e., it becomes a value very close to the true projection data at the intermediate position, so there is no problem. If the sampling pitch s is great, the interpolation result becomes a value away from the true projection data, which can cause artifacts. These artifacts are windmill artifacts, but the reason they show windmill-shaped patterns is omitted here because it will be explained together with helical motion.

If a scan slice is made thick, then the sampling pitch s becomes wide and therefore windmill artifacts occur significantly. In the present CTs, the smallest value of the scan slice thickness $s_{iso}$ is about 0.5 to 0.6 mm. This thickness causes not a great problem, but windmill artifacts occur to the degree illustrated in FIGS. 7(a) and 7(b). In ordinary CT examination, because of examination efficiency (if a scan slice is made thin, it takes time to scan a predetermined Z-axis direction range) and a reduction in image noise (if thin, image noise becomes great), CT is operated with a scan slice thickness of 1 mm or greater, not the thinnest slice. In that case, windmill artifacts are further increased.

If interference with diagnosis by windmill artifacts is to be prevented, a thick image must be made. That is, helical scanning makes it possible to make an image far thicker than the scan slice thickness $s_{iso}$ by use of a large number of projection data away in the Z-axis direction, so that windmill artifacts are averaged and reduced.

If windmill artifacts are to be suppressed to the degree that they are not seen enough, the thickness of an image must be made two or more times a scan slice thickness empirically, although it is a matter of degree. However, in this case, spatial resolution in the Z-axis direction is often insufficient, so this also interferes with clinical diagnosis. After all, an operator needs to determine a trade-off between windmill artifacts and Z-direction spatial resolution to obtain a desired image.

Thus, the problem of windmill artifacts is particularly important. If this is solved, then the possibility of an erroneous diagnosis and clinical difficulty due to artifacts is reduced, inspection time is shortened, and higher definition images are obtained, so that the value of CT diagnosis is enhanced.

As the latest technique to alleviate the windmill problem, that is, the problem of a sampling pitch being coarse, there is a "z-flying focal spot" method disclosed in non-patent document 5 by way of example. The "z-flying focal spot" will hereinafter be referred to as zFFS.

This method, for instance, as illustrated in FIG. 6, is one in which a focal position is alternately moved (back and forth) in the Z-axis direction during a scan. In CT, projection data are acquired, for example, in 1000 directions, i.e., for each 0.36 degrees, one set of projection data obtained at one angle being called a view. That is, for each view, in other words, between odd and even views, focal positions are interchanged. Such interchanging is called flying. This focus flying width (flying distance) is set such that, for example, $\alpha_{iso}$ illustrated in FIG. 6 becomes ¼.

As a result, as illustrated in FIG. 6, paths (see dotted lines) of projection data at odd and even views are positioned so that they are alternately threaded through the intervals. In FIG. 6, a solid line represents a projection data position (path) when the zFFS method is not applied, that is, a focal position is not moved, and a (r) represents a distance between a first projection data position when the zFFS method is not applied and a second projection data position when the zFFS method is applied. In addition, $R_F$ represents a distance between the center of rotation and the focus, and $R_{FD}$ represents a distance from the focus to the detector-element row (detector-element aperture center).

If a difference in projection angle between adjacent views is neglected, that is, if a difference in projection data due to a difference in projection angle direction is approximated to be almost negligible, when odd and even views are added together, the interval between dotted lines of FIG. 6 is one-half the scan slice thickness $s_{iso}$ at the center of rotation. Thus, the sampling pitch has become fine.

As a result, images having windmill artifacts suppressed can be obtained as illustrated in FIGS. 7(b) and 7(d). In a clinical image illustrated in FIG. 7(c) streaks flowing downward from the top bone structure are windmill artifacts. In a simulation image illustrated in FIG. 7(a), streaks occurring from the right protrusion, and streaks occurring from the edge of the top cavity, are windmill artifacts. These are improved as illustrated in FIGS. 7(d) and 7(b) by the zFFS method.

The images illustrated in FIGS. 7(b) and 7(d) are obtained by the image reconstruction method of non-patent document 5, and although approximation errors occur, projection data for each view are handled as being acquired along a path indicated with a dotted line in FIG. 6. Therefore, even in the case of the image reconstruction method disclosed in non-patent document 5, back-projection is basically performed along a path where projection data were acquired.

With the conditions previously described in FIGS. 3 and 4, a simulation image obtained when the zFFS method is applied is illustrated in FIG. 8. Windmill artifacts have been suppressed over the whole region. However, windmill artifacts near the center of the visual field are satisfactorily reduced, but windmill-artifact suppression becomes smaller as spheres are positioned away from the center. Particularly, in the top portion of the image, the suppression effect is extremely small. In addition, except the image center portion, feeble streaks appear as straight fine lines, and particularly in the lower left portion, shower-shaped or striped artifacts become predominant. These will be described later.

The image reconstruction method used herein, that is, the reconstruction method by which an image illustrated in FIG. 8 was obtained is not completely the same as the method in non-patent document 5, but even if the same method as non-patent document 5 is employed, results better than the result illustrated in FIG. 8 cannot be obtained. In all of the existing image reconstruction methods, back projection is commonly performed along a path where projection data were acquired. A difference resides only in that in the case of non-patent document 5 slight approximation errors occur, while the image reconstruction method used herein does not cause any approximation error. As described later, the particularly important feature of the present invention resides in a difference between the case of performing back projection along a path in which projection data were obtained, and the case of performing back projection along an entirely different path from that path.

Note that patent document 1 and non-patent document 6 disclose techniques for eliminating fine shower-shaped artifacts, so-called aliasing artifacts, by suitably handling unequal-interval sampling data in an imaging plane, not a Z-axis direction.

Patent document 1: Japanese patent laid-open publication No. 2005-40236.

Patent document 2: U.S. Pat. No. 5,825,842.

Non-patent document 1: W. Kalender, "Computed Tomography," Publicis Corporate Publishing, Erlangen (2005).

Non-patent document 2: Y. Nobuta, "CT system advancing speedup," online, Toshiba Review Vol. 57, No. 2 (2002), Jun. 7, 2006 retrieval, Internet <URL:http://www.toshiba.co.jp/tech/review/2002/02/57_02pdf/a03.adf>.

Non-patent document 3: K. Tsujioka, "Equipment Engineering (4) of X-Ray CT System—Development of Multi-slice CT—," online, Japanese Radiation Technical Society Journal Vol. 58, No. 5 (May 2002), Jun. 7, 2006 retrieval, Internet <URL:http://www.nv-med.com/jsrt/pdf/2002/58_5/651.pdf>.

Non-patent document 4: M. Silver, K. Taguchi, K. Han, "Field of view dependent helical pitch in cone-beam CT," Proc. SPIE 4320, 839-850 (2001), San Diego, Calif., U.S.A.

Non-patent document 5: T. Flohr et. al, "Image reconstruction and image quality evaluation for a 64-slice CT scanner with z-flying focal spot," Medical Physics 32 (8) page 2536-2547 (August 2005).

Non-patent document 6: I. Mori et. al, "Alleviation of aliasing artifact in CT," Medical Imaging Technology Vol. 21, No. 4, September 2003.

DISCLOSURE OF THE INVENTION

Problems to be Solved by the Invention

However, the above-described zFFS method has the following problems and limits:

(1) The sampling pitch obtained by adding odd and even views together is half $s_{iso}$ at the center of rotation, but if the distance r from the center of rotation is not zero, odd and even views have no positional relationship of being alternately threaded through the intervals. In addition, the effect of the zFFS method is reduced as |r| becomes greater, and if reaching a position where both views intersect each other, that is, a distance $r_{lim}$ from the center of rotation toward the focus, the zFFS method will lose all meaning in a range beyond that distance. In typical CTs, this $r_{lim}$ is 180 mm or so. That is, the zFFS method is unable to exhibit an effect unless the radiography subject is small. In FIG. 8 there is no place where windmill-artifact suppression is totally ineffective, but the reason is that because this image is made from data obtained over about ⅔ of one rotation, though not full one rotation, an averaged effect is obtained to some degree. Still, the zFFS method cannot exhibit a sufficient effect.

(2) This technique cannot be implemented unless the scan slice thickness $s_{iso}$ is extremely small. In CT disclosed in non-patent document 5, the scan slice thickness $s_{iso}$ can be selected from among 0.6 mm, 1.2 mm, and 2.4 mm, but this technique can be applied only when the scan slice thickness is 0.6 mm. Originally, it is necessary to make the sampling pitch smaller than the scan pitch slice thickness $s_{iso}$ particularly when the scan slice thickness $s_{iso}$ is great. Therefore, if this technique cannot be applied when the $s_{iso}$ is great, the significance is diminished. The reason is explained in FIG. 9. X-rays are generated by an X-ray tube, and as schematically illustrated in FIG. 9, the X-ray tube is designed to generate X-rays by emitting an accelerated electron beam to a target 500. Note in FIG. 9 that dimensions are reduced in the vertical direction and enlarged in the horizontal (Z-axis) direction. The target 500 has a certain target angle θ and in CT, θ has to be reduced to about 7 to 10 degrees from all circumstances. In the zFFS method the orbit of an electron beam is changed by electromagnetic means to change the Z-position of a focus, but because of this target angle θ, the focal position must be greatly shifted in the direction of radius r, as indicated with $\Delta R_F$ in FIG. 9, as well as the Z-axis direction. In the zFFS method a quantity that is desired as the flying width in the Z-axis direction of the focus is proportional to $s_{iso}$, so if the zFFS method is to be executed as it is, $\Delta R_F$ is likewise increased in proportion to $s_{iso}$. In typical design of CT, $s_{iso}$ is 0.6 mm, 1.2 mm, and 2.4 mm, while $\Delta R_F$ is approximately 5.5 mm, 11 mm, and 22 mm. The zFFS method is originally effective particularly when the scan slice thickness $s_{iso}$ is great, but the reason the application of the zFFS method must be given up is considered to be due to the difficulty of greatly changing the orbit of an electron beam as soon as views are interchanged, and the technical difficulty of assuring an area that functions effectively as a focus on the target over a wide range.

(3) If the focal position changes in the Z-axis direction, the collimator aperture of FIG. 1 must be further widened that much, compared with the case of no change. This means that the exposure of X-rays to a test subject will increase.

(4) As a test subject is measured at different Z-axis positions alternately, the number of views per rotation is increased. In CT, if a certain number of views is not assured per rotation, then shower-shaped artifacts occur due to an insufficient number of views. A minimum number of views for avoiding this depends upon a variety of parameters, but in the zFFS method the minimum number of views will approximately double. Artifacts due to an insufficient number of views appear as fine streaks or showers illustrated in FIG. 8. This is because, in obtaining an image illustrated in FIG. 8, the number of views per rotation is not doubled but remains unchanged. An increase in the number of views results in an increase in the operating bandwidth of the X-ray measuring system for acquiring projection data, whereby noise is increased. This also interferes with a high-speed scan that is performed with high-speed rotation. In addition, as the high-speed operation of the X-ray measuring system and high-speed data processing system to process a large amount of data, system cost becomes unduly high.

It is anticipated from the foregoing problems or limits that the zFFS method will not sphereopted in many CTs in its original conditions.

The present invention has been made in view of the problems and limits described above. Accordingly, it is an object of the present invention to provide an X-ray CT system, an image reconstruction method for the same, and an image reconstruction program, capable of more effectively suppressing windmill artifacts than prior art.

It should be noted that, in addition to the aforementioned object, it can be positioned as one other object of the present invention to produce an operational effect which is derived from each construction illustrated in best modes for carrying out the invention described later, and which is not obtained by prior art.

Means for Solving the Problems

To achieve the aforementioned objects, the present invention employs the following X-ray CT system, image reconstruction method for the same, and image reconstruction program.

(1) That is, the X-ray computed tomography (CT) system of the present invention comprises an X-ray source for radiating X-rays; an X-ray detector disposed opposite to the X-ray source with a predetermined rotation center axis therebetween, and comprising a plurality of detector elements arranged two-dimensionally in a Z-axis direction, which is a direction along the rotation center axis, and a direction crossing the Z-axis direction; a data acquisition unit for acquiring X-ray detection data detected by the plurality of detector elements of the detector; scan means for causing the data acquisition unit to acquire the X-ray detection data detected by the detector by radiating X-rays from the X-ray source at each of rotational angles, while causing the X-ray source and the detector to rotate around the rotation center axis; and reconstruction means for performing an arithmetic operation, in which two-dimensional projection data obtained by processing the acquired X-ray detection data are back projected along a second path different in the Z-axis direction from a first path of X-rays at the time of the detection, to reconstruct an image. Note that "path different in the Z-axis direction" can also be expressed as "path varied in movement and angle by a predetermined quantity in the Z-axis direction".

(2) In the X-ray CT system as set forth in the above (1), a focal position of the X-ray source may be constructed such that it is alternately movable on plus and minus sides in the Z-axis direction for each of the rotational angles.

(3) In the X-ray CT system as set forth in the above (2), projection data that are acquired at either position of the alternate movements of a focus of the X-ray source may be arranged with a sampling pitch $s_{iso}$ along the Z-axis direction at the rotation center axis, and quantities of the alternate movements of the focus of the X-ray source may be determined so that, when Z-axis direction arrangement positions of respective projection data obtained at the alternate focal positions are shifted to be away by $\alpha_{iso}$ (positive value) times $s_{iso}$ at the rotation center axis from a Z-axis direction arrangement position of projection data obtained when the focus is at a middle point between the alternate focal positions, the $\alpha_{iso}$ becomes a value less than ¼.

(4) In the X-ray CT system as set forth in the above (3), Z-axis direction arrangement positions, at which respective projection data obtained at the alternate focal positions are back projected, may be away by $\gamma_{iso}$ (positive value) times $s_{iso}$ at the rotation center axis from the Z-axis direction arrangement position of the projection data obtained when the focus is at the middle point between the alternate focal positions; the $\gamma_{iso}$ may be a value closer to $\alpha_{iso}+(1-4\alpha_{iso})/2k$ than the $\alpha_{iso}$ and the k may be a value that is not infinity.

(5) In the X-ray CT system as set forth in the above (4), the k is preferably a value from approximately 1 to 2.

(6) In the X-ray CT system as set forth in the above (2), in back projecting with the reconstruction means projection data acquired at the alternate positions of the focus of the X-ray source, a distance away from the rotation center axis toward the focus is represented by r. At a position of the r, when attention is directed to projection data in which passed the vicinity of the rotation center axis, a Z-axis direction arrangement pitch of the attention-directed projection data is expressed as a function s(r) of the r, and a Z-axis direction position of the attention-directed projection data is expressed as being away by α(r)s(r) from a Z-axis direction position of arrangement of projection data obtained when the focus is at the middle point between the alternate focal positions. A position, at which the attention-directed projection data are back projected, may be away by γ(r)s(r) from the Z-axis direction position at the r of arrangement of the projection data obtained when the focus is at the middle point between the alternate focal positions. The γ(r) may be significantly different from the α(r) and is a value closer to α(r)+[1−4α(r)]/2k than the α(r), and the k may be a value that is not infinity.

(7) In the X-ray CT system as set forth in the above (6), the k is preferably a value from approximately 1 to 2.

(8) In the X-ray CT system as set forth in the above (1), a focal position of the X-ray source may be constructed such that it is not movable alternately in the Z-axis direction for each of the rotational angles.

(9) In the X-ray CT system as set forth in the above (8), in back projecting with the reconstruction means projection data acquired at the position of the focus of the X-ray source, the projection data may be arranged with a sampling pitch $s_{iso}$ in the Z-axis direction at the rotation center axis. The projection data may be constructed such that they are back projected at a position away in the Z-axis direction by $γ_{iso}$ times $s_{iso}$ in the Z-axis direction at the rotation center axis from a position where the projection data were acquired. The plus and minus signs of the $γ_{iso}$ may be interchanged for each projection angle. The $γ_{iso}$ may be a value up to about ½, not zero.

(10) In the X-ray CT system as set forth in the above (8), in back projecting with the reconstruction means projection data acquired at the position of the focus of the X-ray source, a distance away from the rotation center axis toward the focus is represented by r. At a position of the r, when attention is directed to projection data which passed the vicinity of the rotation center axis, a Z-axis direction arrangement pitch s of the attention-directed projection data is expressed as a function s(r) of the r. A position, at which the attention-directed projection data are back projected, is expressed as being away by ±γ(r)s(r) from a position where the attention-directed projection data were acquired. The plus and minus signs of the γ(r)s(r) may be interchanged for each projection angle. The γ(r) may be a value close to ½k, not zero. The k may be a value from approximately 1 to 2.

(11) In the X-ray CT system as set forth in the above (1), in reconstructing an image with the reconstruction means, employing the projection data, an shifted focal position, defined as a position different in the Z-axis direction by a predetermined quantity from an actual focal position of the X-ray source when the projection data were acquired, may be set. An shifted detector element position, defined as a position different in the Z-axis direction by a predetermined quantity from an actual position of the detector element when the projection data were acquired, may be set. The reconstruction means may perform back projection along a plane connecting the shifted focal position and each row of shifted detector element positions.

(12) In the X-ray CT system as set forth in the above (11), the focal position of the X-ray source may be constructed such that it is alternately movable on plus and minus sides in the Z-axis direction for each of the rotational angles. Projection data that are acquired at either position of the alternate movements of the focus may be arranged with a sampling pitch $s_{iso}$ in the Z-axis direction at the rotation center axis. Planes connecting the alternate movement positions of the focus and each row of the detector elements of the detector, at the rotation center axis, may be shifted to be respectively away by $α_{iso}$ (positive value) times $s_{iso}$ from a position at the rotation center axis of arrangement of projection data obtained when the focus is at a middle point between the alternate focal positions. The shifted focal position may be approximately $±[(k−2)R_{FD}/k(R_{FD}−R_F)]α_{iso}s_{iso}$. The shifted detector element position may be a position away from a true detector element position by approximately $±(½k) (R_{FD}/R_F) s_{iso}$. The plus and minus of the shifted focal position and shifted detector element position may be interchanged and employed with the plus and minus in a Z-axis direction position of the focus when the projection data were acquired. The RFD may sphereistance from the middle point of the alternate movements of the focus to a detector plane, and the $R_F$ may sphereistance from the middle point of the alternate movements of the focus to the rotation center. The k may be a value neither zero nor infinity.

(13) The X-ray CT system as set forth in the above (12), the k is preferably a value from approximately 1 to 2.

(14) In the X-ray CT system as set forth in the above (1), in reconstructing an image with the reconstruction means, employing the projection data, either or both of (1) an shifted focal position, defined as a position different in the Z-axis direction by a predetermined quantity from an actual focal position of the X-ray source when the projection data were acquired, and (2) an shifted detector element position, defined as a position different in the Z-axis direction by a predetermined quantity from an actual position of the detector element when the projection data were acquired, may be set. When both of the shifted focal position and shifted detector element position are set, back projection may be performed along a plane connecting the shifted focal position and each row of shifted detector element positions. When either the shifted focal position or the shifted detector element position is set, back projection may be performed along a plane connecting a true focal position or the shifted focal position and the shifted detector element position or each row of true detector element positions.

(15) In the X-ray CT system as set forth in the above (1), a helical scan may be performed. In back projecting the projection data, the projection data may be used so that a position at which the projection data are back projected is different in the Z-axis direction from a path where the projection data were acquired. In shifting the position in the Z-axis direction, one of two set of projection data in an opposed relationship may be shifted on a plus side in the Z-axis direction, and the other may be shifted on a minus side in the Z-axis direction.

(16) In an X-ray computed tomography (CT) system which comprises (a) an X-ray source for radiating X-rays, (b) an X-ray detector disposed opposite to the X-ray source with a predetermined rotation center axis therebetween, and comprising a plurality of detector elements arranged two-dimensionally in a Z-axis direction, which is a direction along the rotation center axis, and a direction crossing the Z-axis direction, and (c) a data acquisition unit for acquiring X-ray detection data detected by the plurality of detector elements of the detector, and wherein the data acquisition unit is caused to acquire the X-ray detection data detected by the detector by radiating X-rays from the X-ray source at each of rotational angles, while causing the X-ray source and the detector to rotate around the rotation center axis, and wherein an image is reconstructed based on two-dimensional projection data obtained by processing the acquired X-ray detection data, the image reconstruction method of the present invention comprises a step of performing an arithmetic operation, in which the two-dimensional projection data are back projected along a second path different in the Z-axis direction from a first path of X-rays at the time of the detection, to reconstruct an image.

(17) In the image reconstruction method as set forth in the above (16), the X-ray CT system may perform a helical scan. When reconstructing the image, in back projecting the projection data, the projection data may be used so that a position at which the projection data are back projected is different in the Z-axis direction from a path where the projection data were acquired. One of two set of projection data in an opposed relationship may be shifted on a plus side in the Z-axis direction, and the other may be shifted on a minus side in the Z-axis direction.

(18) An X-ray CT system of the present invention may comprise an X-ray source for radiating X-rays; an X-ray detector having a plurality of detector elements arranged two-dimensionally, and disposed opposite to the X-ray source with a predetermined rotation center axis therebetween; and reconstruction means for performing an arithmetic operation, in which two-dimensional projection data obtained based on X-ray detection data detected by the detector elements while rotating the X-ray source around the rotation center axis are back projected along a second path different in a Z-axis direction extending along the rotation center axis from a first path of X-rays at the time of the detection, to reconstruct an image.

(19) An image reconstruction method for an X-ray CT system of the present invention may comprise a scan step of causing an X-ray source for radiating X-rays to rotate around a predetermined rotation center axis with an X-ray detector, which has a plurality of detector elements arranged two-dimensionally, disposed opposite to the X-ray source with the predetermined rotation center axis therebetween; and an image reconstruction step of performing an arithmetic operation, in which the two-dimensional projection data obtained based on a detection result of the detector elements in the scan process are back projected along a second path different in a Z-axis direction extending along the rotation center axis from a first path of X-rays at the time of the detection, to reconstruct an image.

(20) An image reconstruction program of the present invention is used for executing an image reconstruction method for an X-ray CT system by being read into and executed by a computer. The program may cause the computer to execute a scan step of causing an X-ray source for radiating X-rays to rotate around a predetermined rotation center axis with an X-ray detector, which has a plurality of detector elements arranged two-dimensionally, disposed opposite to the X-ray source with the predetermined rotation center axis therebetween; and an image reconstruction step of performing an arithmetic operation, in which the two-dimensional projection data obtained based on a detection result of the detector elements in the scan process are back projected along a second path different in a Z-axis direction extending along the rotation center axis from a first path of X-rays at the time of the detection, to reconstruct an image.

(21) An X-ray CT system of the present invention may comprise (a) an X-ray source for radiating X-rays; (b) an X-ray detector disposed opposite to the X-ray source with a predetermined rotation center axis therebetween, and comprising a plurality of detector elements arranged two-dimensionally in a Z-axis direction, which is a direction along the rotation center axis, and a direction crossing the Z-axis direction; (c) a data acquisition unit for acquiring X-ray detection data detected by the plurality of detector elements of the detector; (d) helical scan means for causing the data acquisition unit to acquire the X-ray detection data detected by the detector by radiating X-rays from the X-ray source at each of rotational angles, while causing the X-ray source and the detector to rotate around the rotation center axis and also move in the Z-axis direction relatively with respect to a subject for CT examination located between the X-ray source and the detector; (e) means for moving a focal position of the X-ray source alternately on plus and minus sides in the Z-axis direction for each of the rotational angles; and (f) reconstruction means for performing an arithmetic operation, in which two-dimensional projection data obtained by processing the X-ray detection data acquired are back projected along a second path different in the Z-axis direction from a first path of X-rays at the time of the detection, to reconstruct an image. In back projecting with the reconstruction means projection data acquired at the alternate positions of the focus of the X-ray source, a distance away from the rotation center axis toward the focus is represented by r. At a position of the r, when attention is directed to projection data which passed the vicinity of the rotation center axis, a Z-axis direction arrangement pitch s of the attention-directed projection data is expressed as a function s(r) of the r, and a Z-axis direction position of the attention-directed projection data is expressed as being away by $\alpha(r)s(r)$ from a Z-axis direction position of arrangement of projection data obtained when the focus is at a middle point between the alternate focal positions. A position, at which the attention-directed projection data are back projected, may be away by $\gamma(r)s(r)$ from the Z-axis direction position at the r of arrangement of the projection data obtained when the focus is at the middle point between the alternate focal positions. The $\gamma(r)$ may be significantly different from the $\alpha(r)$ and is a value closer to $\alpha(r)+[1-4\alpha(r)]/2k$ than the $\alpha(r)$, and the k may be a value from approximately 1 to 2.

Advantages of the Invention

According to the present invention, at least the following effects and advantages are obtainable.

That is, an image is reconstructed by performing an arithmetical operation in which two dimensional projection data, obtained based on X-ray data detected with the detector elements while rotating the X-ray detecting system around the rotation center axis (Z-axis) is back projected along a path different in the Z-axis direction from the X-ray path of the projection data. Therefore, the present invention is able to mathematically overcome or reduce the problem caused by non-equidistant sampling intervals at the time of projection data acquisition, and more effectively suppress artifacts (false image components or abnormal patterns) of a reconstructed image, particularly abnormal patterns called windmill artifacts, than prior art. As a result, it becomes possible to obtain higher definition image (reconstructed image), reduce the possibility of an erroneous diagnosis and clinical difficulty due to abnormal patterns, and greatly shorten inspection time. This makes a considerable contribution to an enhancement in the value of CT diagnosis.

BRIEF DESCRIPTION OF THE DRAWINGS

FIGS. 7(a) and 7(c) are diagrams of clinical image examples illustrating the state in which windmill artifacts have occurred, and FIGS. 7(b) and 7(d) are diagrams of clinical image examples illustrating the state in which the windmill artifacts in FIGS. 7(a) and 7(c) have been suppressed;

DESCRIPTION OF REFERENCE NUMERALS

Figure 1:
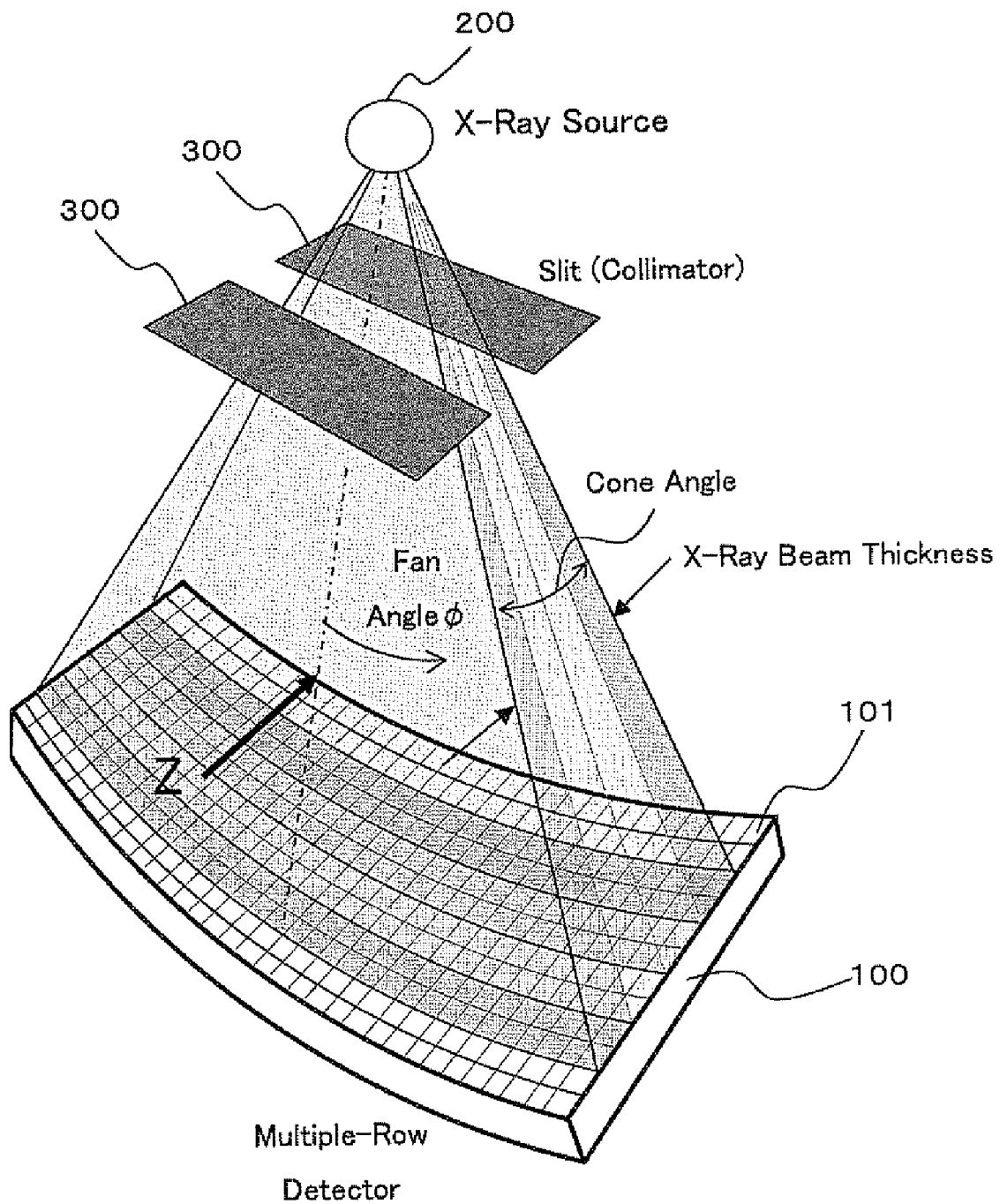
FIG. 1 is a schematic perspective view illustrating the configuration of the X-ray measuring system of the scanner of a multislice CT.
Figure 2:
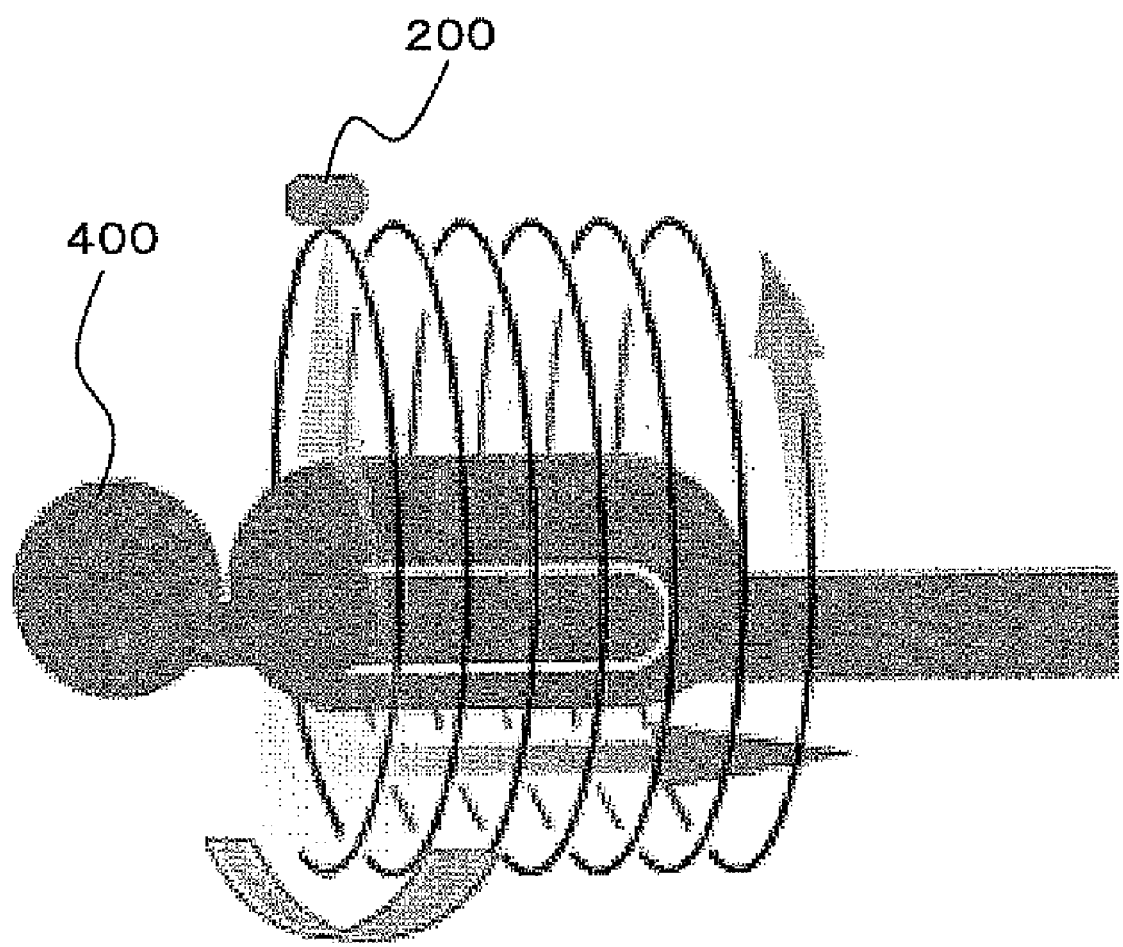
FIG. 2 is a schematic view for explaining a helical scan.

Tunnel-shaped diagnosis space
11 Scanner
12 X-ray tube (X-ray source, focus)
13 X-ray detector
14 DAS (data acquisition system)
Data transmitter
16 Scanner controller (scanning means)
20 Host computer (computer)
21 Interactive terminal
22 Display
23 First storage
24 Second storage
25 Image reconstruction unit (image reconstruction means)
25A, 35A Preprocessing section
25B, 35B Convolution-interpolation section
25C, 35C Back Projection section
25D, 35D Storage section
26 Bus
P Test subject

BEST MODES FOR CARRYING OUT THE INVENTION

Embodiments of the present invention will hereinafter be described with reference to the drawings. The present invention, however, is not limited to the following embodiments, but may be modified within the scope of the invention.

[A] Overview

In view of the problems found in prior art, the inventors of this application have approached windmill artifacts from viewpoints entirely different from prior art, and found an image reconstruction method that is capable of sufficiently suppressing windmill artifacts even when a sampling pitch obtained by adding odd and even views together is not half $s_{iso}$ at the center of rotation. This is able to suppress windmill artifacts throughout a wide field of vision.

According to this image reconstruction method, the focus flying width of the zFFS method can be made substantially smaller. In an extreme case, windmill artifact can be suppressed even if the flying width is zero, although compromise on the spatial resolution in Z-axis direction cannot be avoided in this case. Making the flying width small can keep the intersection position $r_{lim}$ of odd and even views sufficiently away from the center of rotation and solve the aforementioned problem (1) of the conventional zFFS method. In addition, making the flying width small can spontaneously solve or alleviate the aforementioned problems (2), (3), and (4) as well.

The first main point is that even if the zFFS method is employed, as described above, the focus flying width is made smaller than that used in the conventional zFFS method. In this case, a method for obtaining a sufficient effect is that (1) in the zFFS method the path of projection data from a focus onto a detector-element row has a certain inclination relative to the Z-axis for each of odd and even views, but in the image reconstruction method a back-projection process is performed at a different inclination from that inclination, and along a path shifted, in the Z-axis direction, and (2) an optimum path for the back-projection path can theoretically be obtained in accordance with a focus flying width.

The second main point, although it is described after a detailed description given in the case of employing the zFFS method, is that even if no zFFS method is employed, i.e., even in an ordinary scanning method in which there is no focus flying, in the image reconstruction method, projection data is back projected along an optimum path which is different in inclination and position in the Z-axis direction from the path where the projection data were actually obtained, for each of odd and even views.

The third main point, although it is described in "(C3) Overview 3 of Yet Another System Configuration and Operation" described later, is that in the case of adopting a method in which image reconstruction is performed employing both of projection data in an opposed relationship, each of both projection data is back projected along an optimum path which is different in position in the Z-axis direction from the path where the projection data were actually obtained.

First of all, a theory forming a basis will be described in the case of performing the zFFS method. The basic theory shown herein is very similar in mathematical basis to the basic theories illustrated in the aforementioned patent document 1 and non-patent document 6, but the present invention is entirely different from them. That is, patent document 1 and non-patent document 6, as previously described, disclose techniques for eliminating very small shower-shaped artifacts called aliasing artifacts by suitably handling data sampled at irregular intervals in an imaging plane, not in the Z-axis direction.

In contrast to this, the present invention employs the mathematical basis concept disclosed in patent document 1 and non-patent document 6, but is a novel technique for coping with different artifacts in a circumstance of quite a different kind. As described later, the following embodiments are also different essentially from patent document 1 and non-patent document 6. The following description begins with the mathematical basis.

Figure 9:
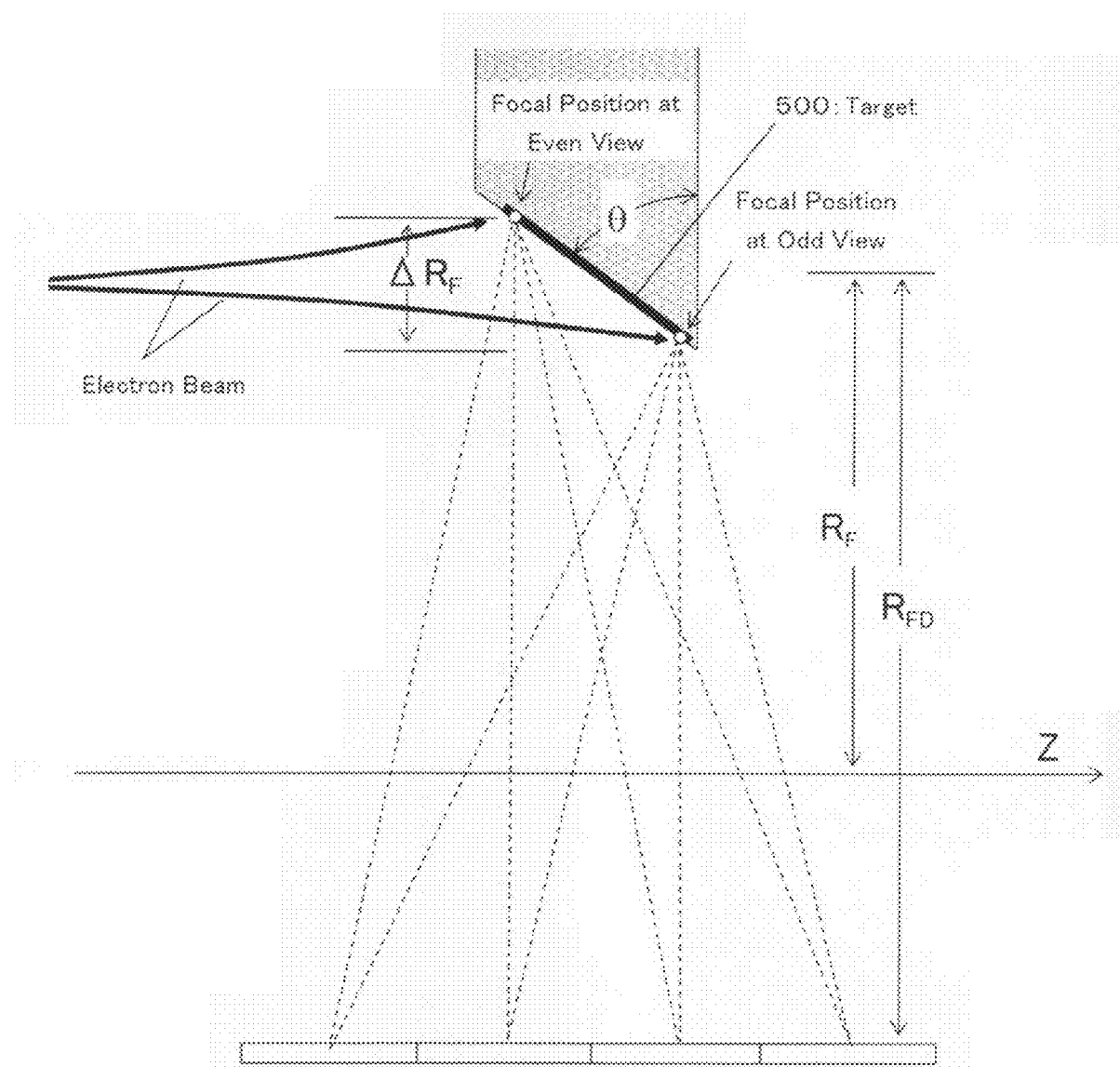
FIG. 9 is a diagram for explaining actual focal positions used in the zFFS method.

Here, neglect a swing $\Delta R_F$ in the r direction of a focus that occurs with the swing in the Z-axis direction of the focus, such as that described in FIG. 9. This is because $\Delta R_F$ is merely a complicating factor having no relation with the essence of the theory, and because as to a countermeasure to $\Delta R_F$, it is easy to incorporate into an image reconstruction calculation a parameter (i.e., $R_F$) indicating where the position in the radial direction of a focus is, for each view without any difficulty. In addition, the conventional zFFS method employs $\alpha_{iso}$ as a fixed quantity (¼), whereas the present invention handles it as an arbitrary value.

Before explaining in detail the theory, an outline of sampling conditions and basic concept will be given.

Figure 10:
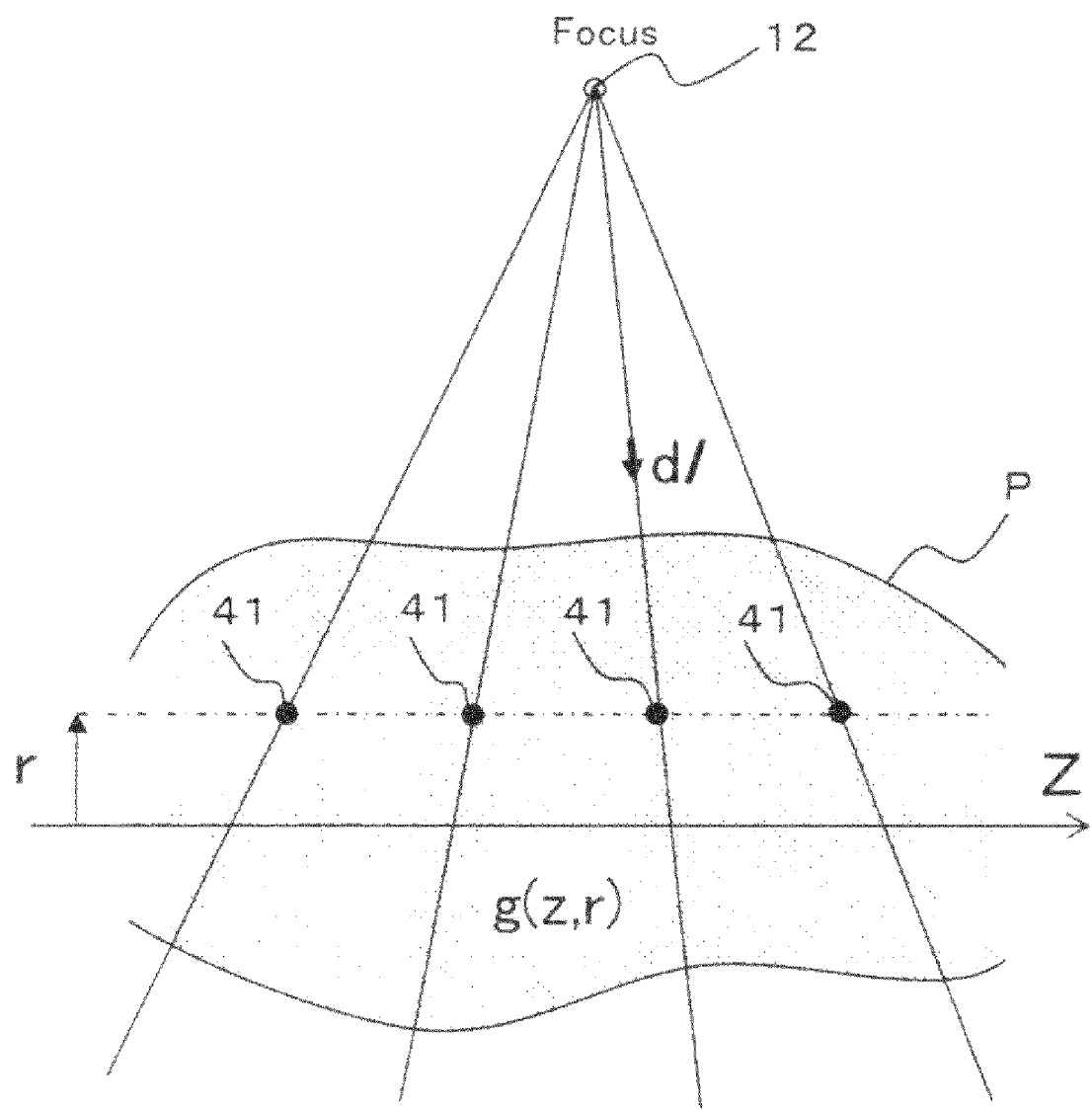
FIG. 10 is a diagram for explaining positions that measure a radiography subject in Z-axis direction at a given fan angle and at a given focal position in Z-axis direction.

For instance, as illustrated in FIG. 10, an X-ray source 12 and a test subject P are in a certain projection angle direction, and the X-ray attenuation coefficients of the test subject P are distributed as a function of Z-coordinates and a distance r from the Z-axis. Note that as the focal dimensions of the X-ray source 12 and aperture dimensions of a detector element are finite, the distribution of the X-ray attenuation coefficients is blurred slightly in the Z-axis direction and measured. Therefore, the distribution function of the X-ray attenuation coefficients is described as g (z, r), taking the blurring into account. The focus is assumed to have been shifted in the plus direction of the Z-axis.

Figure 13:
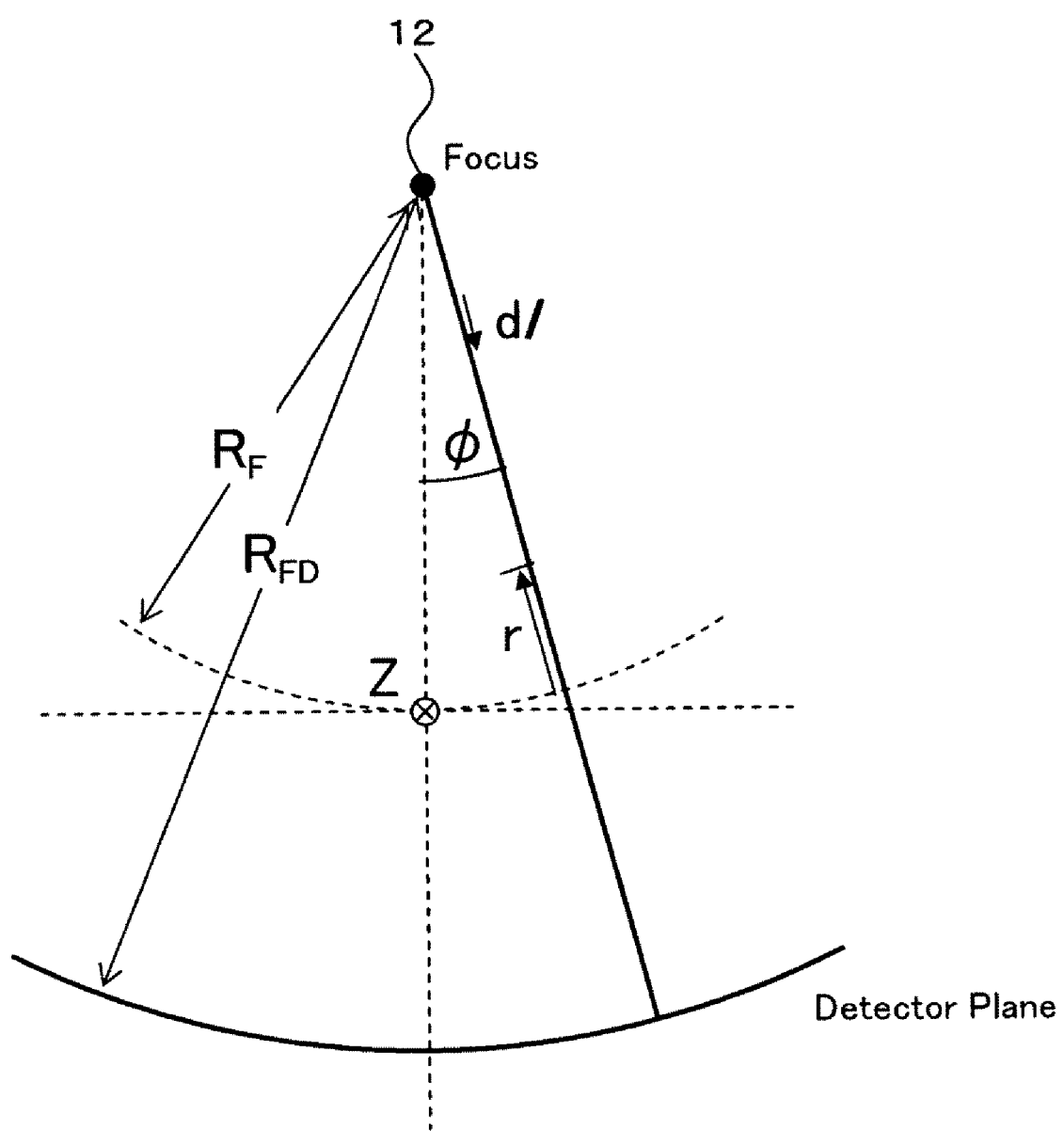
FIG. 13 is a diagram for explaining parameters, such as coordinates r and the like, at a certain fan angle.

Note that FIG. 10 illustrates a plane formed at a certain fan angle φ by the X-ray source (focus) 12 and the detector elements at the fan angle φ of the detector-element rows. This plane is equivalent to a heavy solid line illustrated in FIG. 13 when viewed from z=−∞. Assuming the position at a distance of R from the focus 12 of FIG. 13 to be zero (r=0), the positional coordinate from that position toward the focus is represented by r. $R_F$ is the distance between the focus 12 and the center of rotation, and $R_{FD}$ is the distance between the focus 12 and the detector plane.

Since the detector elements are discretely arranged in the Z-axis direction, paths for measuring the test subject P are also discrete. At a certain distance r, measurements are made at dispersed positions indicated by reference numerals 41 and 42 in FIGS. 10 to 12. Because the sampling pitch is finite, the dispersed measurements contain alias and are not the same as g(z, r). Therefore, an alias at each r is integrated and superimposed on projection data acquired by integrating g(z, r) along dl (unit vector from the focus 12 toward the detector) illustrated in FIG. 10.

Projection data are acquired through one rotation with such a measuring system. Assume that projection data acquisition is performed at infinitely fine angle intervals in the direction of rotation (i.e., the number of views per rotation is infinite). Assume also that the detector elements are arranged at infinitely fine intervals in the fan-angle (φ) direction as well. In such ideal conditions, even if images obtained by performing complete image reconstruction for all z-coordinates are arranged in the Z-axis direction, g(z, r) cannot be reproduced. What is obtained is g(z, r) containing alias superimposed thereon. It is known that, because a cone angle is not zero, in such a system, complete image reconstruction cannot be performed. However, since this problem is not related to the present invention, and for making a description of the present invention easy, it has been assumed that there is no cone angle problem.

Figure 11:
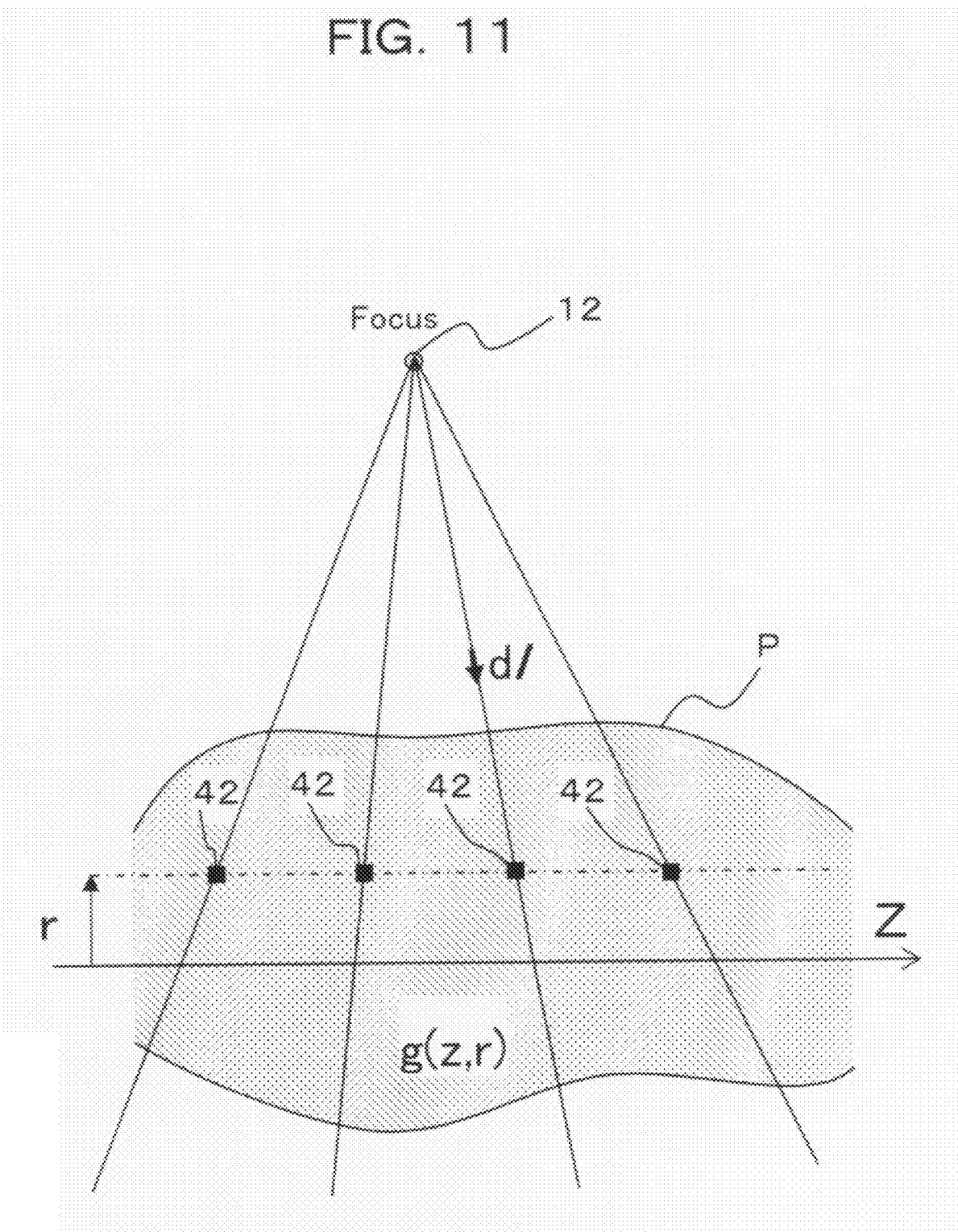
FIG. 11 is a diagram for explaining positions that measure (sample) a radiography subject at Z-axis positions different from the Z-axis positions of the focus illustrated in FIG. 10.

As illustrated in FIG. 11, assume that projection data are also obtained at the same projection angle for a different X-ray source position (focus 12). The measuring positions indicated with reference numerals 42 in FIG. 11 are different from those indicated with reference numerals 41 in FIG. 10, but even if image reconstruction is performed with these projection data, g(z, r) is not reproduced and the state in which g (z, r) containing alias superimposed thereon is reproduced remains unchanged. However, because the sampling positions are different from those in FIG. 10, the alias is not the same as those based on the measuring positions indicated with reference numerals 41 in FIG. 10.

Figure 12:
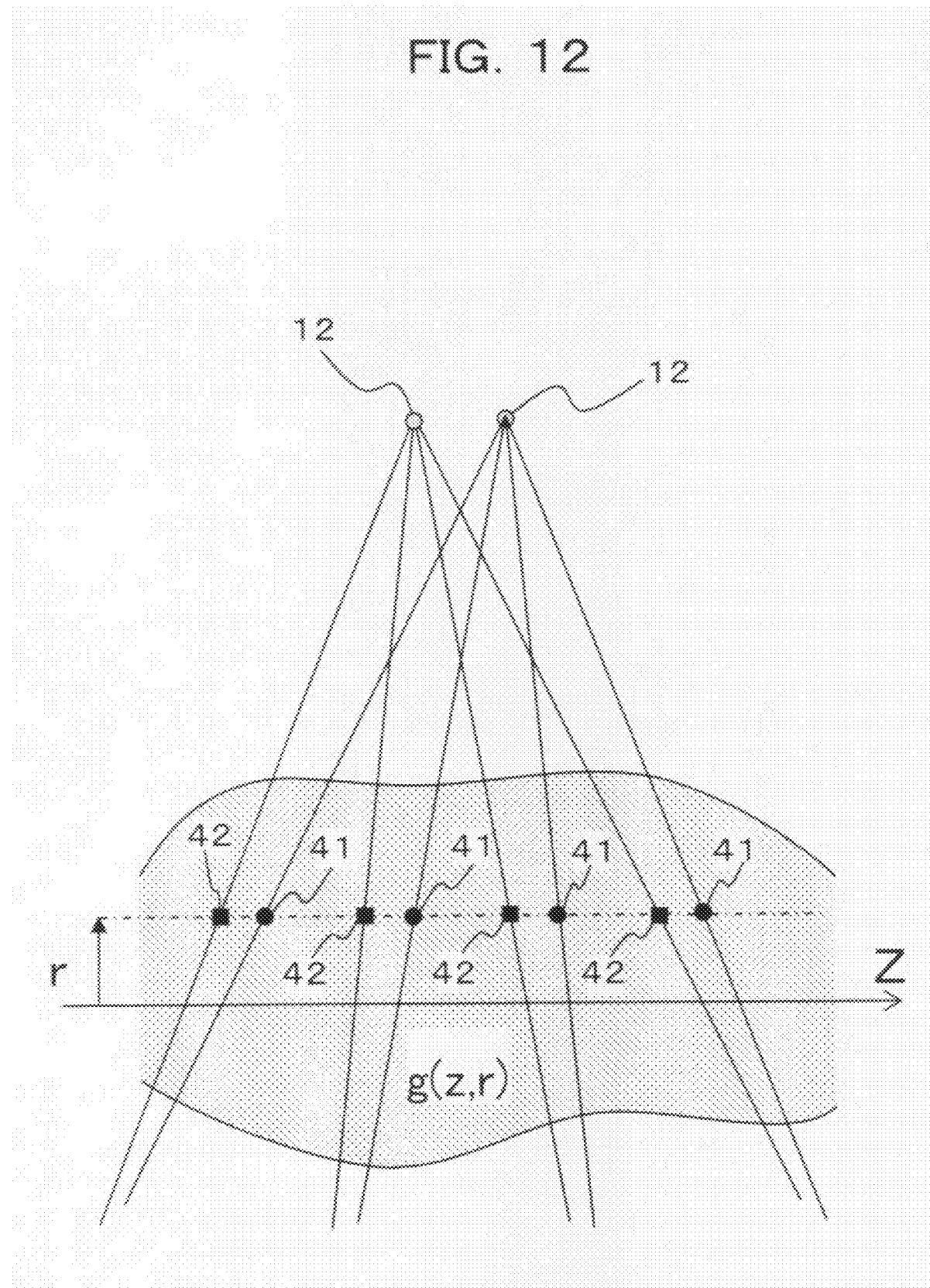
FIG. 12 is a diagram illustrating the sampling positions of FIGS. 10 and 11 added together.

If image reconstruction is performed employing both data obtained at the measuring positions indicated with reference numerals 41 and 42, the result is an average of a first image based on the positions indicated with reference numeral 41 and a second image based on the positions indicated with reference numeral 42 by linearity of image reconstruction calculations. The resultant image becomes better than the respective images because aliasing artifacts cancel more or less. This is equivalent to the idea that if the positions 42 and 41 are arranged, then the sampling pitches become fine as illustrated in FIG. 12 and therefore aliasing artifacts should be reduced.

In the present invention, the windmill artifact is judged as a manifestation of this aliasing artifact. As illustrated in FIG. 12, the positions 42 and 41 are distributing non-equidistantly. It is preferable that they distribute at equal intervals, but some intervals are wide due to inequality. In the present invention, it is judged that these unequal intervals have worsened the sampling problem. Therefore, the present invention illustrates how the respective projection data at positions 42 and 41 should be handled to minimize aliasing artifacts in the case of unequal Z-direction sampling pitches. The main point is that projection data are assumed to be acquired passing through positions different from the actual positions 42 or 41. That is, the present invention employs positions shifted from the actual positions 42 or 41.

Accurate theoretical investigations will hereinafter be given.

Figure 14:
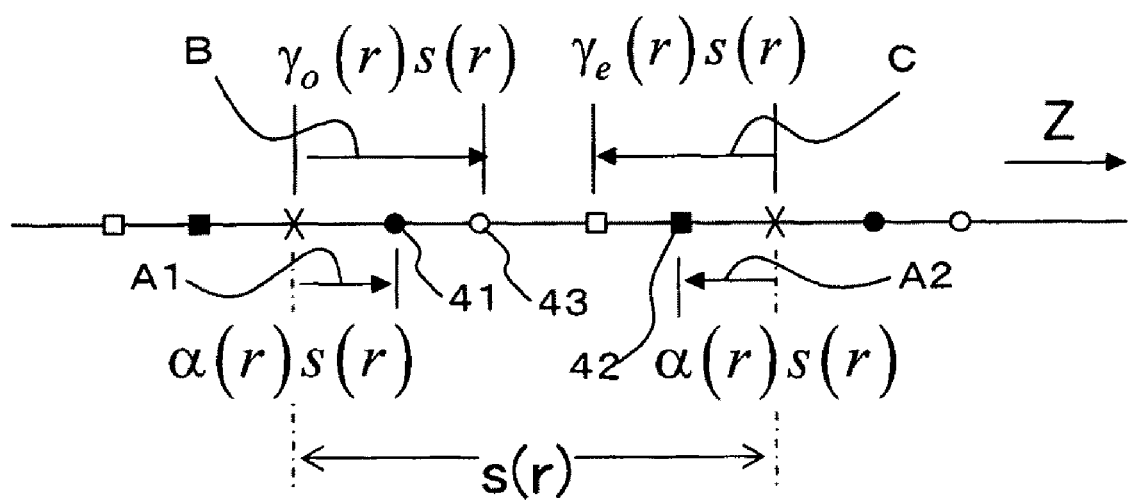
FIG. 14 is a diagram for explaining sampling positions and back projection positions in accordance with the theory of the present invention.

FIG. 14 is a diagram for explaining the position of the path of projection data at an arbitrary r, i.e., z-coordinates of a sampling position, and also explaining that the projection data are employed with shift in position. Assuming focal positions to be different between odd and even views, in comparison with the case of a sampling position (indicated with a mark of X) when a focus 12 is at the middle point, the path of a measuring X-ray is shifted by an arbitrary value αs [=α(r)s(r)] in the plus Z-axis direction for an odd view (see an arrow A1) to obtain projection data at position 41, and is also shifted by the arbitrary value αs in the minus Z-axis direction for an even view (see an arrow A2) to obtain projection data at position 42. Note that even if the positional relationship of plus and minus signs is reversed, the theory and results remain unchanged.

The projection data are relocated by being shifted respectively to arbitrary positions $\gamma_o(r)s(r)$ and $\gamma_e(r)s(r)$ indicated with reference numerals 43 and 44 (mark of ○ and mark of □) instead of the original positions 41 and 42 (see arrows B and C). As described later, this relocation can be implemented primarily by adopting the back projection path that is different from the projection path.

Note that s denotes a positive value, and if direction is determined as illustrated in FIG. 14, α is also a positive value. α, s, and γ are a function of r[α(r), s(r), and γ(r)], but in order to simplify the following equations, they are expressed simply as α, s, and γ by omitting r from them.

The X-ray attenuation coefficients of the test subject P are distributed as a certain function along the Z-axis direction at r. The function is unknown, but a function, which is obtained together with blurs due to the focus dimensions of the X-ray source and aperture dimensions of the detector element by making measurements at infinitely fine sampling intervals, is g(z). And the Fourier transformation of g(z) is expressed as G(f), as illustrated in the following Eq. 1. In this equation, F denotes Fourier transformation.

[Formula 1]

$$G(f) = F[g(z)] \quad (1)$$

A function $g_o(z)$ obtained by sampling g(z) for an odd view, and a function $g_e(z)$ obtained by sampling g(z) for an even view, can be expressed like the following Eqs. 2 and 3.

[Formula 2]

$$g_o(z) = g(z)\frac{1}{s}III\left(\frac{z-\alpha s}{s}\right) \quad (2)$$

$$g_e(z) = g(z)\frac{1}{s}III\left(\frac{z+\alpha s}{s}\right) \quad (3)$$

In these Eqs. 2 and 3, III is a Shah function like the following Eq. 4. In this equation, δ represents a Dirac's δ-function.

[Formula 3]

$$III(z) = \sum_{n=-\infty}^{\infty} \delta(z-n) \quad (4)$$

If the Fourier transformation of $g_o(z)$ and $g_e(z)$ are represented by $G_o(f)$ and $G_e(f)$ respectively, they are given by the following Eqs. 5 and 6 where * represents a convolution operation.

[Formula 4]

$$G_o(f) = G(f) * \{III(sf)e^{-i2\pi f\alpha s}\} \quad (5)$$

$$G_e(f) = G(f) * \{III(sf)e^{+i2\pi f\alpha s}\} \quad (6)$$

If $g_o(z)$ and $g_e(z)$ are respectively shifted like FIG. 10 by $\gamma_o$s and $\gamma_e$s, the resultant functions $g_{os}(z)$ and $g_{es}(z)$ and respective Fourier transformations $G_{os}(f)$ and $G_{es}(f)$ can be expressed like the following Eqs. 7, 8, 9, and 10.

[Formula 5]

$$g_{os}(z) = g_o(z-(\gamma_o s - \alpha s)) \quad (7)$$

$$g_{es}(z) = g_e(z+(\gamma_e s - \alpha s)) \quad (8)$$

$$G_{os}(f) = F[g_o(z-(\gamma_o s-\alpha s))] = \{G(f) * \{III(sf)e^{-i2\pi f\alpha s}\}\}e^{-i2\pi f(\gamma_o s-\alpha s)} \quad (9)$$

$$G_{es}(f) = F[g_e(z+(\gamma_e s-\alpha s))] = \{G(f) * \{III(sf)e^{+i2\pi f\alpha s}\}\}e^{+i2\pi f(\gamma_e s-\alpha s)} \quad (10)$$

Considering that g(z) already has a blur element and therefore has a band limitation to some degree, i.e., considering that G(f) hardly has a frequency component significantly exceeding a Nyquist frequency $f_N = \frac{1}{2}s$, the Fourier transformation of the aforementioned Eq. 9 can be approximated like the following Eq. 11.

[Formula 6]

$$G_{os}(f) = \{G(f) * (III(sf)e^{-i2\pi f\alpha s})\}e^{-i2\pi fs(\gamma_o-\alpha)} \quad (11)$$

$$\approx \left\{G(f) * \left\{\left(\frac{1}{s}\delta\left(f-\frac{1}{s}\right) + \frac{1}{s}\delta(f) + \frac{1}{s}\delta\left(f+\frac{1}{s}\right)\right)e^{-i2\pi f\alpha s}\right\}\right\}e^{-i2\pi fs(\gamma_o-\alpha)}$$

$$= \frac{e^{-i2\pi fs(\gamma_o-\alpha)}}{s}\left\{G(f) * \left(\delta\left(f-\frac{1}{s}\right)e^{-i2\pi\alpha} + \delta(f) + \delta\left(f+\frac{1}{s}\right)e^{+i2\pi\alpha}\right)\right\}$$

$$= \frac{e^{-i2\pi fs(\gamma_o-\alpha)}}{s}\left\{G\left(f-\frac{1}{s}\right)e^{-i2\pi\alpha} + G(f) + G\left(f+\frac{1}{s}\right)e^{+i2\pi\alpha}\right\}$$

Similarly, the Fourier transformation of the aforementioned Eq. 10 can be approximated like the following Eq. 12.

[Formula 7]

$$G_{es}(f) \approx \frac{e^{+i2\pi fs(\gamma_e - \alpha)}}{s}\left\{G\left(f - \frac{1}{s}\right)e^{+i2\pi\alpha} + G(f) + G\left(f + \frac{1}{s}\right)e^{-i2\pi\alpha}\right\} \quad (12)$$

The Fourier transformation of sampled data comprising both $g_{os}(z)$ and $g_{es}(z)$ is given by the following Eq. 13.

[Formula 8]

$$\begin{aligned}G_{sumS}(f) &= F[g_{oS}(z) + g_{eS}(z)] \quad (13) \\ &\approx G\left(f - \frac{1}{s}\right)\frac{1}{s}(e^{-i2\pi fs(\gamma_o - \alpha)}e^{-i2\pi\alpha} + \\ & e^{+i2\pi fs(\gamma_e - \alpha)}e^{+i2\pi\alpha}) + G(f)\frac{1}{s}(e^{-i2\pi fs(\gamma_o - \alpha)} + \\ & e^{+i2\pi fs(\gamma_e - \alpha)}) + G\left(f + \frac{1}{s}\right)\frac{1}{s}(e^{-i2\pi fs(\gamma_o - \alpha)}e^{+i2\pi\alpha} + \\ & e^{+i2\pi fs(\gamma_e - \alpha)}e^{-i2\pi\alpha})\end{aligned}$$

The first and third terms of Eq. 13 represent aliasing components, while the second term represents a true spectral component. The three terms have modifying terms, respectively. Directing attention to the modifying terms, they are different between the aliasing and true spectral terms. Using this fact, aliasing components can be effectively suppressed without reducing the true spectral component too much by selection of $\gamma_o$ and $\gamma_e$.

Directing attention to the second term of Eq. 13, it is found that unless $\gamma_o = \gamma_e$, an imaginary number term occurs. This means that a profile will shift in the Z-axis direction, so it should be avoided. Therefore, with $\gamma_o = \gamma_e = \gamma_o$, the following Eq. 14 is obtained.

[Formula 9]

$$G_{sumS}(f) = \frac{2}{s}\left\{G\left(f - \frac{1}{s}\right)A_1 + G(f)A_0 + G\left(f + \frac{1}{s}\right)A_{-1}\right\} \quad (14)$$

$$A_1 = \cos(2\pi fs(\gamma - \alpha) + 2\pi\alpha)$$
$$A_0 = \cos(2\pi fs(\gamma - \alpha))$$
$$A_{-1} = \cos(2\pi fs(\gamma - \alpha) - 2\pi\alpha)$$

For aliasing-artifact suppression, it is preferable that $A_1$ and $A_{-1}$ in the above Eq. 14 be near to zero over a frequency band which is as wide as possible, but since values near to zero cannot be acquired over the whole region, what is important is at which frequency they are brought near to zero. The Nyquist frequency $f_N$ is given by the following Eq. 15.

[Formula 10]

$$f_N = \frac{1}{2s} \quad (15)$$

Since G(f) is band-limited to some extent the component, which extends up to a negative frequency band, of alias extending from a positive high frequency side is guaranteed to be originally small. As illustrated in the aforementioned Eq. 14, $A_1$ represents a frequency transfer function for alias extending from the high frequency side, so $A_1$ should be in the vicinity of zero at positive frequencies. Because G(f) is limited in band to some degree, the magnitude of G(f) must monotonously reduce in broad aspects with respect to the absolute value of frequency f, and consequently, components turning back as alias must be great in the vicinity of the Nyquist frequency.

Therefore, it is desirable for $A_1$ to be very close to zero in the vicinity of $f=f_N$. Likewise, it is desirable for $A_{-1}$ to be very close to zero in the vicinity of $f=-f_N$. Whether making $A_1$ and $A_{-1}$ zero accurately at positive and negative Nyquist frequencies is optimum is in an issue of trade-off with compromise on $A_0$, therefore, without fixing at zero, the following Eq. 16 is solved so that the transfer functions of alias are made zero at frequencies which are k times positive and negative Nyquist frequencies.

[Formula 11]

$$A_1(kf_N) = 0, A_{-1}(-kf_N) = 0 \quad (16)$$

or $$\cos\left(2\pi k \frac{1}{2s}(\gamma s - \alpha s) + 2\pi\alpha\right) = 0,$$

$$\cos\left(-2\pi k \frac{1}{2s}(\gamma s - \alpha s) + 2\pi\alpha\right) = 0$$

From both conditions, two solutions are obtained like Eq. 17.

[Formula 12]

$$\gamma = \alpha - \frac{1 + 4\alpha}{2k}, \alpha + \frac{1 - 4\alpha}{2k} \quad (17)$$

In order to maintain spatial resolution in the Z-axis direction, $A_o$ is desired to be maintained at a value close to 1 for frequencies as high as possible, and consequently, it is desirable that the absolute value of $\gamma - \alpha$ be small. What satisfies this is the following Eq. 18 which is one of the two solutions expressed by Eq. 17, because both $\alpha$ and k are a positive value.

[Formula 13]

$$\gamma = \alpha + \frac{1 - 4\alpha}{2k} \quad (18)$$

For example, when $\alpha = 0.25$ (which is an ideal sampling condition according to the zFFS method), $\gamma$ is equal to $\alpha$ regardless of k. At this time, $A_o$ is 1 independently of frequency, and $A_1$ and $A_{-1}$ are zero. That is to say, when $\alpha = 0.25$, projection data are arranged at equal intervals in the Z-axis direction. In this case, according to prior art, it is sufficient if projection data are back projected toward the position where the projection data were acquired.

However, even when $\alpha_{iso}$ is set at 0.25, $\alpha$ is not 0.25 except the center of rotation, and projection data distribute with unequal intervals (unequal pitches) in the Z-axis direction and are in a non-ideal sampling condition. It is undesirable that projection data be back projected along the path of the projection data except the center of rotation. In this case, Eq. 18 shows what to do.

Figure 15:
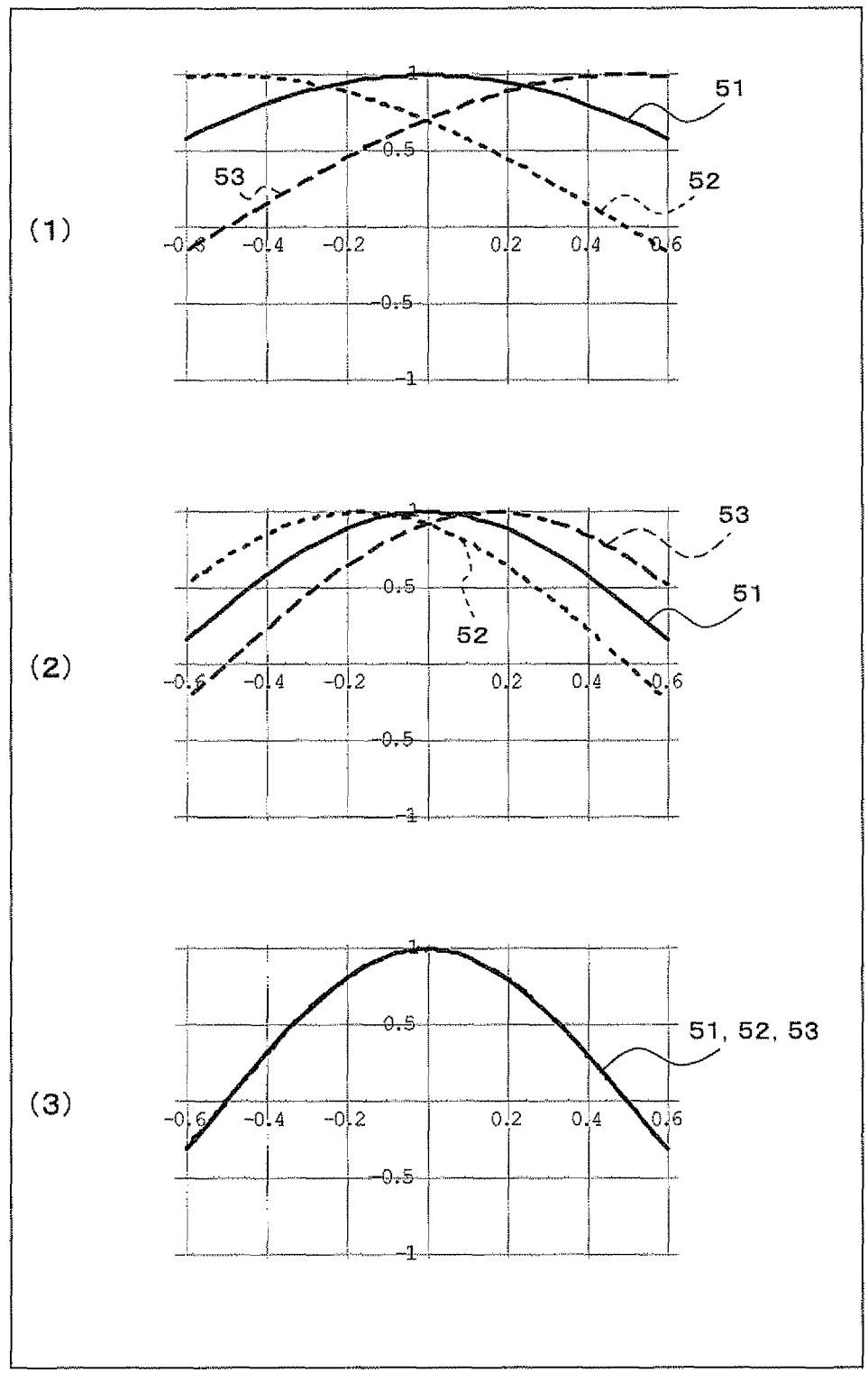
FIG. 15 is a graph illustrating a relationship between frequency transfer functions for aliased spectra and a true spectrum.

Examples of non-ideal sampling conditions are illustrated in FIG. 15. In the figure, a solid line 51 represents a frequency transfer function ($A_0$) for a true spectrum, a dashed line 52 an alias transfer function for a positive frequency band ($A_1$), and a broken line 53 an alias transfer function for a negative frequency band ($A_{-1}$). With s=1, the horizontal axis of 0.5 represents the Nyquist frequency.

For instance, if k is set at 1 ($\gamma$=0.3750) in the state of $\alpha$=0.125, a graph illustrated in FIG. 15(1) is obtained. That is, alias from the positive frequency side (alias transfer function for positive frequency band ($A_1$) indicated with a dashed line 52) is significantly suppressed to approximately zero in the vicinity of the positive Nyquist frequency, and aliasing artifacts from the negative frequency side (alias transfer function for negative frequency band ($A_{-1}$) indicated with a broken line 53) are significantly suppressed to approximately zero in the vicinity of the negative Nyquist frequency. On the other hand, a true spectrum (frequency transfer function $A_0$ indicated with a solid line 51) is only suppressed to about 30% in the vicinity of respective Nyquist frequencies.

Even if $\alpha$ is an even smaller value [e.g. 0.0625 (k=1 and $\gamma$=0.4375)], as illustrated in FIG. 15(2), alias is more suppressed than a true spectrum. When the swing of a focus is zero ($\alpha$=0), as illustrated in FIG. 15(3), it is found that there is no effect of selective suppression of either aliased spectrum or the true spectrum and both are suppressed equally.

The parameter $\alpha$ varies depending upon r, but if $\gamma$ is selected in accordance with $\alpha$, as described above, there is an effect of concentratedly suppressing an aliasing-artifact component at an arbitrary frequency $k \cdot f_N$ as long as $\alpha$ is not zero. Probably, when $k \approx 1$, the aliasing-artifact suppressing effect will become maximum.

The basic theory has been described with the zFFS method as an example. This can be a little more generally expressed as follows.

There is a set-A of projection data, and there is also a set-B of another projection data. The pitches of both the set-A and set-B are represented by s. If the projection data set-A and projection data set-B are adjacent to each other when they are arranged, a middle point is taken therebetween, and the projection data set-A and projection data set-B at distances of $\alpha$s away from the middle point need to be used by being shifted by the value of the following Eq. 19 in a direction of $\alpha$. It is necessary that if this value is negative, the data set be used by returning the data set from the position of $\alpha$s toward the middle point by that amount.

[Formula 14]

$$\gamma s - \alpha s = s \frac{1 - 4\alpha}{2k} \quad (19)$$

As set forth above, it is found that if data sampled at the position of $\alpha$s are employed by being shifted to the position of $\gamma$s differing from that position, aliased spectra can be effectively suppressed while maintaining the compromise on the true spectrum minor. As set forth later, this actually suppresses windmill artifacts and does not cause significant blurs in the Z-axis direction.

[B] Specific Examples

A description will be given of a specific means for easily executing that in image reconstruction calculation, data sampled at the position of $\alpha$s are employed by being shifted to the position of $\gamma$s differing from that position.

Figure 6:
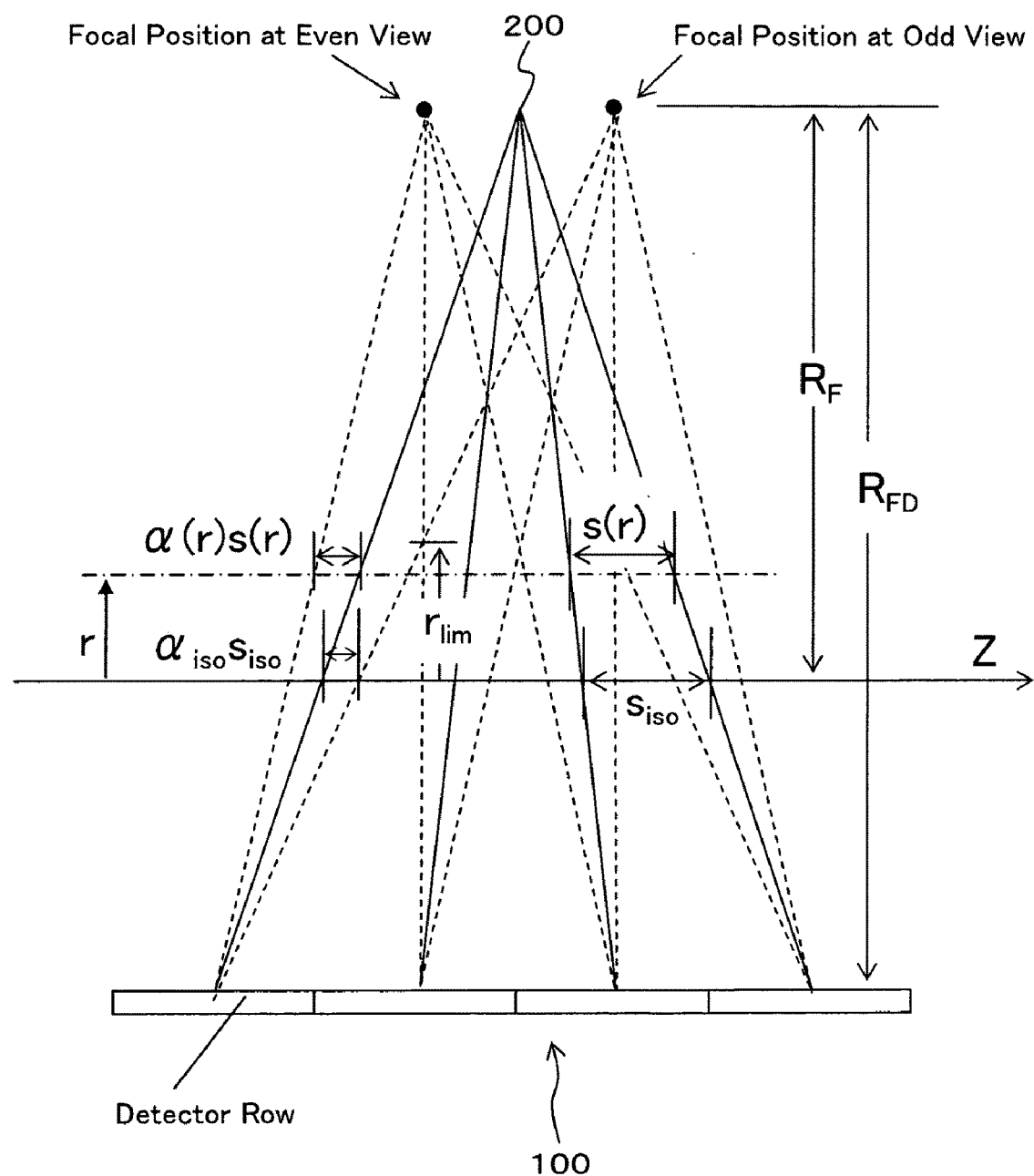
FIG. 6 is a diagram for explaining the zFFS method.

With geometry illustrated in FIG. 6, Eqs. 20 and 21 are readily derived. Note in the following description that r-coordinates are explicitly expressed into equations.

[Formula 15]

$$s(r) = s_{iso} \frac{R_F - r}{R_F} \quad (20)$$

$$\alpha(r)s(r) = \alpha_{iso} s_{iso} \left(1 + \frac{r}{R_{FD} - R_F}\right) \quad (21)$$

These Eqs. 20 and 21 give the following Eq. 22.

[Formula 16]

$$\alpha(r) = \alpha_{iso} \frac{R_F}{R_F - r}\left(1 + \frac{r}{R_{FD} - R_F}\right) \quad (22)$$

From the aforementioned Eqs. 18, 19, and 20, the following Eq. 23 is obtained as desirable $\gamma(r)s(r)$.

More specifically, compared with the sampling position when a focus 12 is at a middle point, data are considered to be acquired at a position shifted in the positive Z-axis direction by that value for an odd view, and at a position shifted in the negative Z-axis direction by that value for an even view.

[Formula 17]

$$\gamma(r)s(r) = \left(\alpha + \frac{1 - 4\alpha}{2k}\right)s_{iso}\frac{R_F - r}{R_F} \quad (23)$$

$$= \left(\alpha_{iso}\frac{R_F}{R_F - r}\left(1 + \frac{r}{R_{FD} - R_F}\right) + \right.$$

$$\left. \frac{1 - 4\alpha_{iso}\frac{R_F}{R_F - r}\left(1 + \frac{r}{R_{FD} - R_F}\right)}{2k}\right)s_{iso}\frac{R_F - r}{R_F}$$

$$= \frac{1}{2k}s_{iso}(1 + 2\alpha_{iso}(k - 2)) +$$

$$\frac{1}{2k}s_{iso}\frac{(1 + 2\alpha_{iso}(k - 2))R_F - R_{FD}}{R_F(R_{FD} - R_F)}r$$

This Eq. 23 indicates that if k is assumed to be a constant independent of place r, a position that is to be employed by assuming projection data to be there becomes a straight line with respect to r. That is, the equation means that projection data taken along a certain straight line should be handled as having been obtained along a different straight line (Eq. 23) from that. This line is a path in which projection data should be back projected. The present invention does not exclude that k is handled as a value depending on place r, but if k is a constant independent of r, a path for back projection becomes a straight line and therefore it becomes extremely easy for general image reconstruction systems to perform back projection along a straight path.

The reason the "line" is used is that a discussion is being conducted about the projection data relating to an arbitrary fan angle $\phi$ and also to one detector element of an arbitrary detector-element row. A large number of lines arranged in the fan angle $\phi$ for all rows of detector elements of the detector forms a plane. The number of planes corresponds to the number of intervals between fan angles. The essence of the present invention is how these planes are handled. The "line" is used solely for the purpose of making the theory easily understandable.

Eq. 23 will further be explained in a form that is easily understandable in execution. This is an easily understandable embodiment when reconstruction calculation is made easy by employing k as a constant independent of r. In Eq. 23, if $r=R_F$, the equation indicates the z coordinates of an imaginary focal position, and the image reconstruction is performed with the assumption that the focus is locating at that imaginary focal position. If $r=R_F-R_{FD}$, Eq. 23 indicates a required shift quantity in the Z-axis direction from a true position to an imaginary position for a detector row, and the image reconstruction is performed with the assumption that the detector row is locating at that imaginary position.

If an image reconstruction calculation is made assuming projection data to be obtained along a line connecting the imaginary focal position and imaginary detector row position, Eq. 23 is automatically satisfied for all r. It is easy for ordinary image reconstruction algorithms to use such imaginary positions of focus and detector row.

For odd views, an imaginary focal position $Z_{fo}$ and a shift quantity $Z_{do}$ for detector position are given by the following Eqs. 24 and 25.

[Formula 18]

$$Z_{fo} = \gamma(r)s(r)|_{r \to R_F} = \frac{(k-2)R_{FD}}{k(R_{FD}-R_F)}\alpha_{iso}s_{iso} \quad (24)$$

$$Z_{do} = \gamma(r)s(r)|_{r \to R_F - R_{FD}} = \frac{1}{2}\frac{R_{FD}}{R_F}s_{iso} \quad (25)$$

By shifting a focal point to be at the position of $Z_{fo}$, then using a position shifted by $Z_{do}$ from the position of a true detector-element row as the imaginary position of the detector-element row, and then assuming a plan connecting the imaginary focal position and imaginary detector-element row position to be a projection-data acquiring plane for the detector-element row, projection data is back projected along this plane. This can be very easily implemented by reconstruction systems that perform three-dimensional back projection.

In the image reconstruction calculation, there are several calculation steps. Similarly, it is preferable in these steps to perform processing, assuming an imaginary plane connecting an shifted imaginary focal position and a shifted imaginary detector row position to be a projection-data acquiring place for the detector row. However, in reconstruction systems that perform three-dimensional back projection, in steps other than back projection, even if projection data are handled at positions where the data were actually acquired, a great difference does not occur and there is no particular problem.

Similarly, for even views, an imaginary focal position $Z_{fe}$ and a required detector position shift quantity $Z_{de}$ are given by the following Eqs. 26 and 27.

[Formula 19]

$$Z_{fe} = -\gamma(r)s(r)|_{r \to R_F} = \frac{(k-2)R_{FD}}{k(R_{FD}-R_F)}\alpha_{iso}s_{iso} \quad (26)$$

$$Z_{de} = -\gamma(r)s(r)|_{r \to R_F - R_{FD}} = -\frac{1}{2k}\frac{R_{FD}}{R_F}s_{iso} \quad (27)$$

Figure 16A:
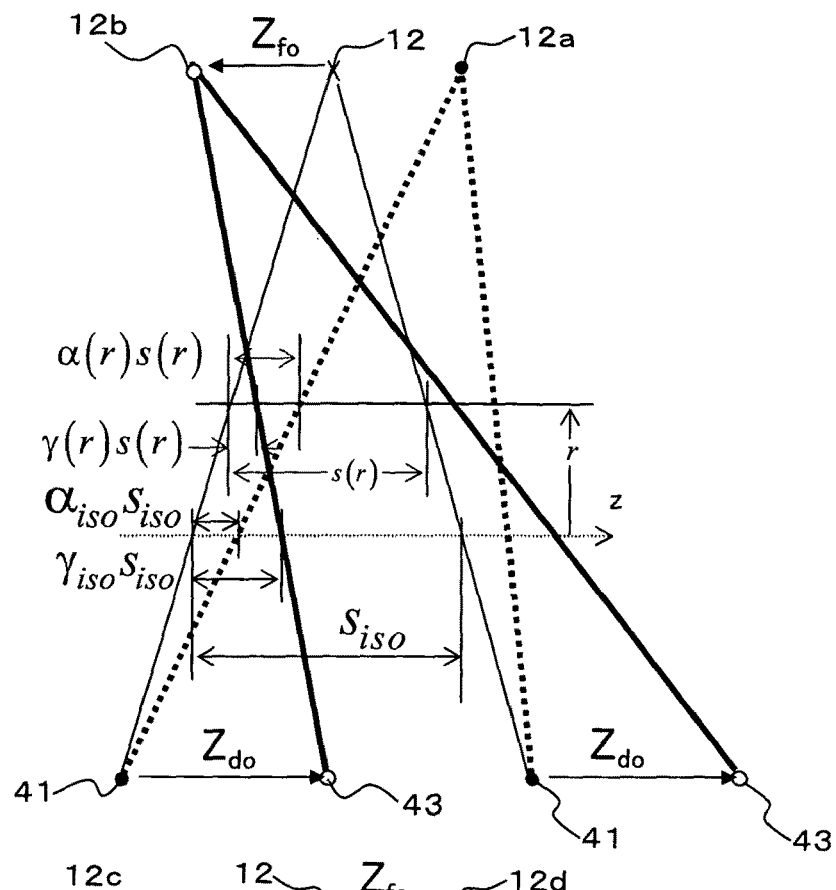
FIG. 16 is a diagram for explaining the shifted positions of projection data (case of k=1) according to the present invention, FIG. 16(a) being a diagram for explaining the shifted positions of projection data for an odd view, and FIG. 16(b) being a diagram for explaining the shifted positions of projection data for an even view.
Figure 16B:
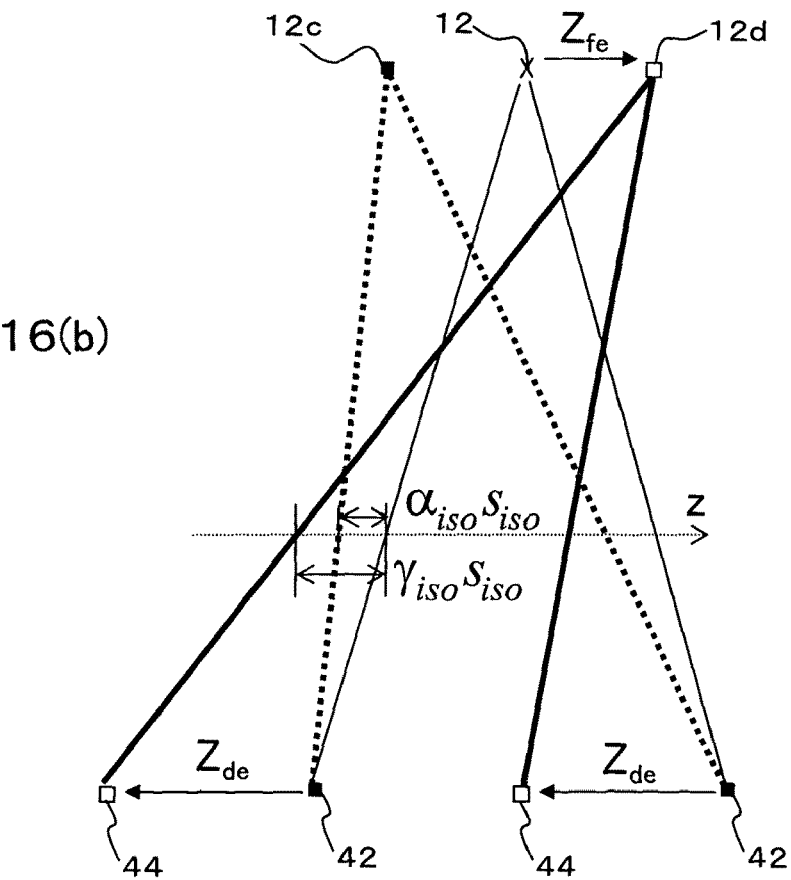

FIGS. 16(a) and 16(b) illustrate imaginary focal positions and detector position shift quantities for odd and even views. In this case, $\alpha_{iso}$ is made relatively small and k equals 1. In FIGS. 16(a) and 16(b), only two detector-element rows are illustrated. A light solid line represents a path for projection data when a focal point 12 is at a middle point (mark of X), a dotted line represents a path where projection data at a flown focal position were actually acquired, and a heavy solid line represents a path along which image reconstruction is performed assuming projection data to be at this position. Reference numeral 12a and reference numeral 41 (mark of ●) represent a focal position and a detector-element row position at which projection data were actually acquired for an odd view. Reference numeral 12b and reference numeral 43 (mark of ○) represent shifted positions at which an image reconstruction calculation is made assuming a focus 12 and a detector-element row to be for the odd view. Reference numeral 12c and reference numeral 42 (mark of ■) represent a focal position and a detector-element row position at which projection data were actually acquired for an even view, and reference numeral 12d and reference numeral 44 (mark of □) represent shifted positions at which an image reconstruction calculation is made assuming a focus 12 and a detector-element row to be there for the even view.

In the case of k=1, a focal position is assumed to be on a side opposite to a true flying position, and a detector position is shifted to be in the positive or negative direction of the Z-axis by half a pitch between rows. In the case where k is great, the imaginary positions of the detector element and focus 12 are handled as being closer to true positions.

Note that the phrase "imaginary position" is used solely for the purpose of making the present invention more understandable. Therefore, the present invention is able to be implemented in image reconstruction in various ways and does not necessarily need imaginary positions. In performing image reconstruction, the main point of the present invention resides in that in FIGS. 16(a) and 16(b), projection data acquired along a path indicated with a dotted line are back projected along a different path indicated with a heavy solid line.

Since it is difficult to grasp by formulae alone how much a value is shifted, specific numerical examples of $Z_{fo}$ and $Z_{do}$ will hereinafter be given. Assume that $R_F$=600 mm and $R_{FD}$=1072 mm (Because there is little difference among CTs, these values are used in the following description). A scan slice thickness $s_{iso}$ is 1 mm, so if the thickness $s_{iso}$ is X mm, values listed in Tables are increased X times. A suitable value for k is supposed to be 1 or so theoretically from the foregoing discussion, and even in simulation described later, an optimum value for k is 1 or so. It can be supposed from theory that when the value of k is far smaller than at least 1, blurring becomes significant in the Z-axis direction, while the effect of suppressing aliasing artifacts is reduced. Therefore, numerical values of $Z_{fo}$ and $Z_{do}$ in the case of k≧1 are listed in Tables 1 and 2

TABLE 1

| | $Z_{fo}$ [mm] | | | |
|---|---|---|---|---|
| | k = 1 | k = 1.5 | k = 2 | k = ∞ |
| $\alpha_{iso}$ = 0 | 0 | 0. | 0 | 0 |
| $\alpha_{iso}$ = 0.0625 | −0.142 | −0.047 | 0 | 0.142 |
| $\alpha_{iso}$ = 0.125 | −0.284 | −0.095 | 0 | 0.284 |
| $\alpha_{iso}$ = 0.250 | −0.567 | −0.189 | 0 | 0.567 |

In the conventional zFFS method, for odd views, a scan is performed when $\alpha_{iso}$=0.250, i.e., a scan is performed when focal position=+0.567, and image reconstruction is made when k=∞, i.e., when $Z_{fo}$=+0.567 mm. In the case of even views, the signs in the case of odd views become opposite.

TABLE 2

| | $Z_{d_o}$ [mm] | | |
|---|---|---|---|
| k = 1 | k = 1.5 | k = 2 | k = ∞ |
| 0.894 | 0.596 | 0.447 | 0 |

Note that the pitch in the Z-axis direction between detector-element rows is 1.787 mm at the detector position.

Before explaining specific embodiments, advantages of the reconstruction calculation according to the present invention will be again described briefly.

First, in the zFFS method, the effect is gradually reduced as r moves away from zero, and if r becomes greater than $r_{lim}$, no results are produced. In FIG. 6, $r_{lim}$ is r when projection data for odd and even views intersect each other. The geometry illustrated in FIG. 6 gives the following Eq. 28 easily.

[Formula 20]

$$r_{lim} = \frac{R_F(R_{FD} - R_F)(1 - 2\alpha_{iso})}{R_{FD} - R_F(1 - 2\alpha_{iso})} \quad (28)$$

In the conventional zFFS method $\alpha_{iso}$ is fixed at 0.25, but the present invention is able to suppress aliasing artifacts even when $\alpha_{iso}$ has an arbitrary quantity. Therefore, if $\alpha_{iso}$ is made small, $r_{lim}$ can be arbitrarily increased. In the conventional zFFS method where $\alpha_{iso}$=0.25, $r_{lim}$ is 183 mm, but from Eq. 28, $r_{lim}$ is 239 mm when $\alpha_{iso}$=0.200 and 341 mm when $\alpha_{iso}$=0.125. As the maximum radius of the visual field of CT is about 250 mm, the present invention can widen the effective radius of the zFFS method sufficiently. Therefore, if γ is selected as previously described, the effect of suppressing aliasing artifacts is sufficiently assured over the entire visual field. This makes it possible to solve the problem (1) found in the conventional zFFS method. This is illustrated by images described in the following embodiments.

What is particularly important is that $\alpha_{iso}$ is selected small. Therefore, the flying distance $\Delta R_F$ in the radial direction of a focus can be made small, whereby the problem (2) in the conventional zFFS method can be solved. In addition, as the flying distance in the Z-axis direction of a focus can be made small, the problem (3) in the conventional zFFS method is alleviated.

Furthermore, the alleviation of the problem (4) in the conventional zFFS method is illustrated and explained by images described in the following embodiments.

The resultant images and data by specific embodiments will hereinafter be given. These are results obtained by performing a simulation scan to reconstruct an image, when scan slice thickness $s_{iso}$=1 mm.

(B1) First Embodiment

Figure 17:
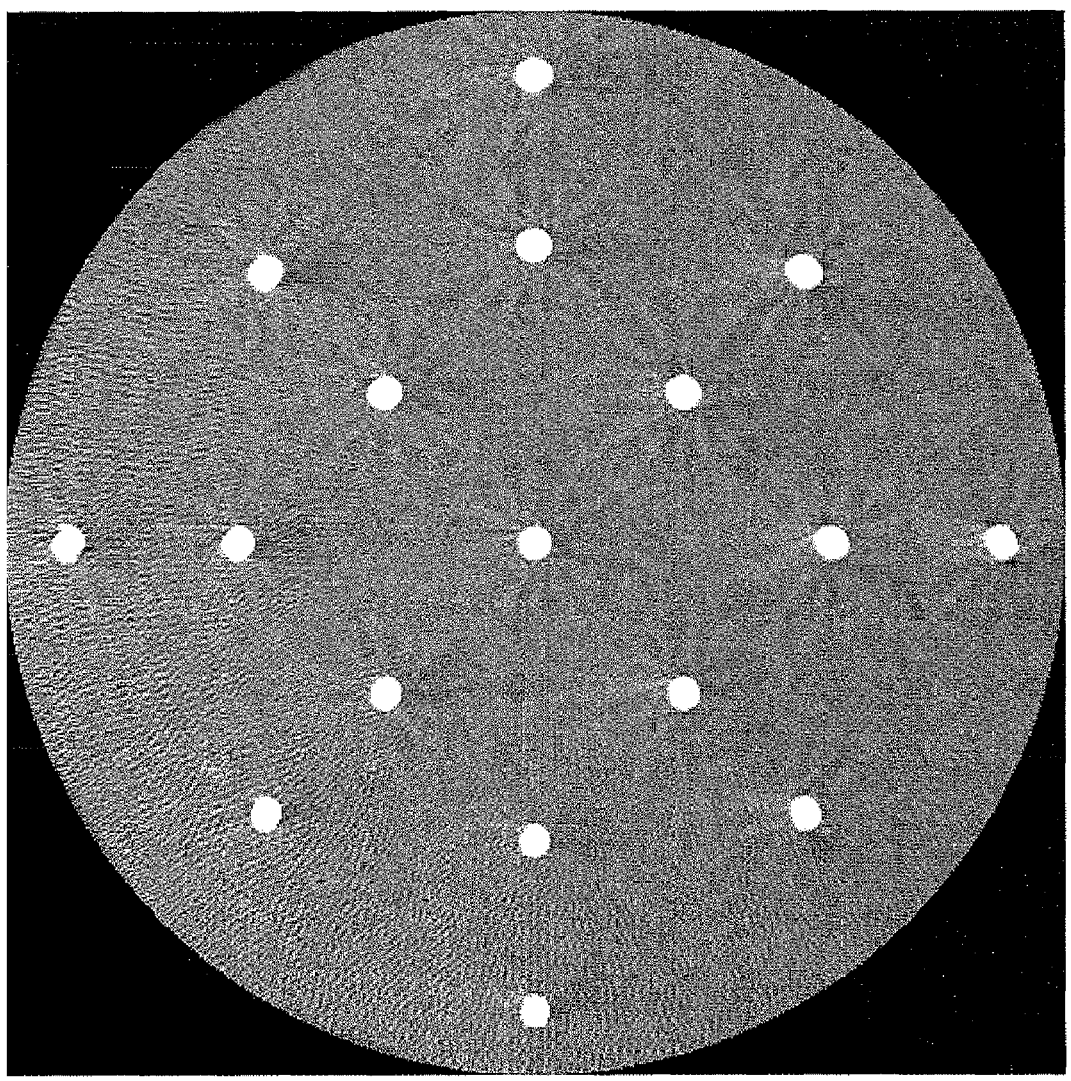
FIG. 17 is an image example ($\alpha_{iso}$=0.125 and k=1) obtained by the scanning method and image reconstruction of the present invention.

FIG. 17 illustrates an image obtained with a small flying distance equal to one-half of $\alpha_{iso}$ of the conventional zFFS method, i.e., $\alpha_{iso}$=0.125, when k is made equal to 1 in performing image reconstruction. The conditions are the same as the cases of FIGS. 3 and 8 except the following difference. The image illustrated in FIG. 17 differs from those of FIGS. 3 and 8 in that $\alpha_{iso}$ is neither zero nor 0.25 and γ is suitably determined such that back projection is performed along a second path different from a first path where projection data were obtained. It is clearly found that in the image illustrated in FIG. 17, windmill artifacts are satisfactorily suppressed over the whole region in comparison with the images illustrated in FIGS. 3 and 8.

Figure 8:
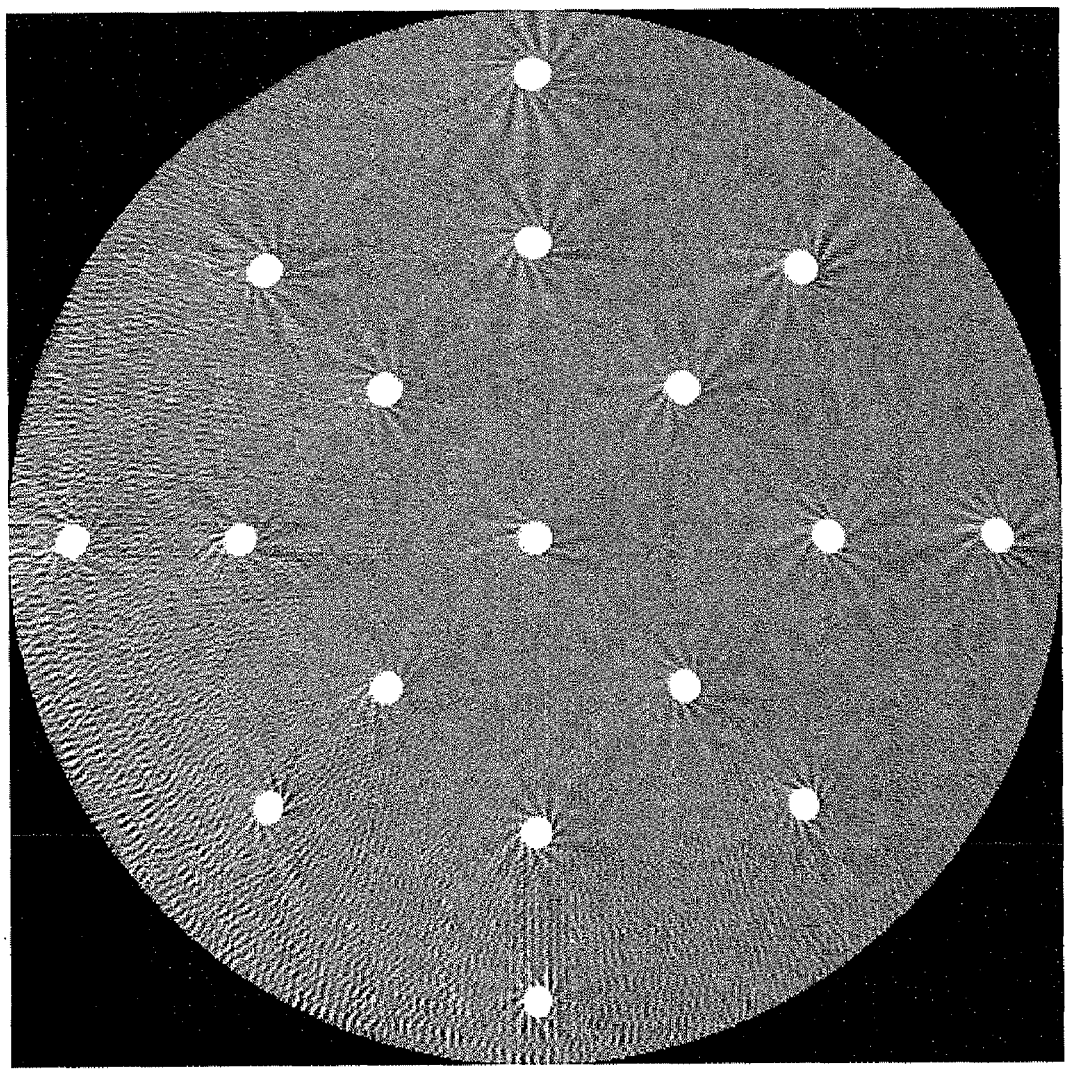
FIG. 8 is a diagram illustrating an image example obtained by the zFFS method with the conditions illustrated in FIGS. 3 and 4.

The shower-shaped artifacts on the left side of the image of FIG. 17 have been reduced compared with the image of FIG. 8. The reason is briefly described although explanation lacks sequence. Its mechanism in the case of conventional zFFS method is as follows: The final image reconstruction result can be considered to be an image imaginarily reconstructed by adding together an image obtained by using only even views and an image obtained by using only odd views.

For one of the two images, the number of views per one rotation is reduced by half, i.e., the pitch between projection angles is large, so that severe shower-shaped artifacts are caused by a reduction in the number of views. The same applies to the other image. If the two images are added together, the number of views is increased so that shower-shaped artifacts can be reduced. However, the two images are images obtained by observing other scan planes away in the Z-axis direction, so in a subject varying in shape in the Z-axis direction the two shower-shaped artifacts differ in shape from each other. Consequently, severe shower-shaped artifacts are caused without canceling each other.

For the method according to the present invention, compared with the conventional zFFS method, the flying distance is one half, the distance of an observing plane for each of odd and even views is one half, and the distance of Z-directional positions to which respective projection data are back projected is also one half. Therefore, the shower-shaped artifacts of both images are relatively coherent. If both are added together, the coherent shower-shaped artifacts cancel each other and a resultant image becomes very close to a state in which the number of views is sufficient.

A quantitative comparison of windmill artifacts in comparison with the conventional type zFFS method and other methods, and spatial resolution in the Z-axis direction, will be described later with reference to FIGS. 22 and 23.

(B2) Second Embodiment

Figure 18:
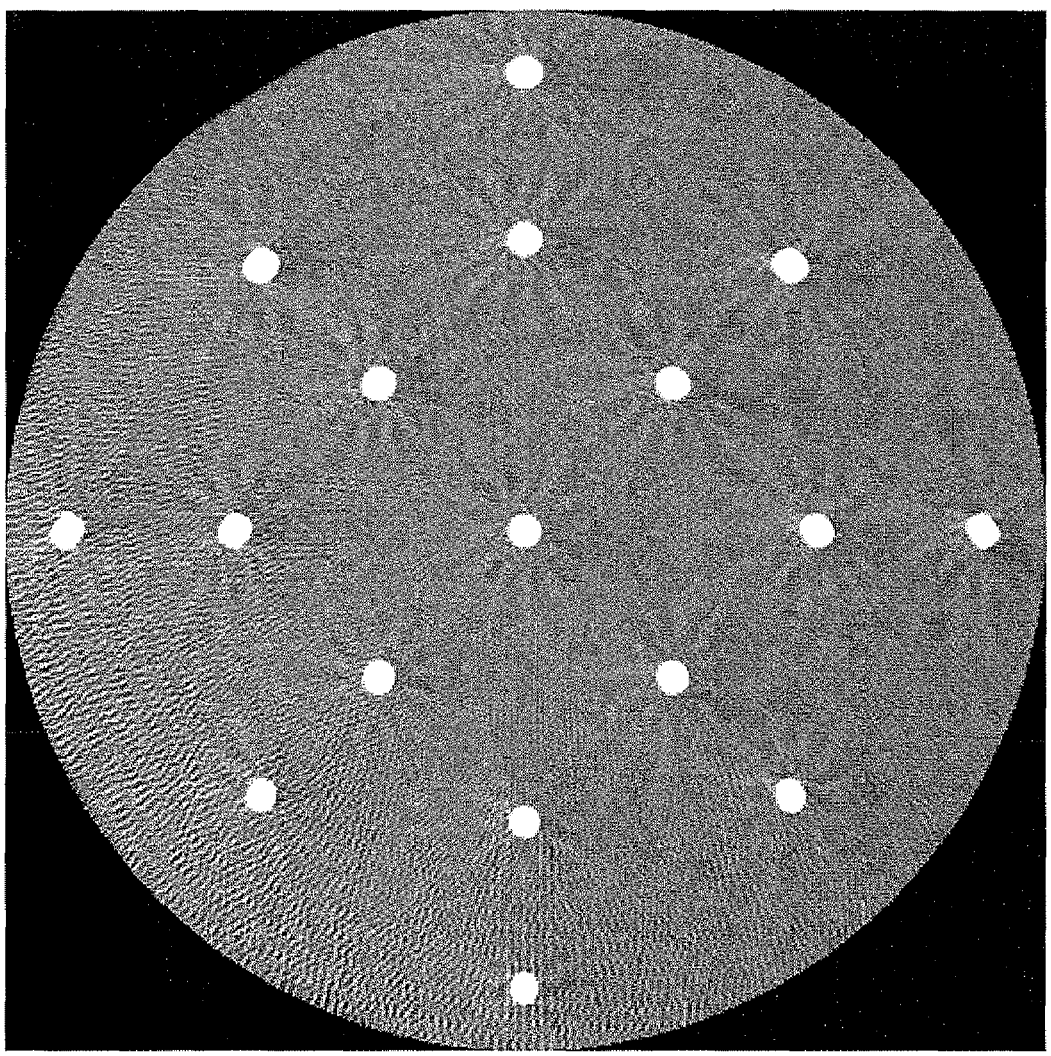
FIG. 18 is an image example ($\alpha_{iso}$=0.0625 and k=1) obtained by the scanning method and image reconstruction of the present invention.

FIG. 18 illustrates an image obtained with a very small flying distance equal to one-quarter of $\alpha_{iso}$ of the conventional zFFS method, i.e., $\alpha_{iso}$=0.0625, when k is made equal to 1 in performing image reconstruction. In comparison with not only the image of FIG. 3 but also the image of FIG. 8, windmill artifacts are clearly and satisfactorily suppressed over the whole area. This result was obtained by simulation with scan slice thickness $s_{iso}$=1 mm. Thus, even if the focus flying width is made very small, a sufficient effect is obtained, which is why it is easy to employ the zFFS method even if the scan slice thickness $s_{iso}$ is 2 mm or 3 mm.

The shower-shaped artifacts are slightly reduced compared with the image illustrated in FIG. 8 and are not different substantially. The reason is that the distances of the observing planes for odd and even views are close to each other, but a position where back projection is performed in image reconstruction is far away, compared with the case of FIG. 17 where $\alpha_{iso}$=0.125. Nevertheless, the image illustrated in FIG. 18 is slightly better than the image illustrated in FIG. 8 of the conventional zFFS method.

A quantitative comparison of windmill artifacts in comparison with the conventional type zFFS method and other methods, and spatial resolution in the Z-axis direction, will be described later with reference to FIGS. 22 and 23.

(B3) Third Embodiment

In the foregoing examples, k is equal to 1, but can be arbitrarily selected. It is easily found that if the value of k is small, spatial resolution is reduced in the Z-axis direction. This is because, from the aforementioned Eqs. 14 and 18, a true spectrum is multiplied by $A_0$ expressed with the following Eq. 29.

[Formula 21]

$$A_0 = \cos\left(2\pi fs\left(\frac{1-4\alpha}{2k}\right)\right) \quad (29)$$

Figure 23:
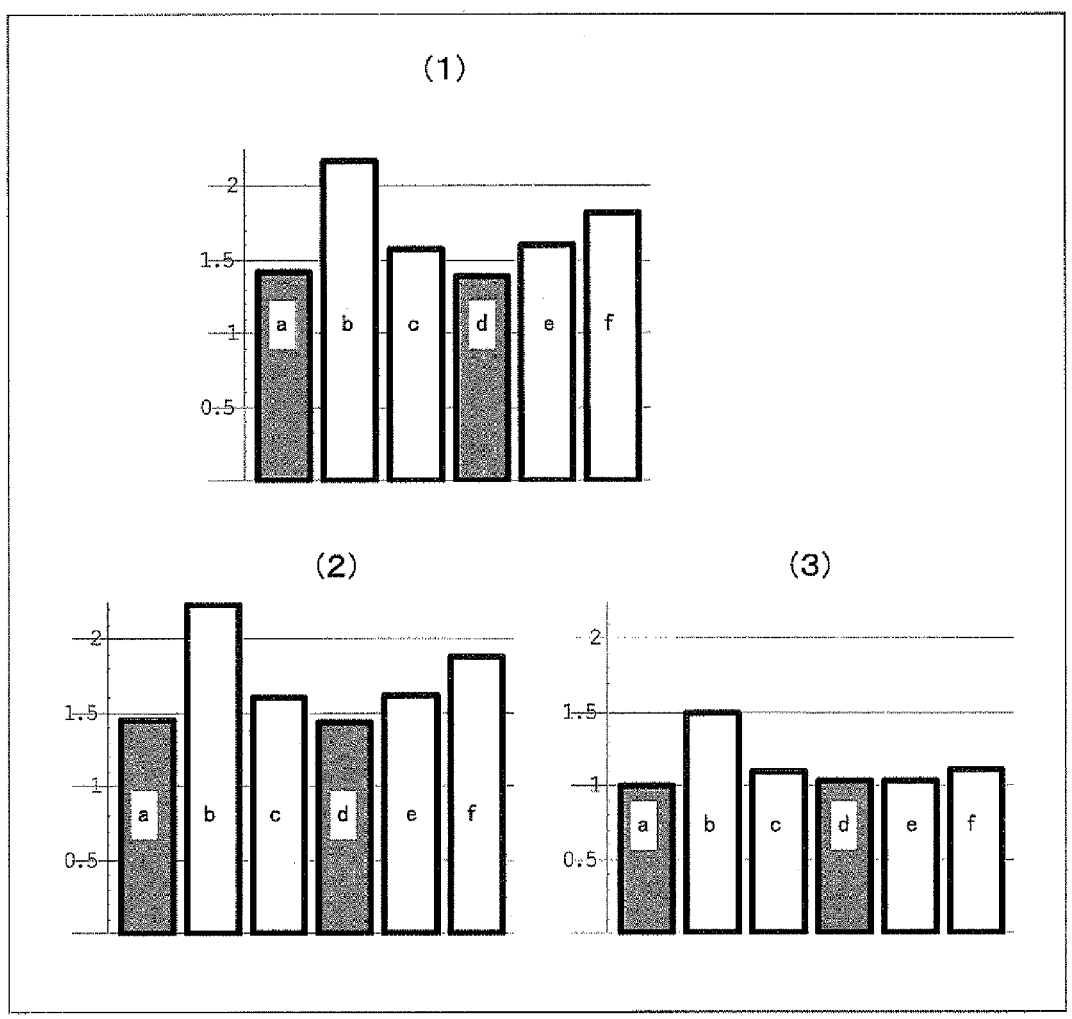
FIG. 23 is a graph illustrating FWHM (full width half maximum) of SSP obtained by each scanning method and each image reconstruction method.

When $\alpha_{iso}$ is not an extremely small quantity, even in the case of k=1, as seen from FIG. 15, and as also seen from SSP (Slice Sensitivity Profile which represents the Z-axis direction sensitivity profile of a reconstructed image and whose width is the image thickness) data (FIG. 23). Although the compromise on the spatial resolution is negligible, in the case where ensuring spatial resolution has priority over windmill-artifact suppression, k may be selected large.

Figure 4:
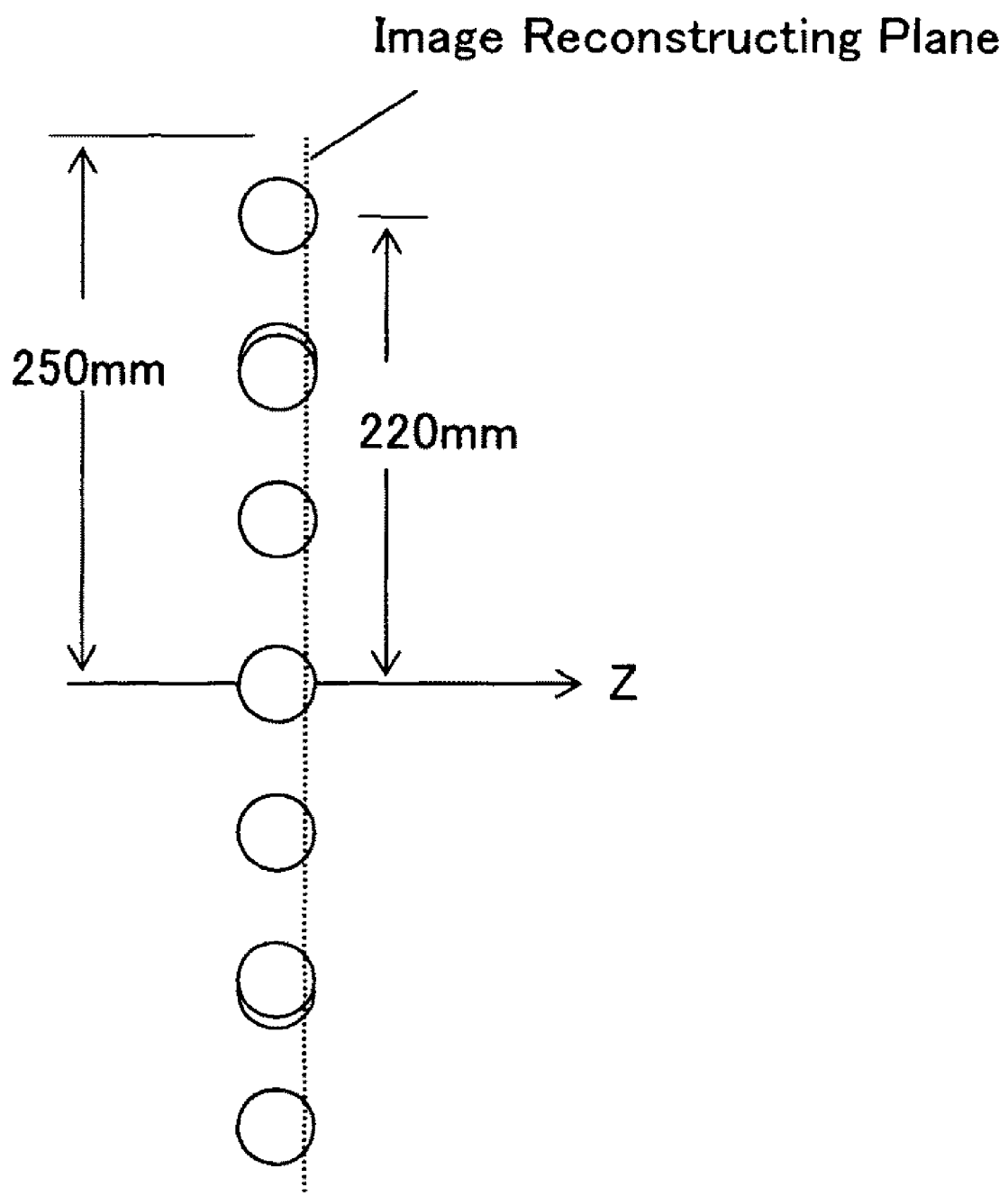
FIG. 4 is a schematic view for explaining photography subjects, with which the image illustrated in FIG. 3 was obtained, and imaging positions.
Figure 5:
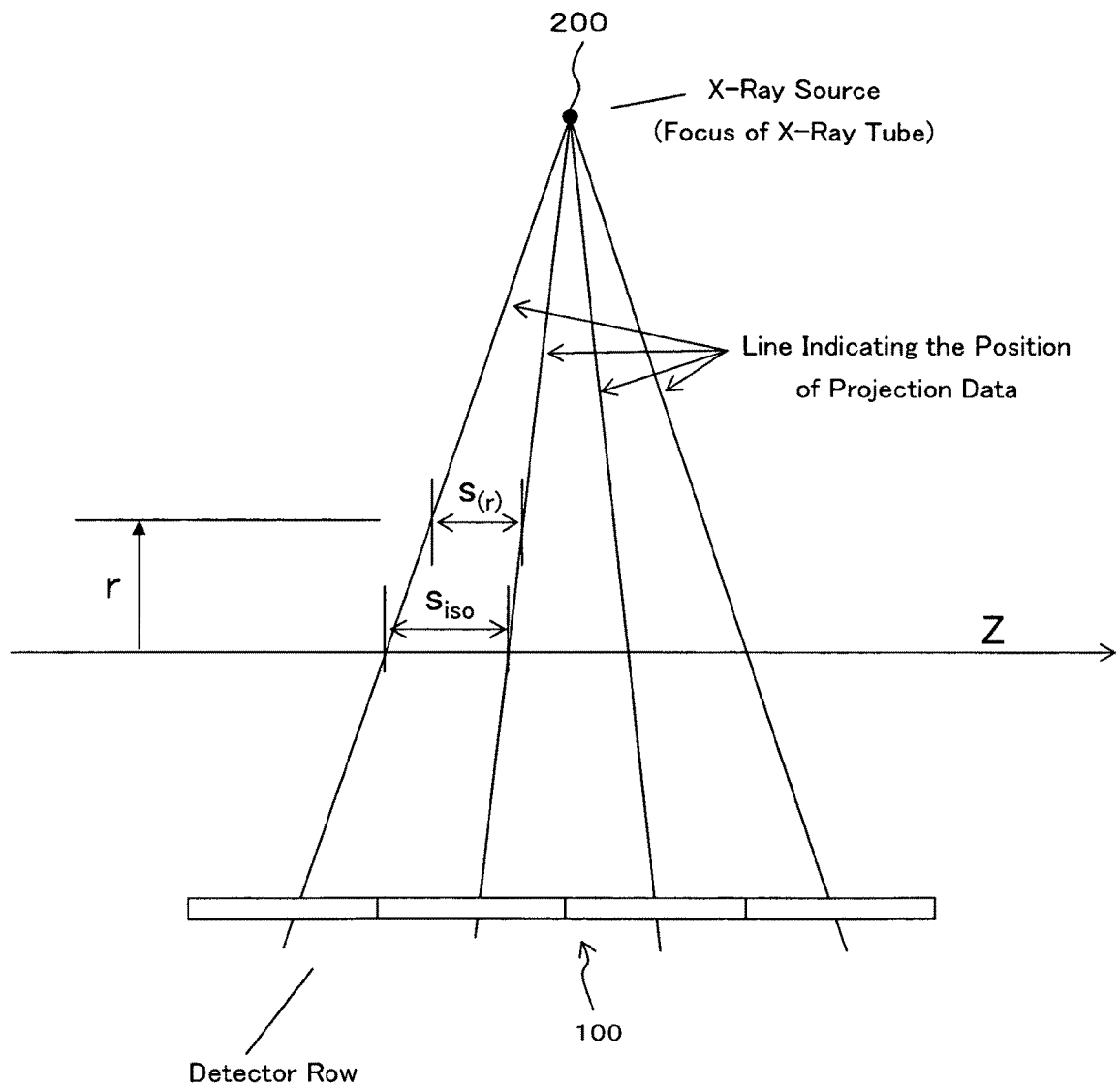
FIG. 5 is a diagram for explaining Z-axis sampling used in a multislice CT.
Figure 19:
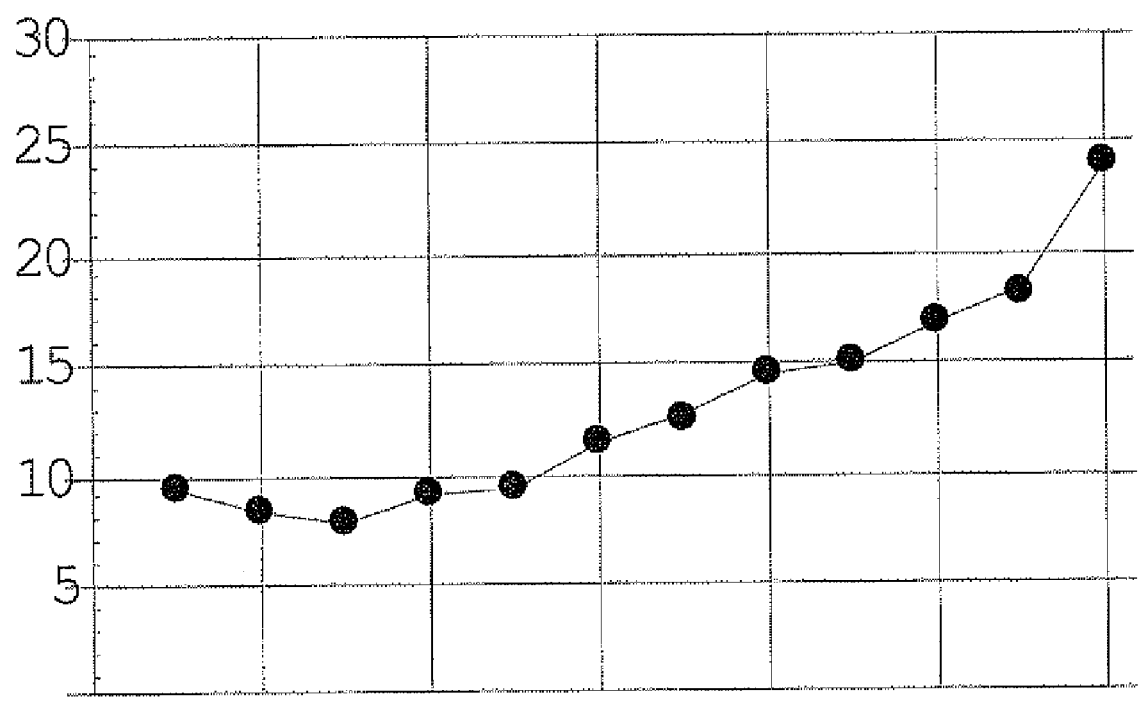
FIG. 19 is a graph illustrating windmill artifacts quantitatively measured by varying k in accordance with the present invention.

FIG. 19 illustrates windmill artifacts quantitatively measured when image reconstruction is performed varying k. This illustrates standard deviations in CT values on a circumference 15 mm away from the center of the second sphere from the top illustrated in FIG. 4, obtained when image reconstruction is performed varying k. The conditions are the same as the case of FIG. 17 except k. That is, $\alpha_{iso}$ is equal to 0.125. The data points are k=0.8, 0.9, 1.0, 1.1, 1.2, 1.4, 1.6, 1.8, 2.0, and ∞ from the left of FIG. 19.

It is found that windmill artifacts become minimum in the proximity of k=∞. It is also found that if k is made smaller than 1, windmill artifacts are increased. Note that k=1 means that back projection is performed along the data-acquired path. It is found that, like the present invention, in an image reconstruction method having k<<∞, even when k is somewhat greater than 1, windmill artifacts are considerably suppressed. Thus, selection of k is arbitrary.

A quantitative comparison of windmill artifacts in comparison with the conventional zFFS method and other methods, and spatial resolution in the Z-axis direction, will be described later with reference to FIGS. 22 and 23.

(B4) Fourth Embodiment

Figure 20A:
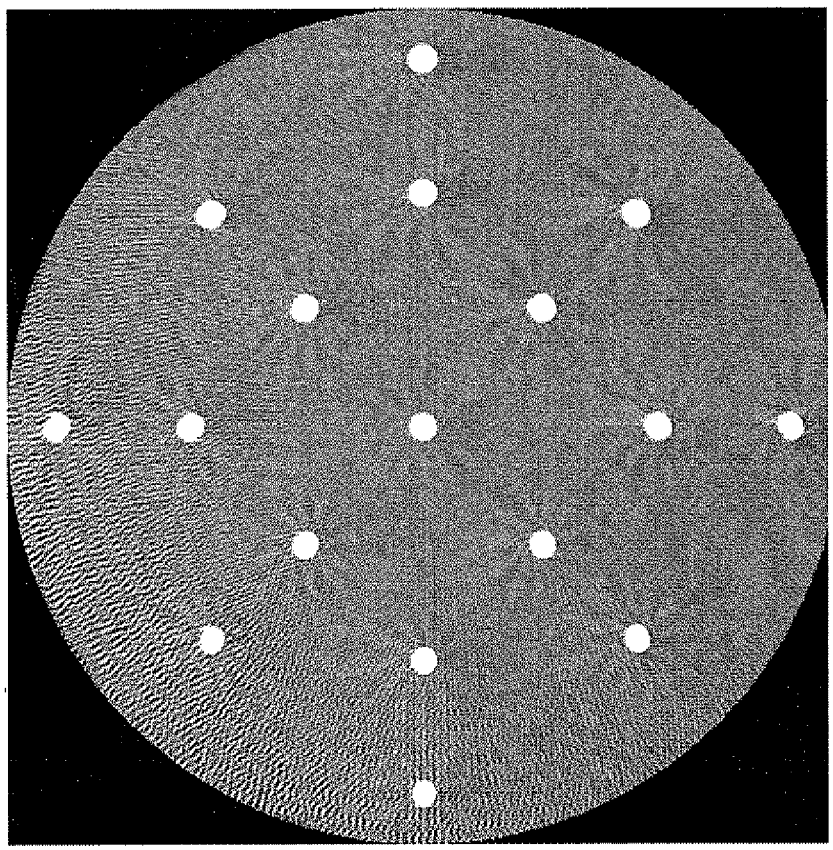
FIG. 20 is a diagram illustrating an image example in which the image reconstruction method of the present invention is applied to an ordinary scanning method in which there is no focus flying, FIGS. 20(a) and 20(b) illustrating the case of k=1 and the case of k=2, respectively.
Figure 20B:
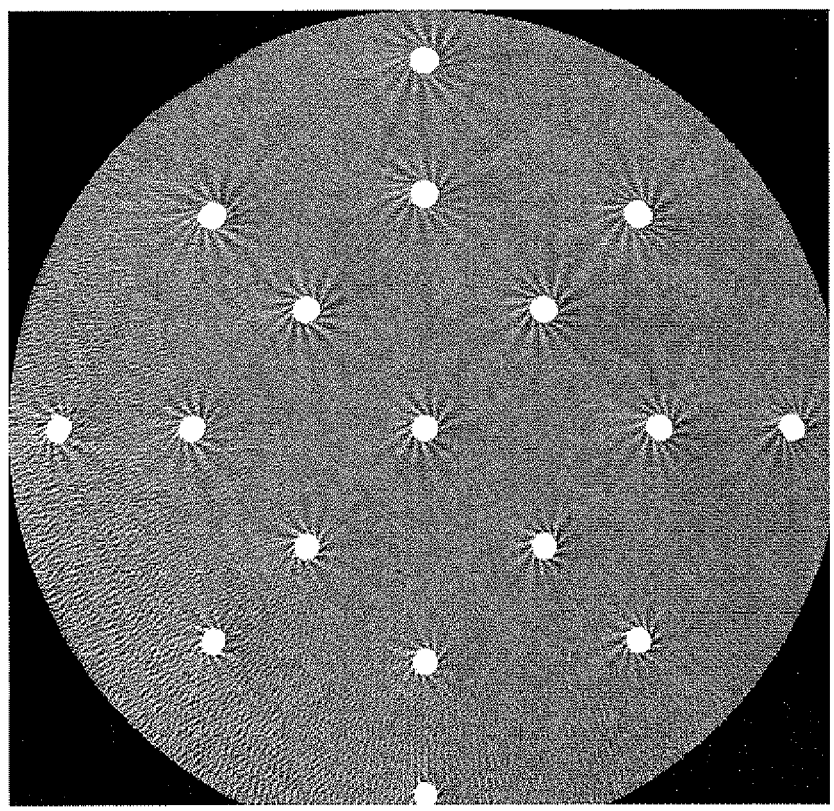

This is an entirely different embodiment of the present invention. In this embodiment, the present theory is applied in the case of a scanning method not employing the zFFS method. That is, in the aforementioned equations, $\alpha_{iso}$ is made zero. FIG. 20(*a*) illustrates results obtained by scanning with $\alpha_{iso}$=0 and performing image reconstruction with k=1, and FIG. 20(*b*) illustrates results obtained by scanning with $\alpha_{iso}$=0 and performing image reconstruction with k=2. In either case, particularly when k=1, windmill artifacts are appreciably suppressed compared with the image illustrated in FIG. 3. However, $\alpha_{iso}$ is zero, i.e., α is zero, so when k=1, as illustrated in the aforementioned Eq. 29, and as illustrated later in SSP data (FIG. 23), blurs in the Z-axis direction cannot be neglected.

Figure 3:
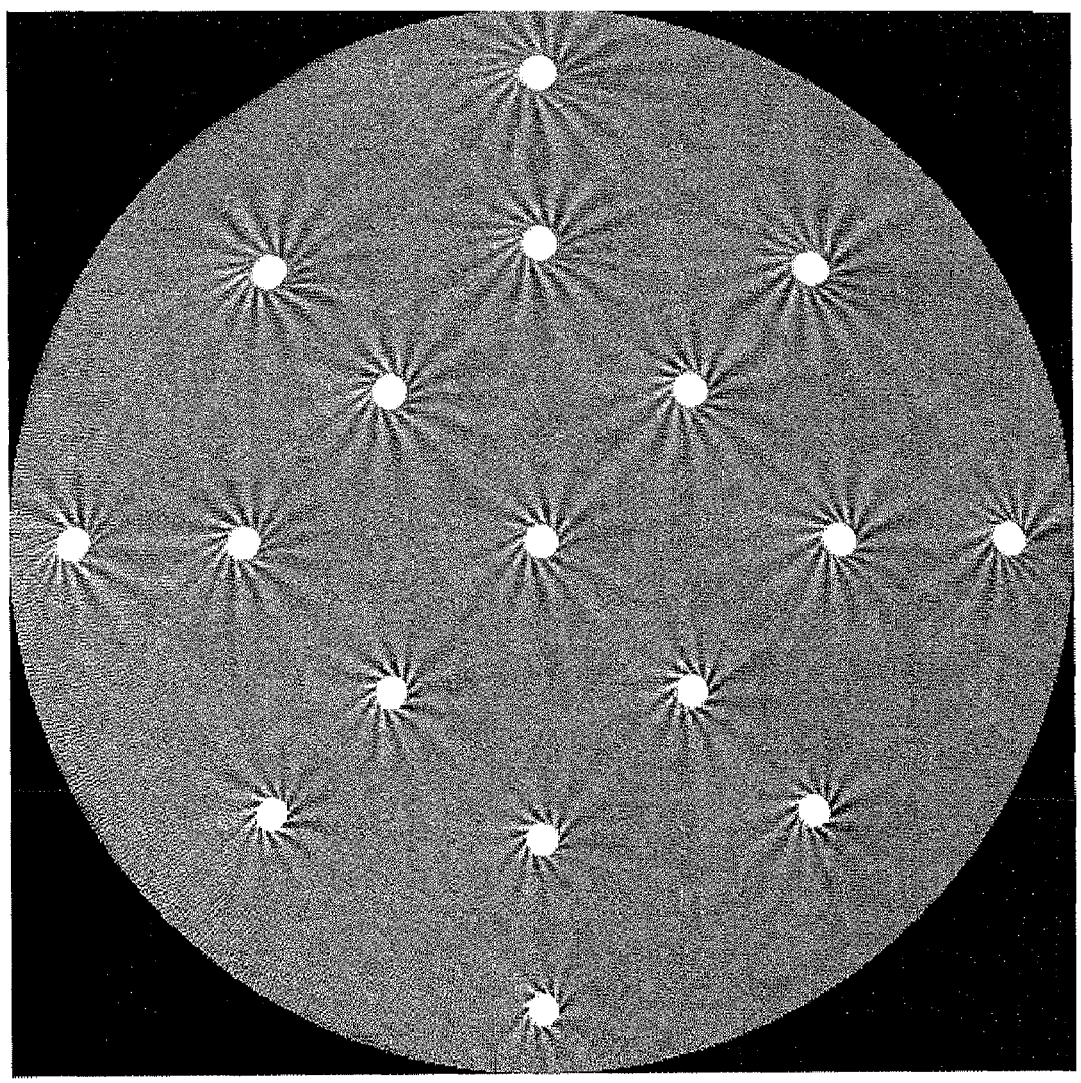
FIG. 3 is a diagram illustrating an image example in which windmill artifacts have occurred.

In the case of k=2, blurs are slight, but windmill artifacts have significantly been improved compared with the image in FIG. 3 obtained by normal image reconstruction [in which k corresponds to ∞, i.e., there is no shifting of focal positions and detector positions (refer to tables 1 and 2)]. Even compared with the image in FIG. 8 obtained by the conventional zFFS method, windmill artifacts are slightly stronger in general, but are improved at some locations.

A quantitative comparison of windmill artifacts in comparison with the conventional zFFS method and other methods, and spatial resolution in the Z-axis direction, will be described later with reference to FIGS. 22 and 23.

Now, interesting facts will be given of an image obtained when $\alpha_{iso}$=1 and k=2.

According to the aforementioned Tables 1 and 2, in this case, image reconstruction is performed with a focal position held in an actual focal position, and detector-element positions for odd and even views shifted back and forth in the Z-axis direction by ¼ pitch. This means that if image reconstruction is performed separately for odd views and for even views, image reconstruction is performed at positions shifted back and forth from the center of axis in the Z-axis direction by ±¼ of $s_{iso}$ respectively. If added together, the resultant image is the same as the case of FIG. 20(*b*).

Figure 21:
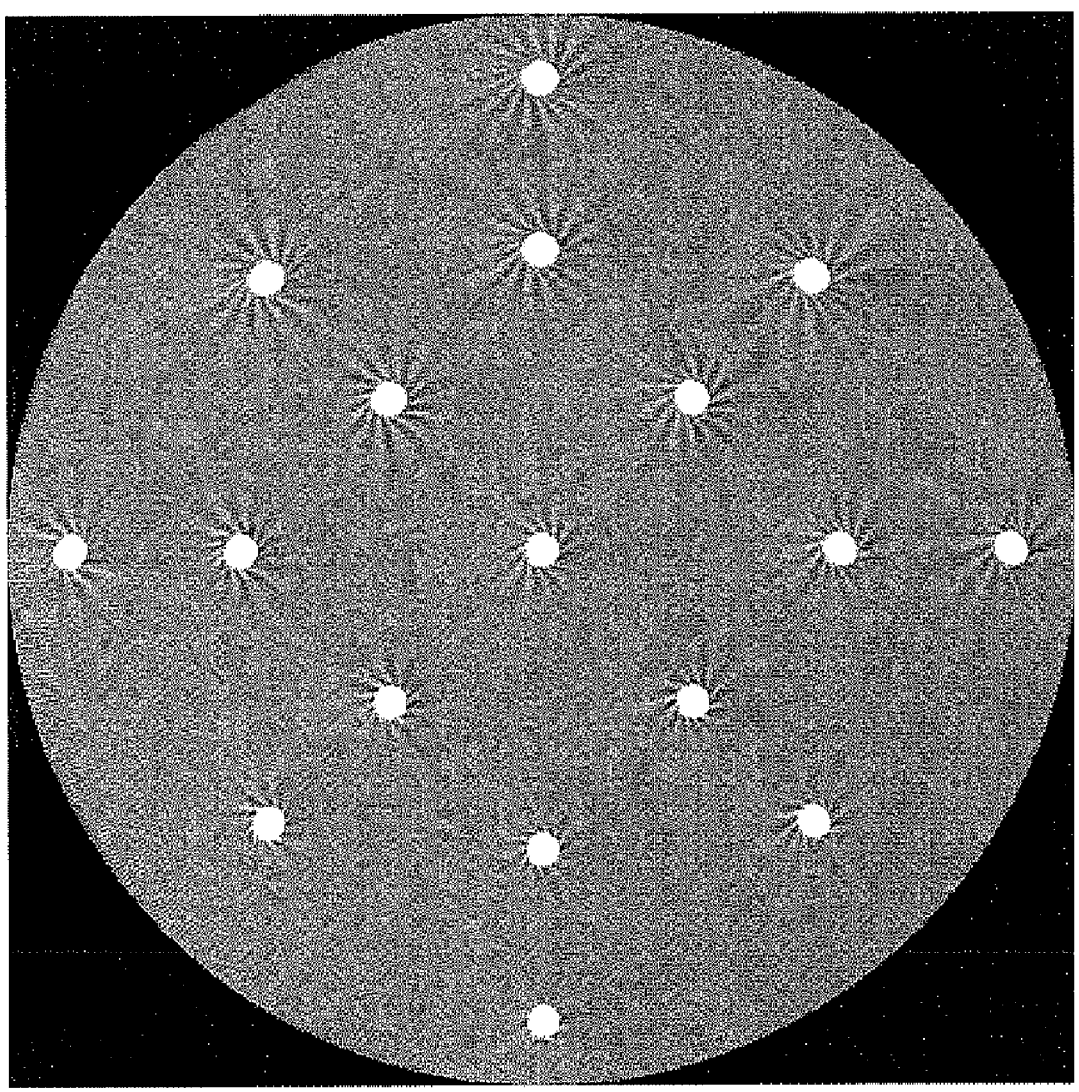
FIG. 21 is a diagram illustrating an image example obtained by reconstructing images with the ordinary scanning method (in which there is no focus flying) and conventional image reconstruction method at positions shifted from an imaging plane in the Z-axis direction by ±¼ of $s_{iso}$, and then adding the two images together.

From this fact, if, without separating for odd and even views, images are reconstructed respectively at positions shifted back and forth from an imaging plane in the Z-axis direction by ±¼ of $s_{iso}$ with the conventional image reconstruction method, and the two images are added together, then an image approximately equal to the image illustrated in FIG. 20(*b*) must be obtained. An image thus obtained is illustrated in FIG. 21. In the image illustrated in FIG. 21, windmill artifacts are approximately equal to those of the image illustrated in FIG. 20(*b*).

The reason shower-shaped artifacts hardly occur is that as processing is not performed separately for odd views and for even views, two images before being added together have a sufficient number of views. This method is effective as it is. However, two images are reconstructed and formed into a single image, so the image construction process is time-consuming. In addition, it can be easily anticipated that, if the number of rows is increased like 32 rows or 64 rows, in such a method in which two images are reconstructed at positions shifted back and forth from an imaging plane in the Z-axis direction by ¼ of $s_{iso}$ by the conventional image reconstruction method without separating for odd views and for even views and the two images are added together, compared with an image when $\alpha_{iso}$=0 and k=2, image quality becomes approximately the same at the center of rotation, but the windmill suppression effect or SSP described later will worsen at positions away from the center of rotation. A detailed description will not be given.

Similarly, for an image when $\alpha_{iso}$=0 and k=1, images of similar characteristics can be obtained by the aforementioned method, in which two images are reconstructed at positions shifted back and forth from an imaging plane in the Z-axis direction by ½ of $s_{iso}$ by the conventional image reconstruction method without separating for odd views and for even views and the two images are added together. This is also a good method. However, it can be likewise anticipated that if the number of rows is increased, in comparison with an image when $\alpha_{iso}$=0 and k=1, difference will become great and the windmill suppression effector SSP will worsen at positions away from the center of rotation.

Figure 22:
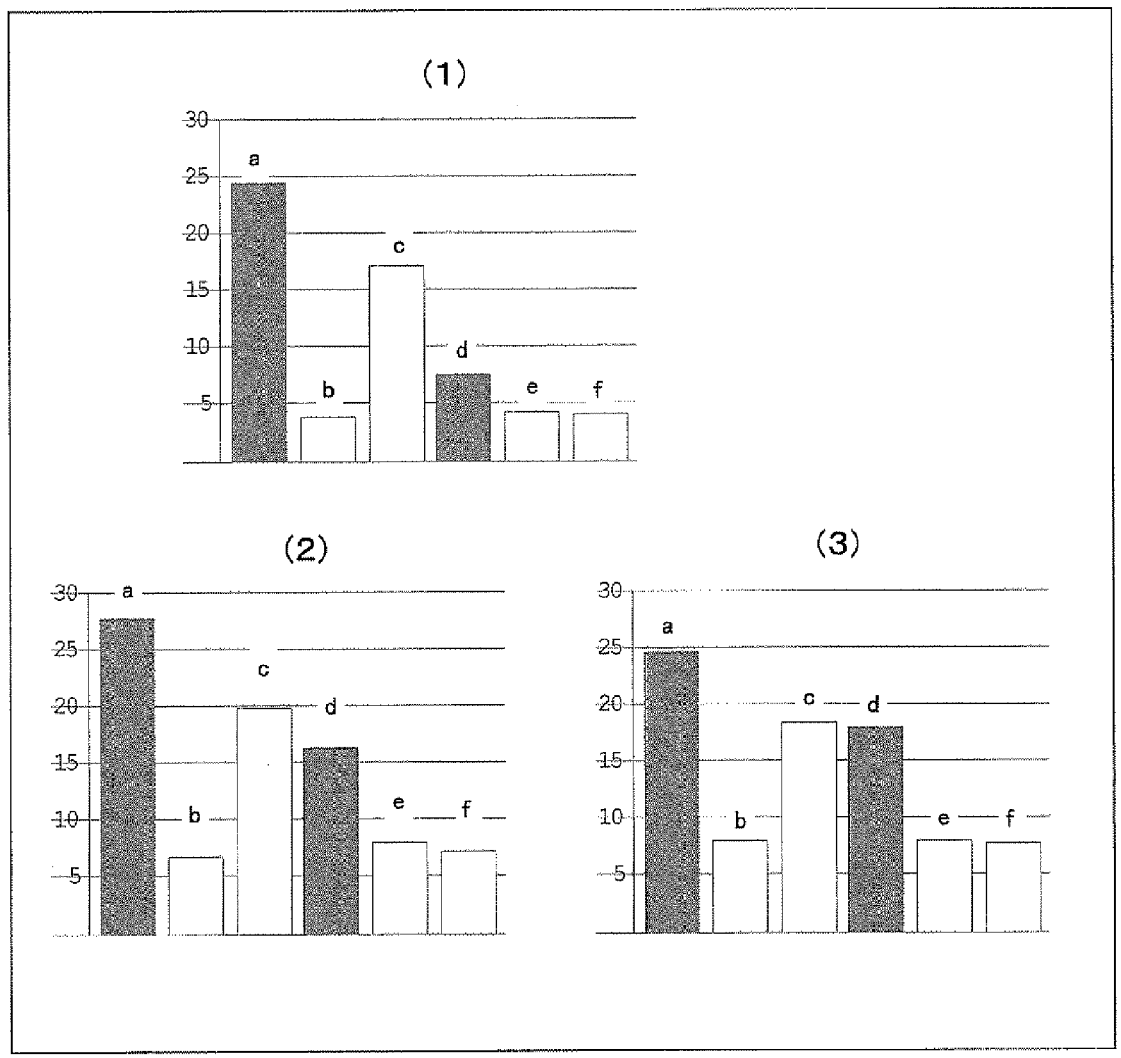
FIG. 22 is a graph illustrating windmill artifacts quantitatively measured by each scanning method and each image reconstruction method.

For each of the cases described above, a quantitative comparison of windmill artifacts is illustrated in FIG. 22. As it is well known that the behavior of windmill artifacts varies depending on place, the quantitative comparison was made at three representative places. That is, FIG. 22(1) illustrates bar graphs in the spherical periphery of the center of rotation (Z-axis in FIG. 4), FIG. 22(2) illustrates bar graphs in the periphery (the second sphere from the top in FIG. 4) away from the center of rotation by a radius of 140 mm, and FIG. 22(3) illustrates bar graphs in the periphery (the top sphere in FIG. 4) away from the center of rotation by a radius of 220 mm.

The bar graph indicated with reference character a represents the case where the conventional image reconstruction was performed when there is no flying of a focus ($\alpha_{iso}$=0) (corresponding to FIG. 3). The bar graph indicated with reference character b represents the case where image reconstruction was performed when there is no focus flying ($\alpha_{iso}$=0) and k=1 in accordance with the present invention (corresponding to FIG. 20(a)). The bar graph indicated with reference character c represents the case where image reconstruction was performed when there is no focus flying ($\alpha_{iso}$=0) and k=2 in accordance with the present invention (corresponding to FIG. 20(b)) The bar graph indicated with reference character d represents the case where a scan was performed by the conventional zFFS method ($\alpha_{iso}$=0.25), and image reconstruction was performed when k=∞ in accordance with the conventional zFFS method (corresponding to FIG. 8). The bar graph indicated with reference character e represents the case where a scan was performed by the zFFS method ($\alpha_{iso}$=0.125) in accordance with the present invention, and image reconstruction was performed when k=1 in accordance with the present invention (corresponding to FIG. 17). The bar graph indicated with reference character f represents the case where a scan was performed by the zFFS method ($\alpha_{iso}$=0.0625) in accordance with the present invention, and image reconstruction was performed when k=1 in accordance with the present invention (corresponding to FIG. 18).

In the bar graphs a, b, and c where there is no focus flying, windmill artifacts (b and c) caused by the image reconstruction method of the present invention have considerably been reduced at any place, compared with windmill artifacts (a) caused by the conventional image reconstruction method. Except for the center of rotation, b and c are not so worse than d (scanning and image reconstruction by the conventional zFFS method in which there is focus flying), and particularly, b is far superior to d.

Even in the bar graphs d, e, f where there is focus flying, it is clear that in comparison with d (scanning and reconstruction by the conventional zFFS method), e and f (scanning with small $\alpha_{iso}$ and image reconstruction along an optimum back projection path of the present invention) can significantly reduce windmill artifacts at anyplace. It is believed that since these measurements, in addition to windmill artifacts, contain very small shower-shaped artifacts and other artifacts, the effect of reducing windmill artifacts is greater than these bar graphs.

The effect of artifact suppression illustrated in FIG. 22 is accompanied by the price to pay, that is come blurring in the Z-axis direction, so this must be taken into consideration at the same time.

The image reconstruction method of the present invention is unable to avoid to some extent blurs in the Z-axis direction which result from the fact that projection data are not back projected along the path where the data were acquired. However, the penalty is far smaller than the effect of windmill-artifact reduction. Spatial resolution in the Z-axis direction is generally discussed with SSP (Slice Sensitivity Profile which represents the Z-axis direction sensitivity profile of a reconstructed image and whose width is the image thickness), so it is represented by a half width of SSP.

The influence of the image reconstruction method of the present invention on SSP is clearly indicated by the aforementioned Eq. 29. From this a half width of SSP can be easily calculated, but it is represented by simulation, not calculation. It is an evaluation method called a beads method. By arranging small X-ray attenuation bodies at each point in a plane of z=0, scanning, and performing image reconstruction at small intervals along the Z-axis in the vicinity of z=0, bleeding of small spheres has occurred in the Z-axis direction, and the results are illustrated in FIG. 23. In this simulation, $s_{iso}$ is 1 mm, a focus dimension is 1 mm, a 16-row multi-slice CT is employed, and a helical pitch is 13. In FIG. 23, the units of the vertical axis are mm and a to f correspond to the aforementioned scanning conditions a to f (FIG. 22).

It is known that in the scanning condition, i.e. in the condition that a helical pitch is not sufficiently small, as with the case of windmill artifacts, SSP also depends upon not only a distance from the center of rotation but also a place in a rotational angle direction. Therefore, for a place of r=220 mm away from the center of rotation, half widths are illustrated at a place where SSP is most satisfactory or narrow (FIG. 23(2)) and at another place where SSP is worst or wide (FIG. 23(3)). FIG. 23(1) illustrates half widths of SSP of the center of rotation. SSP at a place of r=140 mm is intermediate behavior between r=0 mm and r=220 mm, so it is omitted from FIG. 23.

If FIG. 23 is compared with FIG. 22, in a, b, and c where there is no focus flying, the SSP half bandwidths of b and c by the image reconstruction of the present invention do not increase to the degree of the windmill-artifact suppressing effect, compared with a. For c, compared with the conventional zFFS method in which there is focus flying, there is almost no difference in windmill-artifact suppression except the center of rotation, i.e., the SSP half width slightly increase. Except the center of rotation, even if there is no focus flying, it is by no means inferior to the conventional zFFS method. In d, e, and f where there is focus flying, compared with the conventional zFFS method, e and f where the flying distance is ½ and only ¼ of the conventional method suppress windmill artifacts significantly, while worsening of SSP is slight.

[C] Overview of System Configuration and Operation

Figure 24:
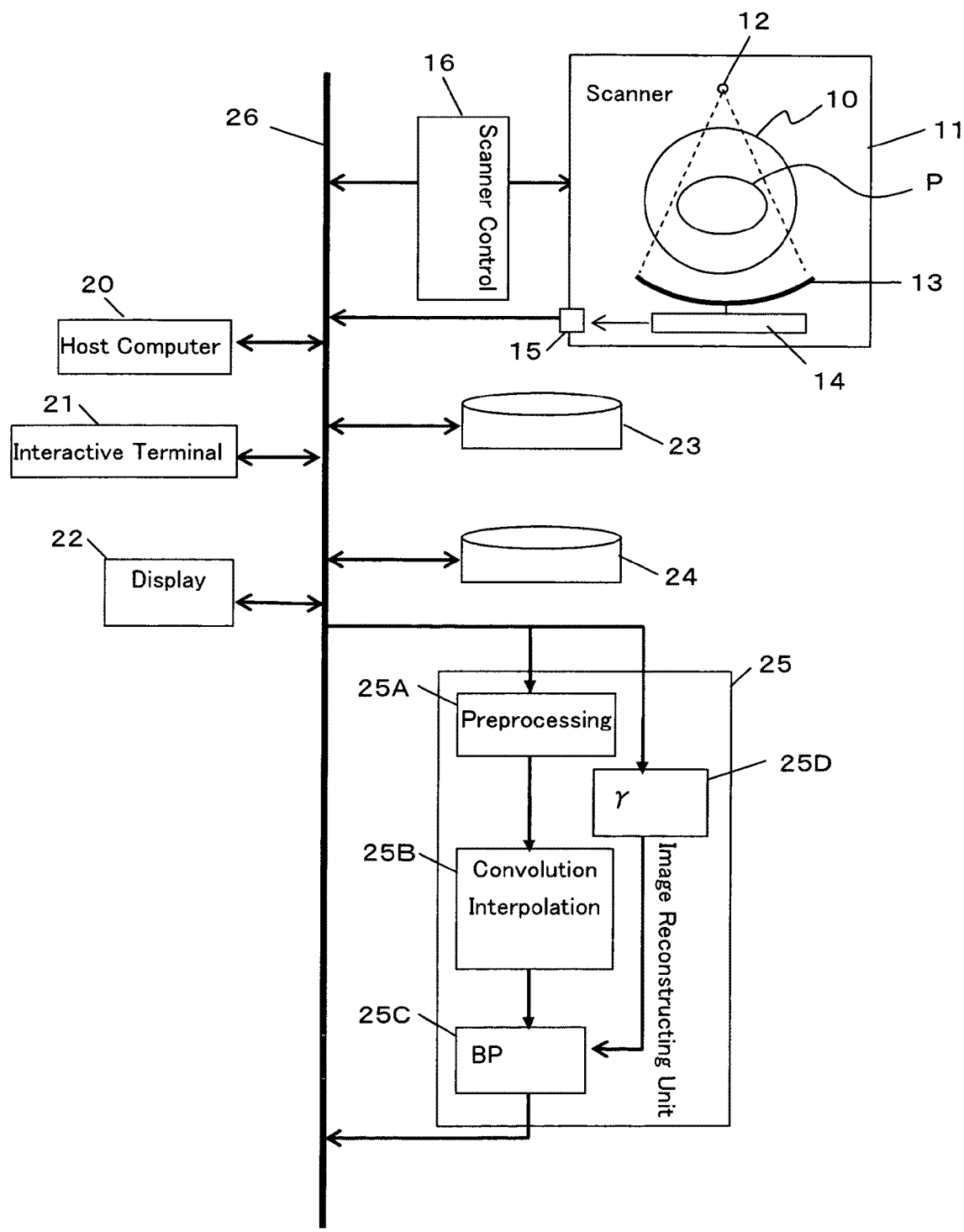
FIG. 24 is a block diagram illustrating an overview of the system configuration of an X-ray CT system according to the present embodiment.

FIG. 24 illustrates an overview of the system configuration of an X-ray CT system according to the present embodiment.

The X-ray CT system comprises a scanner 11, a data transmitter 15, a scanner controller 16, a host computer 20, an interactive terminal 21, a display 22, a first storage 23, a second storage 24, an image reconstructing unit 25, and a bus 26.

The scanner (X-ray detecting system) 11 is adapted to house within a tunnel-shaped diagnosis space 10 a test subject P which is an imaging object, and is disposed so that it is rotatable around the test subject P (axis of rotation or Z-axis) with the test subject P between an X-ray source 12 and an X-ray detector 13. As to the rotation, the X-ray source 12 and X-ray detector 13 may rotate as one body, or the X-ray detector 13 alone may rotate. As previously described in FIG. 1, the X-ray detector 13 is constructed so that a plurality of detector elements are arranged two-dimensionally. The X-ray detector 13 is also connected with a data acquisition system (DAS) 14.

Therefore, an X-ray beam, radiated from the X-ray source 12 and formed into a cone beam shape, is transmitted through the test subject P and is detected as electric data by each of the detector elements of the X-ray detector 13, and the electric data is converted into digital X-ray data by the DAS 14. This X-ray data is transferred as acquisition data to the bus 26 via the data transfer 15.

The scanner 11 is operation controlled by the scanner controller 16 through the bus 26. The scanner controller 16 performs control of supplying high voltage for X-ray radiation to the X-ray source 12, rotation control of the scanner 11, and operation (fixed-speed movement toward the Z-axis direction) control of a bed (subject carrying member or subject holding member, not illustrated) for moving (or carrying) the test subject 10 in the Z-axis direction within the space 10 while mounting the test subject P thereon. The scanner controller 16 further performs control of the thickness in the Z-axis direction (fore-and-aft direction orthogonal to the paper surface) of the X-ray beam that is formed into a cone beam shape. The scanner controller 16 also sends a control signal and an indication signal for the flying width of a focus, required for electromagnetically flying a focal position back and forth in the Z-axis direction every one step of a projection angle, to the X-ray source as occasion demands.

That is to say, this scanner 16 performs a function as a scan means for causing the X-ray detector 13 and DAS 14 to measure X-ray data obtained based on X rays radiated from the X-ray source 12 at each angle of rotation. Particularly, in the present example, the scanner 16 functions as a helical scan means for performing a helical scan by moving the test subject P (bed) at a fixed speed in the Z-axis direction during the rotation mentioned above. It is noted in FIG. 24 that the scanner controller 16 is illustrated outside the scanner 11 but may be disposed within the scanner 11.

The "helical scan" is normally performed by moving the test subject P (bed) in the Z-axis direction while rotating at least the X-ray source 12 around the test subject P (Z-axis), as described above. However, for instance, a helical scan may be implemented by moving the test subject P (Z-axis) in the Z-axis direction (direction is not always limited to the horizontal direction) while rotating it around the test subject P (Z-axis), without moving (or carrying) the test subject P despite the presence or absence of the bed above described. Namely, a helical scan can be easily implemented if at least the X-ray source 12 can be rotated and moved in the Z-axis direction with respect to the test subject P, in such a manner as to describe a spiral orbit around the test subject P. Therefore, the present invention does not exclude another spiral scan, which is obtained by moving the test subject P in the Z-axis direction while rotating it with the X-ray source 12 fixed (without rotation and movement in the Z-axis direction) although it is impractical.

The host computer 20 is adapted to perform general control of the entire system. Particularly, in the present example, the host computer 20 is able to execute the image reconstruction method previously described in detail by reading out and executing the stored contents (containing the image reconstruction program for the X-ray CT system) of the storages 23 and 24 via the bus 26. More specifically, the host computer 20 is able to execute a scanning process of causing the X-ray source 12 and X-ray detector 13 to rotate around the Z-axis with the Z-axis (axis of rotation) therebetween, by the scanner controller 16 and scanner 11. Furthermore, the hose computer 20 is able to execute an image reconstruction process of reconstructing images, by performing an arithmetical operation, in which two-dimensional projection data obtained on the basis of X-ray data detected by the detector elements of the X-ray detector 13 during the rotation in the scanning process are projected back along a path different in the Z-axis direction from the X-ray path for the projection data, by the image reconstructing unit 25.

In other words, functions (all or part of the function of each means) as the X-ray CT system for carrying out the image reconstruction method of the present invention can be implemented by executing the predetermined application program (above-described image reconstruction program) or OS (operating system) in which the program is incorporated, with the host computer 20.

The program is provided by being stored on a computer readable storage medium, such as a flexible disk, CD-ROM, CD-R, CD-RW, MO, and DVD etc. In this case, the host computer 20 reads out the above-described program from the storage medium, and employs the program, transferring and storing it to and into the storages 23 and 24 that are internal or external devices. Alternatively, after has been stored in a storage device (storage medium) such as a magnetic disk, optical disk, magneto-optical disk, or the like, the program may be provided from the storage device into the computer through wire lines.

The computer used herein is the concept of including hardware and OS (operating system), and means hardware that operates by being controlled under OS. In the case where OS is unnecessary and hardware is operated by an application program alone, the hardware itself corresponds to the computer. The hardware is equipped with at least a microprocessor such as CPU etc., and a means for reading out programs stored in a storage medium. The storage medium, in addition to the above-described flexible disk, CD-ROM, CD-R, CD-RW, DVD, magnetic disk, optical disk, and magneto-optical disk, may employ a variety of computer readable media, such as an IC card, ROM cartridge, magnetic tape, punch card, internal storage within a computer (memory such as RAM or ROM etc.), and external storage etc.

The interactive terminal 21 is equipped with an input device, such as an operating device, so that an operator can input necessary information.

The display 22, in addition to displaying a reconstructed image, is used as an operator manipulates the system interactively.

The first and second storages 23 and 24 are storages such as magnetic disks. The first storage 23 stores a list of system programs (containing the image reconstruction program for the X-ray CT system) and system constants, a table for selecting a focus flying width according to each of scanning conditions, a list of parameters for image reconstruction, and so forth. The second storage 24 stores the data acquired from the DAS 14 and data processed in a preprocessing section to be described later, that is, projection data, and also stores image data reconstructed as described later. Note that the functions of these storages 23 and 24 may be implemented by separating the storage region of a single storage device into two regions.

The image reconstructing unit (image reconstructing means) 25 has a preprocessing section 25A for performing various corrections on acquisition data, a convolution-interpolation section 25B for performing convolution and interpolation on data corrected in the preprocessing section 25A, i.e., projection data, and a back-projection section 25C for performing a back projection operation on the data on which convolution and interpolation operations were performed by the convolution-interpolation section 25B.

The preprocessing section 25A, in performing image reconstruction from projection data obtained by a helical scan, also has functions of cutting out projection data in the range required for reconstructing an image in one cross section, and delivering the projection data to the convolution-interpolation section 25B. The back-projection section 25C has a function of back projecting data three-dimensionally along a path inclined in an axial direction. That is, it can back project the projection data obtained in each detector-element row at an angle of inclination relative to a Z-axis peculiar to each of the respective rows. Further, the back-projection section 25C has another function of performing the interpolation in the Z-axis direction (body axis or axis of rotation) that occurs in performing back projection.

The image reconstructing unit 25 is further equipped with a storage section 25D for storing information on a back projection path which is suitable for a quantity relating to the aforementioned focus flying width.

The "quantity relating to the focus flying width" may be the moved quantity of a focus, or may be the flying width $\alpha_{iso}s_{iso}$ of an X-ray beam at the center of rotation, or may be a relative flying width $\alpha_{iso}$, to a scan slice thickness $s_{iso}$. They are in a relation of conversion, and any of them is a quantity having essentially the same meaning. The following description employs $\alpha_{iso}$.

The information on a back projection path suitable for a flying width, which is stored in the storage section 25D, is typically a table of imaginary focal positions $Z_{fo}$ and $Z_{fe}$ and detector position shift quantities $Z_{do}$ and $Z_{de}$, made in advance for combinations of each $s_{iso}$ and each $\alpha_{iso}$, employing Eqs. 24 to 27. Typically, this table is made when k=1. However, as illustrated in theory and simulation, k may be a different value, depending on image quality desired by a designer. These values are not always fixed, but may be overwritten as needed by operator's selection etc.

The storage section 25D may store Eqs. 24 to 27 and calculate them to obtain imaginary focal positions $Z_{fo}$ and $Z_{fe}$ and detector position shift quantities $Z_{do}$ and $Z_{de}$ from $s_{iso}$ or $\alpha_{iso}$. In either case, the function of the storage section 25D is to determine which z-coordinates projection data is back projected on and send the determination to the back-projection section 25C.

The expression "determine which z-coordinates projection data is back projected on", in addition to shifted imaginary focal positions and shift quantities of detector position, can be expressed in many different ways producing the same results, so FIG. 22 merely illustrates γ as a general term for them. As illustrated in Eq. 23, γ is a value which uses as a reference a path of projection data at an intermediate position where a focus is not flown, and which indicates how far the projection data is back projected on from there.

The scan slice thickness $s_{iso}$ focus flying width and $\alpha_{iso}$ are appendant of projection data and X-ray data from the DAS14 and can be stored in or read out from the storage section 25D. In image reconstruction calculation, the storage section 25D selects suitable values for imaginary focal positions $Z_{fo}$ and $Z_{fe}$ and detector position shift quantities $Z_{do}$ and $Z_{de}$ from $s_{iso}$, and sends them to the back-projection section 25C.

Although not illustrated, geometrical information, such as a distance from the X-ray source 12 to the center of rotation and a distance from the X-ray source 12 to the X-ray detector 13, is stored in the first storage 23. This is also delivered to the storage section 25D via the host computer 20, and is sent to the back-projection section 25C.

Because of this, the back-projection section 25C is able to perform a mathematical operation, in which projection data is back projected on a path different by a predetermined quantity in the Z-axis direction from the path used at the time of projection data acquisition, for each view.

Now, operation of the X-ray CT system according to the present embodiment will be described cantering on the setting of a focus flying width and setting of a suitable back projection path.

An operator selects a scan slice thickness $s_{iso}$ according to the purpose of CT examination, also selects field of view etc., and inputs them to the interactive terminal 21. The host computer 20 determines a suitable focus flying width according to that. A focus is moved back and forth of the Z-axis, and the moved quantity is projected on the center of rotation. The value thus obtained is $\alpha_{iso}s_{iso}$, but in the following description, $\alpha_{iso}$ is employed.

As to $\alpha_{iso}$, suitable values have been determined beforehand according to $s_{iso}$ and stored in the first storage 23. Examples of the values are as follows. When $s_{iso}$=0.5 mm, $\alpha_{iso}$=0.2. That is, the X-ray beam is moved back and forth ±0.1 mm at the center of rotation in the Z-axis direction. In order to assure the effectuality of the zFFS method over the entire range of an image, it is desirable to make $\alpha_{iso}$ smaller than 0.25. However, if it is made too small, when the image reconstruction method of the present invention is applied blurs will occur slightly in the Z-axis direction. Therefore, $\alpha_{iso}$ is set at a value near to 0.25 in order to avoid the blur. If $\alpha_{iso}$=about 0.2, even when k is selected anyway in a practical range, the blurs in the Z-axis direction are so small that in practice, they are not discernable.

When $s_{iso}$=1.0 mm, $\alpha_{iso}$=0.15, that is, the X-ray beam is moved back and forth ±0.15 mm at the center of rotation in the Z-axis direction. Although the focus flying width of the X-ray source 12 can be made greater than 0.15 mm, this is assumed, just for an example, to be a maximum value of a practical design.

When $s_{iso}$=2.0 mm, $\alpha_{iso}$=0.075, that is, the X-ray beam is moved back and forth ±0.15 mm at the center of rotation in the Z-axis direction.

When $s_{iso}$>1.0 mm, in any case, the X-ray beam is moved back and force ±0.15 mm at the center of rotation in the Z-axis direction, and $\alpha_{iso}$=0.15/$s_{iso}$.

The host computer 20 reads out $\alpha_{iso}$ corresponding to $s_{iso}$ from the first storage 23 and sends them to the scanner controller 16. The scanner controller 16 determines a suitable collimator aperture width from $s_{iso}$ and $\alpha_{iso}$, and drives a collimator aperture and closing mechanism (not illustrated) to start a scan. At the same time, the focal position of the X-ray source 12 is moved back and forth by a quantity predetermined from $\alpha_{iso}$, for each view.

Acquisition data from the DAS 14, along with a scan, is sequentially stored in the second storage 24. At the same time, in the DAS 14, $s_{iso}$ and $\alpha_{iso}$ are added as appendant information to the acquisition data based on information (a path is not illustrated) delivered in advance from the scanner controller 16 to the DAS 14.

In performing image reconstruction, acquisition data is read out from the second storage 24 and delivered to the image reconstructing unit 25. The preprocessing section 25A corrects the acquisition data to obtain perfect projection data. The projection data is returned to and stored in the second storage 24 as needed, and $s_{iso}$ and $\alpha_{iso}$ are also written in as appendant information of this projection data.

The preprocessing section 25A extracts the projection data required for reconstructing a desired imaging plane, and delivers it to the convolution-interpolation section 25B. The convolution-interpolation section 25B performs the convolution process and interpolation process on the projection data within a detector-element row, and delivers the result to the back-projection section 25C.

The storage section 25D has stored a table (data in the form of a table) of imaginary focal positions $Z_{fo}$ and $Z_{fe}$ and detector position shift quantities $Z_{do}$ and $Z_{de}$ made in advance from each $s_{iso}$ and each $\alpha_{iso}$, employing Eqs. 24 to 27. For each view, by using the table, $s_{iso}$ and $\alpha_{iso}$ corresponding to the projection data, the imaginary focal positions $Z_{fo}$ and $Z_{fe}$ and detector position shift quantities $Z_{do}$ and $Z_{de}$ are delivered to the back-projection section 25C.

The back-projection section 25C performs back projection, employing the imaginary focal positions $Z_{fo}$ and $Z_{fe}$ and detector position shift quantities $Z_{do}$ and $Z_{de}$. The path along which the back projection is performed is at a position shifted by a predetermined quantity and at a predetermined angle in the Z-axis direction from the path where the projection data were acquired in the Z-axis direction, i.e., an optimum position at which windmill artifacts are suppressed while producing few blurs in the Z-axis direction.

From the foregoing description, an image, which has few windmill artifacts and hardly blurs in the Z-axis direction, is reconstructed.

(C1) Overview 1 of Another System Configuration and Operation

In the overview of system configuration and operation previously mentioned, it has been described that the focal position of the X-ray source 12 is flown back and force in the Z-axis direction. Even in the case where the focal position is not flown, this system configuration is substantially the same. By employing Eqs. 24 to 27 as $\alpha_{iso}=0$ and k=suitable value (typically 1), a table of imaginary focal positions $Z_{fo}$ and $Z_{fe}$ and detector position shift quantities $Z_{do}$ and $Z_{do}$ can be made. Based on this, for each view, by performing back projection in the Z-axis direction on a path different by a predetermined quantity from the path where the projection data were acquired, an image with reduced windmill artifacts can be obtained as illustrated in FIG. 18.

(C2) Overview 2 of Still Another System Configuration and Operation

In the overview of system configuration and operation previously mentioned, it has been described that the back-projection arithmetic section 25C is able to perform three-dimensional back projection, i.e., is able to perform back projection on the projection data of each detector-element row at an angle of inclination to the Z-axis peculiar to each of the respective rows. Even in the case where a helical scan is performed with an X-ray beam having a cone angle, as a means of obtaining an adequate image with an image reconstruction device having a back-projection section which performs two-dimensional back projection, there is the method disclosed in the aforementioned non-patent document 5 by way of example.

The image reconstruction plane is not a cross section perpendicular to the Z-axis but an inclined cross section (inclined plane). By collecting projection data having angles as close as to the inclined plane possible, and by approximating that the paths of projection data do not intersect with the inclined plane but are in the inclined plane, two-dimensional image reconstruction is performed.

Figure 25:
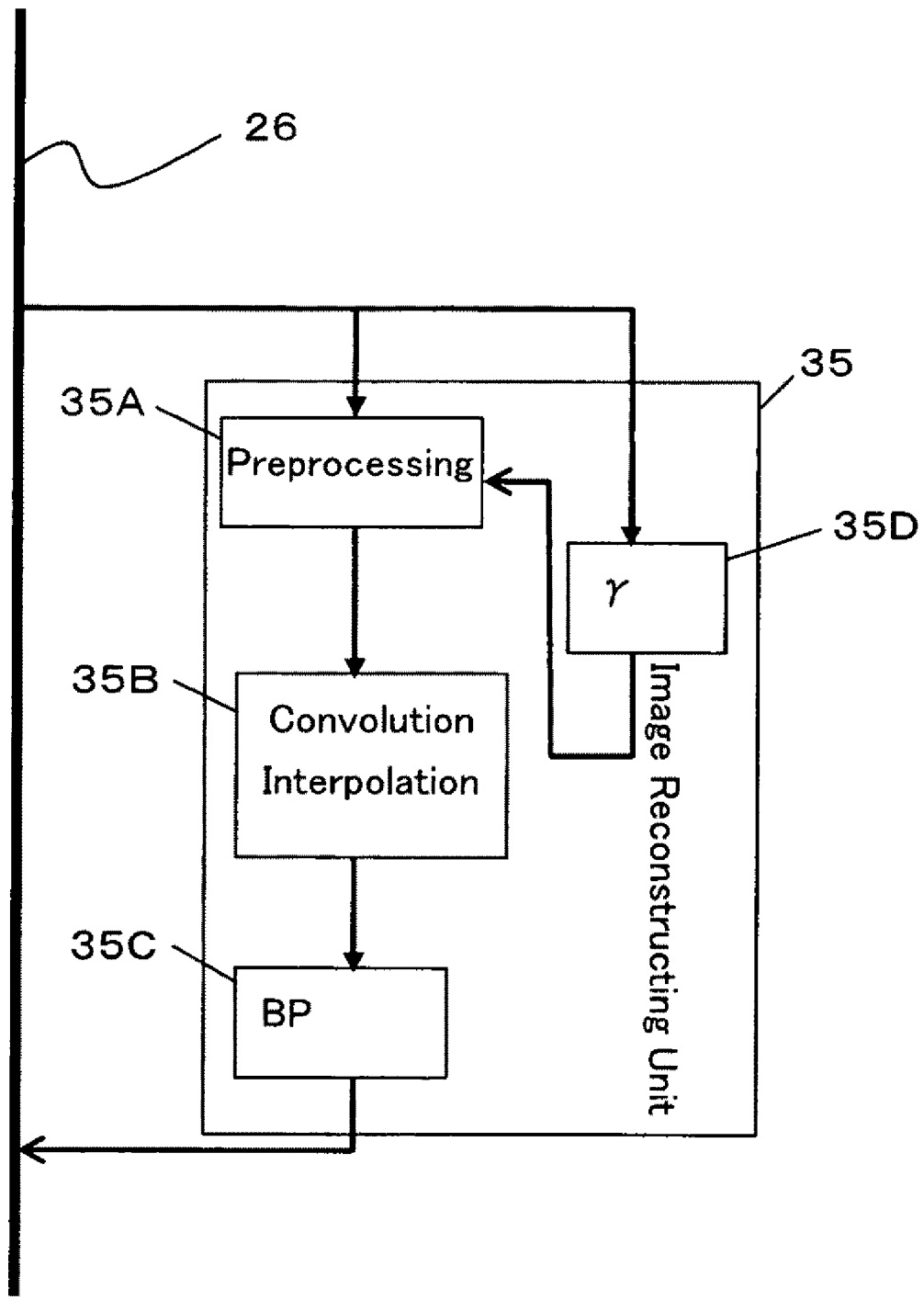
FIG. 25 is a block diagram illustrating another configuration of the image reconstruction system illustrated in FIG. 24.

Even in this case, the present invention is applicable with no problem. An image reconstructing unit 35 illustrated in FIG. 25 is a configuration example in the case where the present invention is applied to an image reconstructing unit having a back-projection arithmetic section that performs such two-dimensional back projection. The image reconstructing unit 35 is equipped with a preprocessing section 35A, a convolution-interpolation section 35B, a back-projection section 35C, and a storage section 35D. Note that parts not illustrated are the same as those illustrated in the overview of system configuration and operation illustrated in FIG. 24.

The storage section 35D is the same in function as the storage section 25D previously described, but the output, for example, information on imaginary focal positions $Z_{fo}$ and $Z_{fe}$ and detector position shift quantities $Z_{do}$ and $Z_{de}$ is delivered to the preprocessing section 35A. The preprocessing section 35A, in addition to the function of the preprocessing section 25A, sets a suitable angle and position of the inclined plane according to the orbit of a helical scan and z-coordinates of each imaging position. In the setting, the preprocessing section 35A collects projection data having angles as close as to the inclined plane possible, based on information on imaginary focal positions $Z_{fo}$ and $Z_{fe}$ and detector position shift quantities $Z_{do}$ and $Z_{de}$, not true focal position and detector position.

By approximating that the acquired projection data are all in the above-described inclined plane, the convolution-interpolation section 35B performs convolution and interpolation, and the back-projection section (BP) 35C back-projects on the above-described inclined plane the projection data on which convolution and interpolation were performed. As a result, the present invention, in which back projection is performed on a path different by a predetermined quantity in the Z-axis direction from a true path where projection data are obtained, i.e., at an optimal position where windmill-artifacts are suppressed with few blurs produced in the Z-axis direction, can be achieved automatically.

(C3) Overview 3 of Yet Another System Configuration and Operation

So far, it has been described that in multislice CTs, the X-ray beam has a cone angle. However, in multislice CTs with a small number of rows (e.g. 4 rows) the X-ray beam has a cone angle but it is common to entirely neglect the cone angle when performing image reconstruction. The image reconstruction method is described in detail in the following reference by way of example and generally called HFI (Helical Filter Interpolation).

The neglect of cone angles makes image reconstruction calculation simple, the aforementioned method has been put to practical use in generalized multislice CTs. Note that this type of bottom-of-the line multislice CT does not employ an expensive technique such as zFFS.

(Reference) K. Taguchi, H. Aradate, "Algorithm for image reconstruction in multi-slice helical CTs," Med. Phys. 1998, 25(4), 550-561.

Even in this case, windmill artifacts become a problem. It is rather a serious problem, because a scan is often performed with the scan slice thickness $s_{iso}$ made greater in this case than in the case where multislice CTs have a large number of rows.

Even in the case of such an image reconstruction method, the present invention is effective. The HFI will be described briefly.

Figure 26:
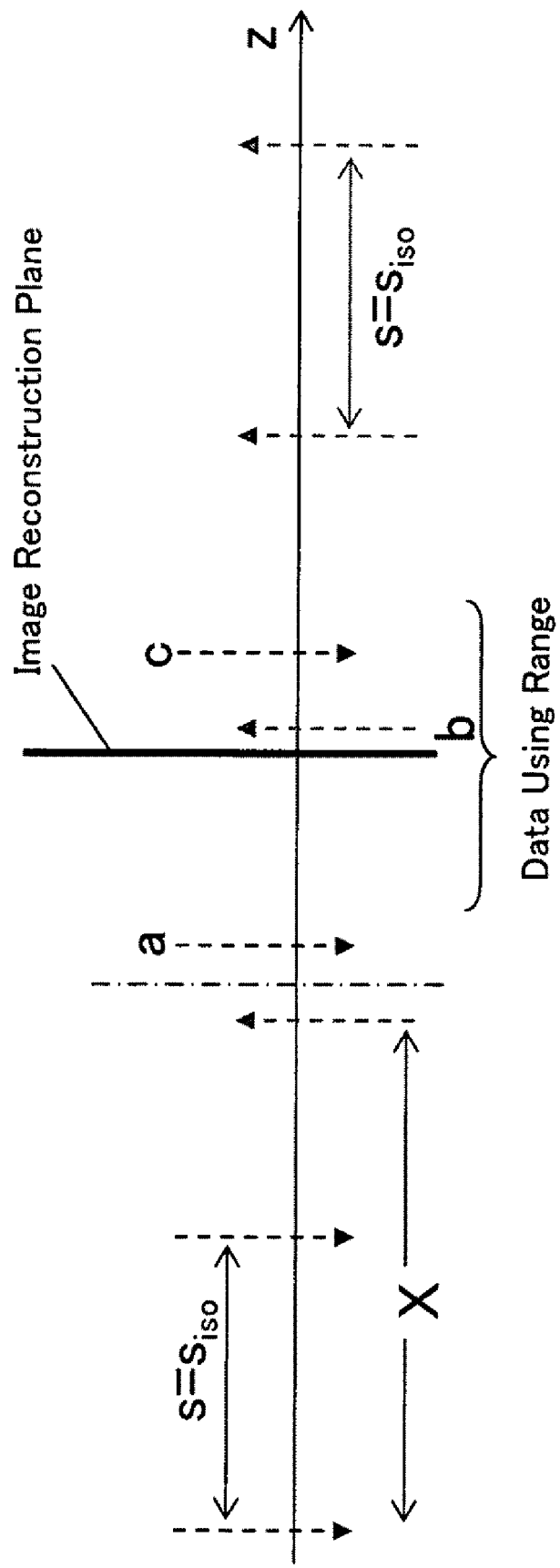
FIG. 26 is a diagram for explaining the sampling and image reconstruction method of a 4-row multislice CT.

FIG. 26, for example, illustrates the sampling points in the Z-axis direction for projection data passing through the rotation center axis. Downward projection data, indicated with downward dashed arrows, are four rows. These are referred to as "Normal Ray". Since cone angles are neglected, projection data are to be described straight and in parallel. The sampling pitch in the Z-axis direction is s, but since this neglects the cone angle, s is handled as a value si at the center of rotation although it is not the center of rotation (i.e., s=$s_{iso}$). If half a rotation is made, sampling points are shifted by helical motion (see distance X in FIG. 26) and therefore four rows of projection data, indicated with upward dashed arrows, are obtained. These are referred to as "Complementary Rays".

The normal ray and the complementary ray pass along approximately the same line, but the directions are opposed 180 degrees to each other. It is said that such a set is in an opposed relationship. Projection data in an opposed relationship can be handled equally by neglecting a difference in direction in image reconstruction.

In performing image reconstruction, both projection data nearest to the image reconstructing plane are collected and used in reconstruction calculation. At that time, the projection data using range is determined. A wider range produces a thicker image. A narrower range produces a thinner image. Projection data are used in the projection data using range, but it is standard to perform interpolation on the projection data and to perform weighting on them with a distance from the image reconstructing plane.

That is, as illustrated in FIG. 26, by performing weighting and interpolation on the projection data in the projection data using range (projection data indicated by dashed arrows b and c) to obtain new projection data, and by assuming that the new projection data is in the image reconstructing plane, image reconstruct calculations are made. In this example, the projection data indicated with the upward dashed arrow b are used with a large weight, while the projection data indicated by the downward dashed arrow c are used with a small weight.

Note that since the projection data indicated by the downward dashed arrow a are adjacent to the projection data using range, they contribute to the reconstruction of an image with a slight weight by interpolation.

Note that the positional relationship between a normal ray and a complementary ray varies depending upon a fan angle $\phi$. The distance X in FIG. 26 can be expressed by the following Eq. 30. In Eq. 30, h indicates a helical pitch.

[Formula 22]

$$X = s_{iso} h \frac{\pi - 2\phi}{\pi} \quad (30)$$

The image reconstruction system for executing the HFI method calculates this, then calculates for each $\phi$ which row the normal ray and complementary ray nearest to the image reconstructing plane belong to, then collects projection data in a predetermined range, and uses them in reconstruction calculation.

Now, a description will be given of an image reconstruction method in which the present invention is applied to the HFI method. Note that it is sufficiently possible for even the bottom-of-the line mutislice CT with a small number of rows to perform the zFFS method, and it is sufficiently possible to modify the HFI method for the zFFS method. In that case, the improved zFFS method illustrated in the present invention and an image reconstruction method based on it can also be applied, but the applying can easily be assumed in the range that has so far been described. Here, it is assumed that there is no zFFS method. Nevertheless, the use of the theory of the present invention can exhibit advantages.

Figure 27:
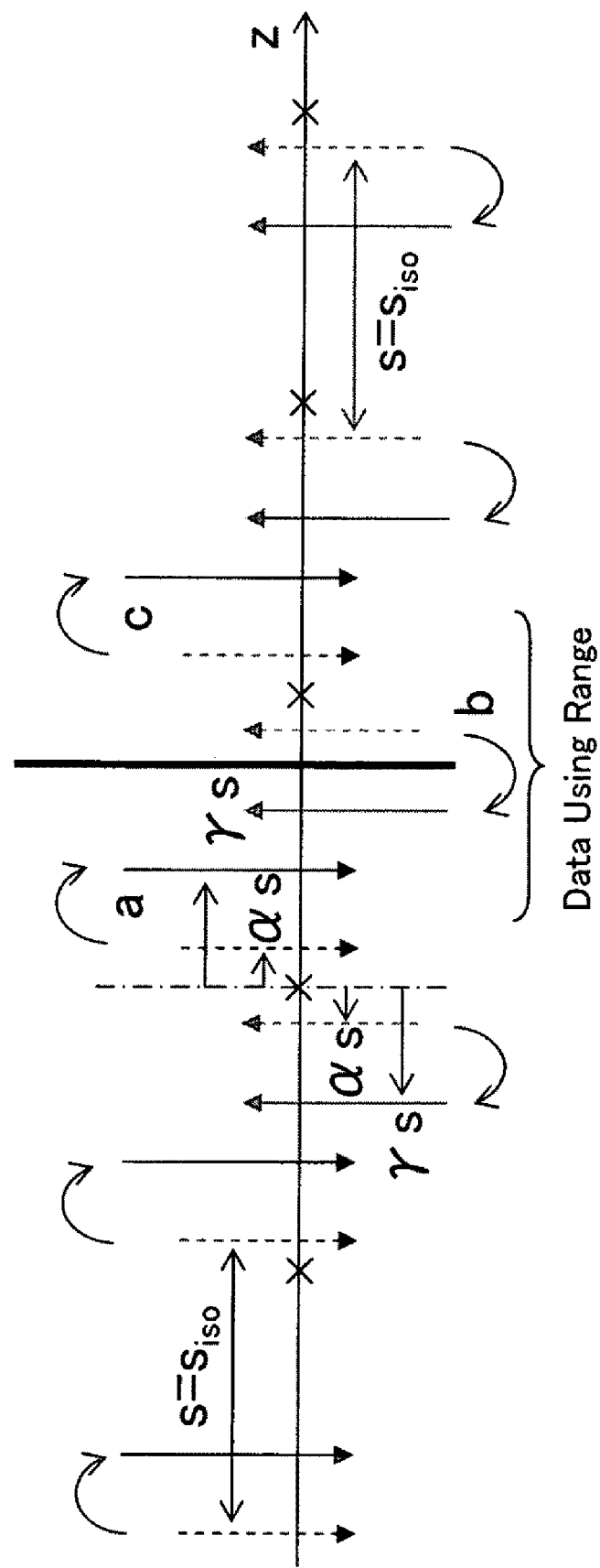
FIG. 27 is a diagram for explaining how data are handled when the image reconstruction method of the present invention is employed in the 4-row multislice CT.

FIG. 27 illustrates the state in which the present invention is applied to a standard HFI method.

Reference sampling points indicated with marks of X are located at the midpoints between normal and complementary rays. The sampling locations are assumed to be arranged at intervals of s ($s=s_{iso}$ because the present example neglects a cone angle). These locations and the locations indicated with marks of X in FIG. 14 are put in correspondence, and it is assumed that normal and complementary rays are respectively away from the location of X by $\alpha s$ ($\alpha s = \alpha_{iso} s_{iso}$ because the present example neglects a cone angle) in the arrow-indicating direction of FIG. 27. And if the theory is developed, the same results as the case leading to Eqs. 1 to 19 are obtainable.

That is, normal and complementary rays are respectively relocated at places separated away from the location of a mark of X by $\gamma s$ in the arrow-indicating direction of FIG. 27, and then data are employed. A preferable value of $\gamma$ ($\gamma = \gamma_{iso}$ because the present example neglects a cone angle) is the same as that indicated by Eq. 18. Similarly, in order to suppress windmill artifacts, an optimum value of k in Eq. 18 is 1 or so.

As a result of the relocation, the locations indicated by solid arrows in FIG. 27 are obtained. That is, the above-described projection data a, b, and c differ from the case of FIG. 26. The projection data indicated by the downward dashed arrow a is to be employed with a relatively large weight, whereas the contribution of the projection data indicated by the downward dashed arrow c is reduced. This is the difference between FIG. 27 and FIG. 26.

Note that although a cone angle is neglected, $\alpha$ is a function of fan angle $\phi$. This is because, like Eq. 30, the distance X illustrated in FIG. 26 is a function of $\phi$. However, since the HFI method takes X into consideration in making a calculation, it is easy to calculate $\alpha$ for each fan angle $\phi$. Thus, a proper $\gamma$ can be determined for each fan angle $\phi$ without any difficulty.

If a system for carrying out the above is illustrated with a figure, it is the same as FIG. 25 in the aforementioned "(C2) Overview 2 of Still Another System Configuration and Operation."

In this case, the storage section 35D functions to store an equation for calculating $\gamma$ from $\alpha$ and send it to the preprocessing section 35A. The preprocessing section 35A determines a data using range required for making an image with a thickness specified by an operator, and takes out projection data that are to be employed in calculation for reconstructing an image in a predetermined image reconstructing plane. At this time, the projection data are taken out by assuming that they are located at the position of $\gamma$, not the position of $\alpha$.

The projection data taken out are delivered to the convolution-interpolation section 35B. In this case, the back-projection section 35C, unlike the case of "(C2) Overview 2 of Still Another System Configuration and Operation," performs back projection on a cross section (two-dimensional plane) perpendicular to the Z-axis, not an inclined plane. At this time, back projection is performed by assuming the projection data are all in this two-dimensional plane.

From the foregoing, even in the CT system adopting the image reconstruction method which entirely neglects cone angles, windmill artifacts are significantly alleviated and a satisfactory image in which the image slice thickness scarcely swells is obtainable.

[D] Other Modifications (D1) First Modification

In the embodiment described above, in the case of carrying out the zFFS method, i.e., in the case of moving a focus back and forth, a helical scan is performed. In addition, specific images and quantitative data are illustrated when a helical pitch is 13. However, although a detailed description is not given, it has been confirmed that significant effects can be obtained using various helical pitches, and the theory has been established quite independently of helical pitches.

As an extreme example, for a rotational scan or conventional scan (in which there is no fixed-speed movement of a subject in the Z-axis direction) not a helical scan, the present invention is also applicable. That is, the longitudinal movement of a focal position, even in a rotational scan in which there is no movement in the Z-axis direction, makes a sampling interval in the z-axial direction fine. Even in this case, the present invention is applicable. That is, for each of odd and even views, back projection is performed according to not a path where projection data were acquired, but a different path shifted from the original path by a predetermined quantity in the Z-axis direction.

(D2) Second Modification

In the above theory explanation and embodiments, in the case of flying a focal position, it is flown for each step of a projection angle, i.e., for each of odd and even views, and a proper back projection position is selected for each of odd and even views. However, the focal-position flying method and suitable image reconstruction is merely an example.

In the above explanation, for example, if view numbers are given 0, 1, 2, 3, 4, and 5, then flying is alternately performed like −, +, −, +, −, and +. However, as another example, flying may be performed like −, 0, +−, 0, and +. Zero means that there is no flying. In this case, view numbers 0, 1, and 2 are employed as one set, i.e., for three focal positions −, 0, and +, it is easy to formulate the same equations as theoretical equations leading from Eq. 1 to Eq. 18 for odd and even views. Although details are not given, in this case it may be given as a conclusion that at a back projection position expressed by the following Eq. 31 instead of Eq. 18, aliasing artifacts, i.e., windmill artifacts are minimized.

[Formula 23]

$$\gamma = \alpha + \frac{2}{3k} - \frac{2\alpha}{k}, k \approx 1 \qquad (31)$$

More specifically, for one of the three views where no focal position is flown, back projection is performed along a path where projection data were acquired, and for the views where there is flying of a focal position, back projection is performed along a different path shifted from the original path in the Z-axis direction by a value of γ.

That is, flying a focus alternately between odd and even views is merely a simplest example. How to fly a focus is arbitrary, and appropriate image reconstruction corresponding to it can be obtained with the theory described in the present invention. In any case, it is the best to perform image reconstruction with the assumption of projection data being obtained along a path shifted by a predetermined quantity from the original path where projection data were actually acquired.

(D3) Third Modification

As seen from a variety of embodiments and modifications described above, the theory of the present invention can be expressed in more universal form, as follows. That is, if projection data acquisition positions in the Z-axis direction are arranged at equal intervals, it is the best to perform back projection according to prior art along a path where projection data were acquired, but if projection data acquisition positions in the Z-axis direction are not arranged at equal intervals, an optimum Z-axis position where those data should be back projected is obtained according to the arrangement.

Thus, the gist of the present invention resides in that, in accordance with the arrangement of projection data acquisition positions in the Z-axis direction, in reconstructing an image, a path along which those projection data should be back projected is intentionally selected as a position different from the path used at the time of the projection data acquisition.

Circumstances where the arrangement pitches in the Z-axis direction of projection data become unequal will occur even if a focus is not flown. If a helical scan is performed with a multislice CT, the Z-axis direction arrangement pitches of projection data become unequal. For instance, if a helical pitch is small, for projection data at a certain projection angle and projection data at the same projection angle after one rotation, the X-ray beams overlap each other, and if the two projection data paths are arranged in that state, they are alternately threaded through the intervals, but they are arranged at unequal intervals, not equal intervals. The degree of the unequal arrangement is dependent on a distance from the center of rotation.

In addition, even if a helical pitch is great, X-ray beams overlap each other after half one rotation, and if the two projection data paths are arranged, they are alternately threaded through the intervals, but they are arranged at unequal intervals, not equal intervals. The degree of the unequal arrangement depends upon a place. Even in such a case, the present invention illustrates that a path along which those projection data are to be back projected is different from the path where the projection data were acquired.

For the problem of unequal sampling pitches by the helical scan of the multislice CT, the present invention is also applied. As the simplest example, the application of the present invention to the case of adopting the image reconstruction method neglecting cone angles has been described in the "(C3) Overview 3 of Yet Another System Configuration and Operation". Likewise, even in the case of a more accurate image reconstruction method not neglecting cone angles, it is expected that, as shown in the present invention, by an image reconstruction method setting an optimum back projection path in circumstances of unequal sampling pitches, in the helical scan of a multislice CT, a high-quality image in which artifacts are further reduced will be obtained.

(D4) Fourth Modification

As set forth above, the gist of the present invention resides in that image reconstruction is performed by shifting projection data to a second path different by a predetermined quantity from a first path in which the projection data were actually acquired. As the simplest method for carrying out this concept, imaginary focal positions and detector position shift quantities have been described, but the present invention may be varied in many ways.

For example, a detector position shift quantity is made zero, and the shift of focal position to the imaginary position is increased by that much, and for only odd views, image reconstruction is performed. Similarly, image reconstruction is performed for only even views. In this way, the two images are to be back projected at an appropriate angle relative to the Z-axis direction indicated by the present invention, but the two images are made at positions shifted at the Z-axis from each other by a predetermined quantity resulting from the fact that the detector position shift quantity was made zero.

If the two images shifted by the predetermined quantity are added together, the resultant image is exactly the same as the image disclosed in the specific examples of the present invention. With an imaginary focal position fixed at the middle point, and a detector position shift quantity changed that much, the same may be performed. These are nothing less than the fact that image reconstruction is performed by shifting projection data to a second path different by a predetermined quantity from a first path in which the projection data were actually acquired.

(D5) Fifth Modification

As seen from various examples described above, the gist of the present invention can be summarized as follows:

Whether sampling intervals in the Z-axis direction are unequal due to flying of a focus or by a helical scan performed with a multislice CT, sampling intervals become unequal regardless of a cause. In such a case, in the knowledge that projection data by which a certain pixel on an image should be most influenced is not projection data passing through a path nearest to that pixel at the time of projection data acquisition, image reconstruction is performed such that projection data by which a certain pixel on an image is most influenced is projection data passing through a path away from that pixel by a predetermined quantity in the Z-axis direction. This is the image reconstruction method of the present invention. In addition to specific examples illustrated in the present invention, a large number of modifications for executing that method can be implemented. Such modifications would be obvious to one skilled in the art.

INDUSTRIAL APPLICABILITY

According to the present invention, as described above in detail, an image is reconstructed by performing an arithmetical operation in which projection data are back projected along a path different in the Z-axis direction from the X-ray path of the projection data. Therefore, it becomes possible to obtain a higher definition image (reconstructed image) that more effectively suppresses abnormal patterns of a reconstructed image, particularly abnormal patterns called windmill artifacts, than prior art. In addition, it becomes possible to reduce the possibility of an erroneous diagnosis and clinical difficulty due to abnormal patterns, and greatly shorten inspection time. This makes a considerable contribution to an enhancement in the value of CT diagnosis. Thus, the present invention is considered to be extremely useful in the medical field.

What is claimed is:

1. An X-ray computed tomography (CT) system comprising:
   an X-ray source for radiating X-rays;
   an X-ray detector disposed opposite to said X-ray source with a predetermined rotation center axis therebetween, and comprising a plurality of detector elements arranged two-dimensionally in a Z-axis direction, which is a direction along said rotation center axis, and a direction crossing said Z-axis direction;
   a data acquisition unit for acquiring X-ray detection data detected by said plurality of detector elements of said detector;
   scan means for causing said data acquisition unit to acquire said X-ray detection data detected by said detector by radiating X-rays from said X-ray source at each of rotational angles, while causing said X-ray source and said detector to rotate around said rotation center axis; and
   reconstruction means for performing an arithmetic operation, in which two-dimensional projection data obtained by processing the acquired X-ray detection data are back projected along a second path different in said Z-axis direction from a first path of X-rays at the time of said detection, to reconstruct an image,
   wherein a focal position of said X-ray source is constructed such that it is alternately movable on plus and minus sides in said Z-axis direction for each of said rotational angles,
   wherein projection data that are acquired at either position of the alternate movements of a focus of said X-ray source are arranged with a sampling pitch $s_{iso}$ along the Z-axis direction at said rotation center axis, and
   wherein quantities of the alternate movements of the focus of said X-ray source are determined so that, when Z-axis direction arrangement positions of respective projection data obtained at said alternate focal positions are away by $\alpha_{iso}$ (positive value) times $s_{iso}$ at said rotation center axis from a Z-axis direction arrangement position of projection data obtained when the focus is at a middle point between the alternate focal positions, said $\alpha_{iso}$ becomes a value less than ¼ and greater than 0.

2. The X-ray CT system as set forth in claim 1, wherein Z-axis direction arrangement positions, at which respective projection data obtained at said alternate focal positions are back projected, are away by $\gamma_{iso}$ (positive value) times $s_{iso}$ at said rotation center axis from the Z-axis direction arrangement position of the projection data obtained when the focus is at the middle point between the alternate focal positions;
   said $\gamma_{iso}$ is a value closer to $$\alpha_{iso}+(1-4\alpha_{iso})/2k$$

than said $\alpha_{iso}$; and
   said k is a value that is not infinity.

3. The X-ray CT system as set forth in claim 2, wherein said k is a value from approximately 1 to 2.

4. An X-ray computed tomography (CT) system comprising:
   an X-ray source for radiating X-rays;
   an X-ray detector disposed opposite to said X-ray source with a predetermined rotation center axis therebetween, and comprising a plurality of detector elements arranged two-dimensionally in a Z-axis direction, which is a direction along said rotation center axis, and a direction crossing said Z-axis direction;
   a data acquisition unit for acquiring X-ray detection data detected by said plurality of detector elements of said detector;
   scan means for causing said data acquisition unit to acquire said X-ray detection data detected by said detector by radiating X-rays from said X-ray source at each of rotational angles, while causing said X-ray source and said detector to rotate around said rotation center axis; and
   reconstruction means for performing an arithmetic operation, in which two-dimensional projection data obtained by processing the acquired X-ray detection data are back projected along a second path different in said Z-axis direction from a first path of X-rays at the time of said detection, to reconstruct an image,
   wherein a focal position of said X-ray source is constructed such that it is alternately movable on plus and minus sides in said Z-axis direction for each of said rotational angles, and
   wherein, in back projecting with said reconstruction means projection data acquired at the alternate positions of the focus of said X-ray source, a distance away from said rotation center axis toward said focus is represented by r, and at a position of said r, when attention is directed to projection data which passed the vicinity of said rotation center axis, a Z-axis direction arrangement pitch s of the attention-directed projection data is expressed as a function s(r) of said r, and a Z-axis direction position of the attention-directed projection data is expressed as being away by $\alpha(r)s(r)$ from a Z-axis direction position of arrangement of projection data obtained when the focus is at the middle point between the alternate focal positions, a position, at which said attention-directed projection data are back projected, is away by $\gamma(r)s(r)$ from the Z-axis direction position at said r of arrangement of the projection data obtained when the focus is at the middle point between the alternate focal positions, said γ(r) is significantly different from said α(r) and is a value closer to $$\alpha(r)+[1-4\alpha(r)]/2k$$

than said α(r), and said k is a value that is not infinity.

5. The X-ray CT system as set forth in claim 4, wherein said k is a value from approximately 1 to 2.

6. An X-ray computed tomography (CT) system comprising:
- an X-ray source for radiating X-rays;
- an X-ray detector disposed opposite to said X-ray source with a predetermined rotation center axis therebetween, and comprising a plurality of detector elements arranged two-dimensionally in a Z-axis direction, which is a direction along said rotation center axis, and a direction crossing said Z-axis direction;
- a data acquisition unit for acquiring X-ray detection data detected by said plurality of detector elements of said detector;
- scan means for causing said data acquisition unit to acquire said X-ray detection data detected by said detector by radiating X-rays from said X-ray source at each of rotational angles, while causing said X-ray source and said detector to rotate around said rotation center axis; and
- reconstruction means for performing an arithmetic operation, in which two-dimensional projection data obtained by processing the acquired X-ray detection data are back projected along a second path different in said Z-axis direction from a first path of X-rays at the time of said detection, to reconstruct an image,
- wherein a focal position of said X-ray source is constructed such that it is not movable alternately in said Z-axis direction for each of said rotational angles, and
- wherein, in back projecting with said reconstruction means projection data acquired at the position of the focus of said X-ray source, said projection data are arranged with a sampling pitch $s_{iso}$ in the Z-axis direction at said rotation center axis, said projection data are constructed such that they are back projected at a position away in the Z-axis direction by $\gamma_{iso}$ times $s_{iso}$ in the Z-axis direction at said rotation center axis from a position where said projection data were acquired, plus and minus signs of said $\gamma_{iso}$ are interchanged for each projection angle, and said $\gamma_{iso}$ is a value up to about ½, not zero.

7. An X-ray computed tomography (CT) system comprising:
- an X-ray source for radiating X-rays;
- an X-ray detector disposed opposite to said X-ray source with a predetermined rotation center axis therebetween, and comprising a plurality of detector elements arranged two-dimensionally in a Z-axis direction, which is a direction along said rotation center axis, and a direction crossing said Z-axis direction;
- a data acquisition unit for acquiring X-ray detection data detected by said plurality of detector elements of said detector;
- scan means for causing said data acquisition unit to acquire said X-ray detection data detected by said detector by radiating X-rays from said X-ray source at each of rotational angles, while causing said X-ray source and said detector to rotate around said rotation center axis; and
- reconstruction means for performing an arithmetic operation, in which two-dimensional projection data obtained by processing the acquired X-ray detection data are back projected along a second path different in said Z-axis direction from a first path of X-rays at the time of said detection, to reconstruct an image,
- wherein a focal position of said X-ray source is constructed such that it is not movable alternately in said Z-axis direction for each of said rotational angles, and
- wherein, in back projecting with said reconstruction means projection data acquired at the position of the focus of said X-ray source, a distance away from said rotation center axis toward said focus is represented by r, and at a position of said r, when attention is directed to projection data which passed the vicinity of said rotation center axis, a Z-axis direction arrangement pitch s of the attention-directed projection data is expressed as a function s(r) of said r, a position, at which said attention-directed projection data are back projected, is expressed as being away by ±γ(r)s(r) from a position where said attention-directed projection data were acquired, plus and minus signs of said γ(r)s(r) are interchanged for each projection angle, said γ(r) is a value close to ½k, not zero, and said k is a value from approximately 1 to 2.

8. An X-ray computed tomography (CT) system comprising:
- an X-ray source for radiating X-rays;
- an X-ray detector disposed opposite to said X-ray source with a predetermined rotation center axis therebetween, and comprising a plurality of detector elements arranged two-dimensionally in a Z-axis direction, which is a direction along said rotation center axis, and a direction crossing said Z-axis direction;
- a data acquisition unit for acquiring X-ray detection data detected by said plurality of detector elements of said detector;
- scan means for causing said data acquisition unit to acquire said X-ray detection data detected by said detector by radiating X-rays from said X-ray source at each of rotational angles, while causing said X-ray source and said detector to rotate around said rotation center axis; and
- reconstruction means for performing an arithmetic operation, in which two-dimensional projection data obtained by processing the acquired X-ray detection data are back projected along a second path different in said Z-axis direction from a first path of X-rays at the time of said detection, to reconstruct an image,
- wherein, in reconstructing an image with said reconstruction means, employing said projection data,
- a shifted focal position, defined as a position different in the Z-axis direction by a predetermined quantity from an actual focal position of said X-ray source when said projection data were acquired, is set,
- a shifted detector element position, defined as a position different in the Z-axis direction by a predetermined quantity from an actual position of said detector element when said projection data were acquired, is set, and
- said reconstruction means performs back projection along a plane connecting said shifted focal position and each row of shifted detector element positions.

9. The X-ray CT system as set forth in claim 8, wherein
- the focal position of said X-ray source is constructed such that it is alternately movable on plus and minus sides in said Z-axis direction for each of said rotational angles;
- projection data that are acquired at either position of the alternate movements of said focus are arranged with a sampling pitch $s_{iso}$ in the Z-axis direction at said rotation center axis;
- planes connecting the alternate movement positions of said focus and each row of the detector elements of said detector, at said rotation center axis, are away by a $\alpha_{iso}$ (positive value) times $s_{iso}$ from positions at said rotation center axis of arrangement of projection data obtained when the focus is at a middle point between said alternate focal positions;

said shifted focal position is approximately $\pm[(k-2)R_{FD}/k(R_{FD}-R_F)]\alpha_{iso}s_{iso};$ said shifted detector element position is a position away from a true detector element position by approximately $\pm(\tfrac{1}{2}k)(R_{FD}/R_F)\alpha_{iso};$ the plus and minus of said shifted focal position and shifted detector element position are interchanged and employed with the plus and minus in a Z-axis direction position of the focus when said projection data were acquired;

said $R_{FD}$ is a distance from the middle point of the alternate movements of the focus to a detector plane, and said $R_F$ is a distance from the middle point of the alternate movements of the focus to the rotation center; and said k is a value neither zero nor infinity.

10. The X-ray CT system as set forth in claim 9, wherein said k is a value from approximately 1 to 2.

11. An X-ray computed tomography (CT) system comprising:

an X-ray source for radiating X-rays;

an X-ray detector disposed opposite to said X-ray source with a predetermined rotation center axis therebetween, and comprising a plurality of detector elements arranged two-dimensionally in a Z-axis direction, which is a direction along said rotation center axis, and a direction crossing said Z-axis direction;

a data acquisition unit for acquiring X-ray detection data detected by said plurality of detector elements of said detector;

scan means for causing said data acquisition unit to acquire said X-ray detection data detected by said detector by radiating X-rays from said X-ray source at each of rotational angles, while causing said X-ray sauce and said detector to rotate around said rotation center axis; and reconstruction means for performing an arithmetic operation, in which two-dimensional projection data obtained by processing the acquired X-ray detection data are back projected along a second path different in said Z-axis direction from a first path of X-rays at the time of said detection, to reconstruct an image, wherein a helical scan is performed, wherein in back projecting said projection data, said projection data are used so that a position at which said projection data are back projected is different in the Z-axis direction from a path where said projection data were acquired, wherein in shifting said position in the Z-axis direction, one of two set of projection data in an opposed relationship is shifted on a plus side in the Z-axis direction, and the other is shifted on a minus side in the Z-axis direction, and wherein a focal position of said X-ray source is fixed.

12. An X-ray CT system comprising:

an X-ray source for radiating X-rays;

an X-ray detector disposed opposite to said X-ray source with a predetermined rotation center axis therebetween, and comprising a plurality of detector elements arranged two-dimensionally in a Z-axis direction, which is a direction along said rotation center axis, and a direction crossing said Z-axis direction;

a data acquisition unit for acquiring X-ray detection data detected by said plurality of detector elements of said detector;

helical scan means for causing said data acquisition unit to acquire said X-ray detection data detected by said detector by radiating X-rays from said X-ray source at each of rotational angles, while causing said X-ray source and said detector to rotate around said rotation center axis and also move in said Z-axis direction relatively with respect to a subject of examination located between said X-ray source and said detector;

means for moving a focal position of said X-ray source alternately on plus and minus sides in said Z-axis direction for each of said rotational angles; and reconstruction means for performing an arithmetic operation, in which two-dimensional projection data obtained by processing said X-ray detection data acquired are back projected along a second path different in said Z-axis direction from a first path of X-rays at the time of said detection, to reconstruct an image; and wherein, in back projecting with said reconstruction means projection data acquired at the alternate positions of the focus of said X-ray source, a distance away from said rotation center axis toward said focus is represented by r, and at a position of said r, when attention is directed to projection data in which passed the vicinity of said rotation center axis, a Z-axis direction arrangement pitch s of the attention-directed projection data is expressed as a function s(r) of said r, and a Z-axis direction position of the attention-directed projection data is expressed as being away by α(r)s(r) from a Z-axis direction position of arrangement of projection data obtained when the focus is at a middle point between the alternate focal positions;

a position, at which said attention-directed projection data are back projected, is away by γ(r)s(r) from the Z-axis direction position at said r of arrangement of the projection data obtained when the focus is at the middle point between the alternate focal positions;

said γ(r) is significantly different from said α(r) and is a value closer to $\alpha(r)+[1-4\alpha(r)]/2k$ than said α(r); and said k is a value from approximately 1 to 2.

* * * * *